United States Patent
Fuji et al.

(10) Patent No.: US 9,872,624 B2
(45) Date of Patent: Jan. 23, 2018

(54) STRAIN SENSING ELEMENT, PRESSURE SENSOR, MICROPHONE, BLOOD PRESSURE SENSOR, AND TOUCH PANEL

(71) Applicant: Kabushiki Kaisha Toshiba, Minato-ku (JP)

(72) Inventors: Yoshihiko Fuji, Kawasaki (JP); Hideaki Fukuzawa, Kawasaki (JP); Shiori Kaji, Kawasaki (JP); Akio Hori, Kawasaki (JP); Tomohiko Nagata, Yokohama (JP); Michiko Hara, Yokohama (JP); Yoshihiro Higashi, Komatsu (JP); Akiko Yuzawa, Kawasaki (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 499 days.

(21) Appl. No.: 14/471,694

(22) Filed: Aug. 28, 2014

(65) Prior Publication Data

US 2015/0082918 A1 Mar. 26, 2015

(30) Foreign Application Priority Data

Sep. 20, 2013 (JP) ................. 2013-196049

(51) Int. Cl.
*G01L 9/16* (2006.01)
*G01L 1/12* (2006.01)
(Continued)

(52) U.S. Cl.
CPC .......... *A61B 5/02141* (2013.01); *G01L 1/125* (2013.01); *G01L 9/0041* (2013.01);
(Continued)

(58) Field of Classification Search
CPC ...... B82Y 25/00; B82Y 40/00; G01R 33/093; G01R 33/098; G01R 33/091;
(Continued)

(56) References Cited

U.S. PATENT DOCUMENTS

2004/0050172 A1\* 3/2004 Quandt .................. G01L 1/125
73/779
2004/0142198 A1\* 7/2004 Van Steenkiste ....... C23C 24/04
428/553
(Continued)

FOREIGN PATENT DOCUMENTS

JP 2002-148132 A 5/2002
JP 2006-80116 A 3/2006
(Continued)

OTHER PUBLICATIONS

M. Löhndorf, et al., "Highly sensitive strain sensors based on magnetic tunneling junctions" Applied Physics Letters, vol. 81, No. 2, Jul. 8, 2002, pp. 313-315.
(Continued)

*Primary Examiner* — Hezron E Williams
*Assistant Examiner* — Gedeon M Kidanu
(74) *Attorney, Agent, or Firm* — Oblon, McClelland, Maier & Neustadt, L.L.P.

(57) ABSTRACT

According to one embodiment, a strain sensing element is provided on a film unit configured to be deformed. The strain sensing element includes a functional layer, a first magnetic layer, a second magnetic layer, and a spacer layer. The functional layer includes at least one of an oxide and a nitride. The second magnetic layer is provided between the functional layer and the first magnetic layer. A magnetization of the second magnetic layer is variable in accordance with a deformation of the film unit. The spacer layer is provided between the first magnetic layer and the second
(Continued)

magnetic layer. At least a part of the second magnetic layer is amorphous and includes boron.

20 Claims, 31 Drawing Sheets

(51) Int. Cl.
*A61B 5/021* (2006.01)
*G01L 9/00* (2006.01)
*A61B 5/00* (2006.01)

(52) U.S. Cl.
CPC .............. *G01L 9/16* (2013.01); *A61B 5/6824* (2013.01); *A61B 2562/0247* (2013.01)

(58) Field of Classification Search
CPC ... G11B 5/3163; G11B 5/3903; G11B 5/3983; G11B 2005/3996; G11B 5/3906; G11B 5/399; H01F 10/3259; H01F 10/3272; H01F 10/3295; H01F 41/303; H01F 41/325; F21K 9/232; F21K 9/64; F21V 3/04; F21V 3/049; F21V 5/00; F21Y 2115/10; A61B 2562/0247; A61B 5/02108; A61B 5/022; A61B 5/02141; A61B 5/6824; G01L 1/125; G01L 9/0041; G01L 9/16

See application file for complete search history.

(56) References Cited

U.S. PATENT DOCUMENTS

| | | | |
|---|---|---|---|
| 2006/0056115 A1 | 3/2006 | Djayaprawira et al. | |
| 2007/0035890 A1* | 2/2007 | Sbiaa | B82Y 10/00 360/324.11 |
| 2007/0195592 A1 | 8/2007 | Yuasa | |
| 2011/0295128 A1* | 12/2011 | Yuasa | A61B 5/021 600/485 |
| 2012/0050920 A1* | 3/2012 | Takeo | B82Y 25/00 360/246.1 |
| 2012/0079887 A1* | 4/2012 | Giddings | G01B 7/24 73/779 |
| 2012/0206837 A1* | 8/2012 | Fuji | G01R 33/093 360/254 |
| 2012/0245477 A1 | 9/2012 | Giddings et al. | |

FOREIGN PATENT DOCUMENTS

| | | |
|---|---|---|
| JP | 2007-180201 | 7/2007 |
| JP | 4355439132 | 11/2009 |
| JP | 2012-78186 A | 4/2012 |
| JP | 2012-151494 A | 8/2012 |
| JP | 2012-160681 A | 8/2012 |
| JP | 2012-204479 A | 10/2012 |
| JP | 2013-33881 A | 2/2013 |
| JP | 2013-72712 A | 4/2013 |

OTHER PUBLICATIONS

D. Meyners, et al., "Pressure sensor based on magnetic tunnel junctions" Journal of Applied Physics, vol. 105, 2009, pp. 07C914-1-07C914-3.

\* cited by examiner

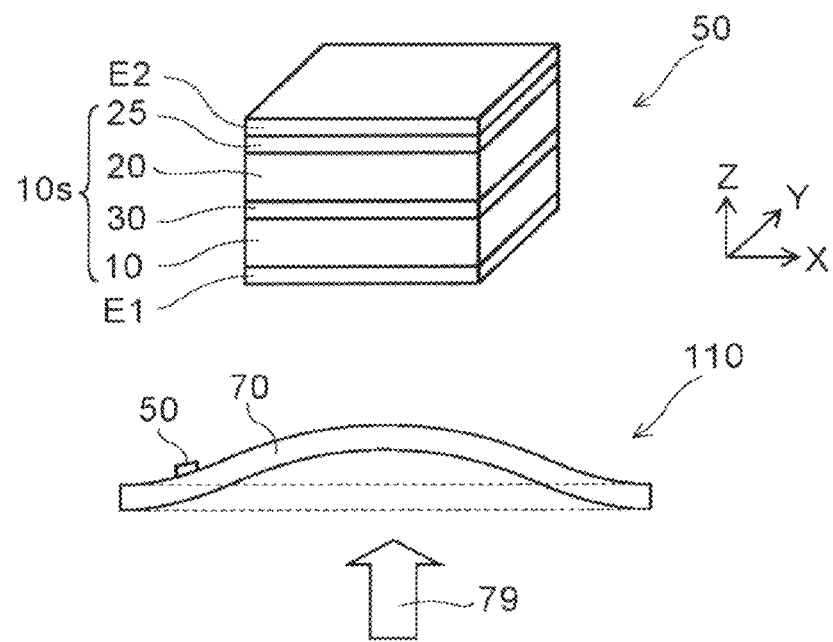
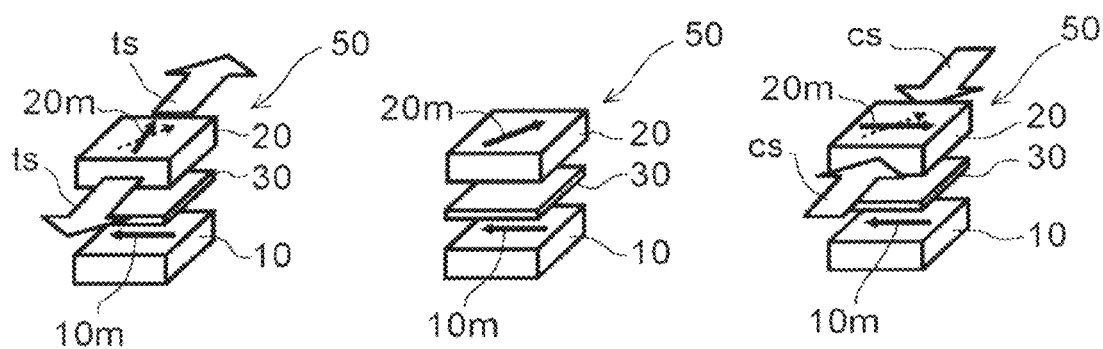

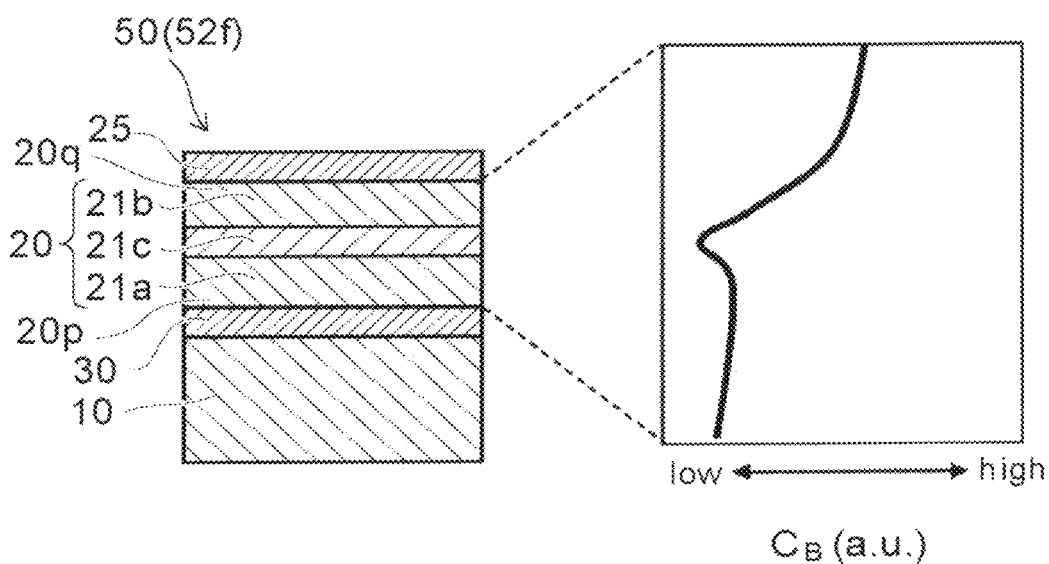
FIG. 18A
FIG. 18B
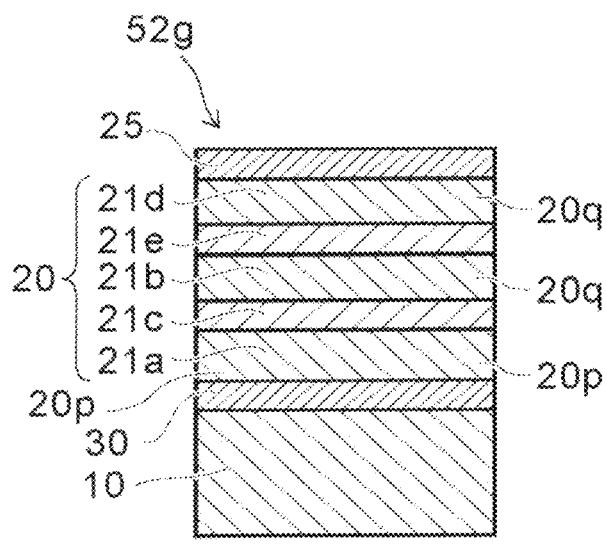
FIG. 18C

FIG. 29A
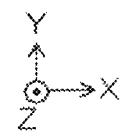
FIG. 29B
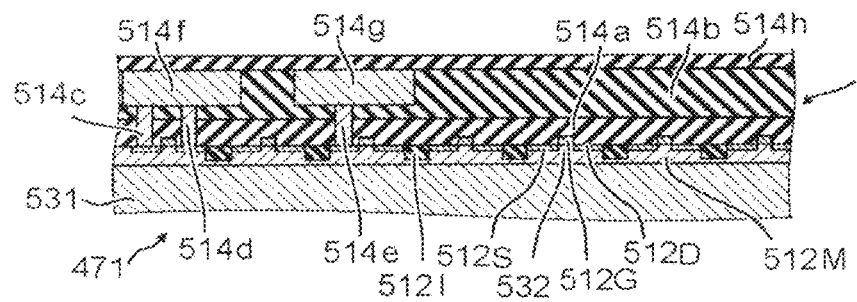
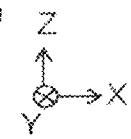
FIG. 30A
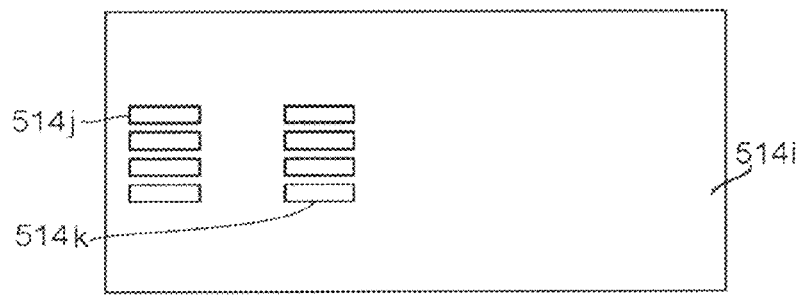
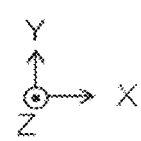
FIG. 30B
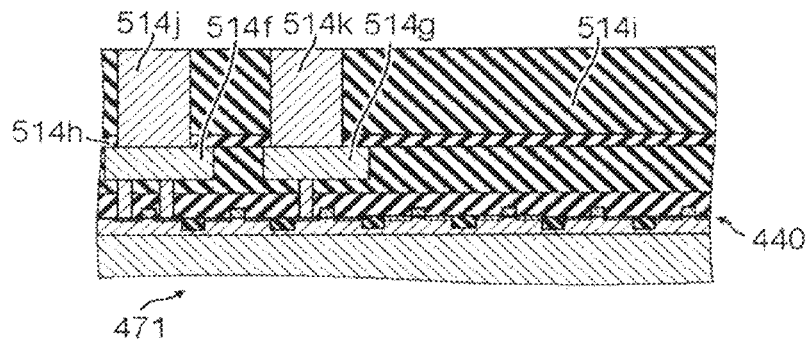
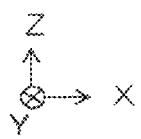

STRAIN SENSING ELEMENT, PRESSURE SENSOR, MICROPHONE, BLOOD PRESSURE SENSOR, AND TOUCH PANEL

CROSS-REFERENCE TO RELATED APPLICATIONS

This application is based upon and claims the benefit of priority from Japanese Patent Application No. 2013-196049, filed on Sep. 20, 2013; the entire contents of which are incorporated herein by reference.

FIELD

Embodiments described herein relate generally to a strain sensing element, a pressure sensor, a microphone, a blood pressure sensor, and a touch panel.

BACKGROUND

For pressure sensors using MEMS (micro electro mechanical systems) technology, there are a piezoresistance change type and an electrostatic capacitance type, for example. On the other hand, a pressure sensor using spin-electronics technology is proposed. In the pressure sensor using spin-electronics technology, a resistance change in accordance with strain is sensed. It is desired for strain sensing devices used for pressure sensors etc. to improve sensitivity, for example.

BRIEF DESCRIPTION OF THE DRAWINGS

FIG. 1 A and FIG. 1B are schematic views showing a strain sensing element according to a first embodiment;
FIG. 2A to FIG. 2C are schematic views showing operations of the strain sensing element according to the first embodiment;
FIG. 18A to FIG. 18C are schematic diagrams showing other strain sensing elements according to the first embodiment;
FIG. 29A and FIG. 29B are schematic views showing a method for manufacturing a pressure sensor according to the embodiment;
FIG. 30A and FIG. 30B are schematic views showing a method for manufacturing a pressure sensor according to the embodiment.

DETAILED DESCRIPTION

Figure 3:
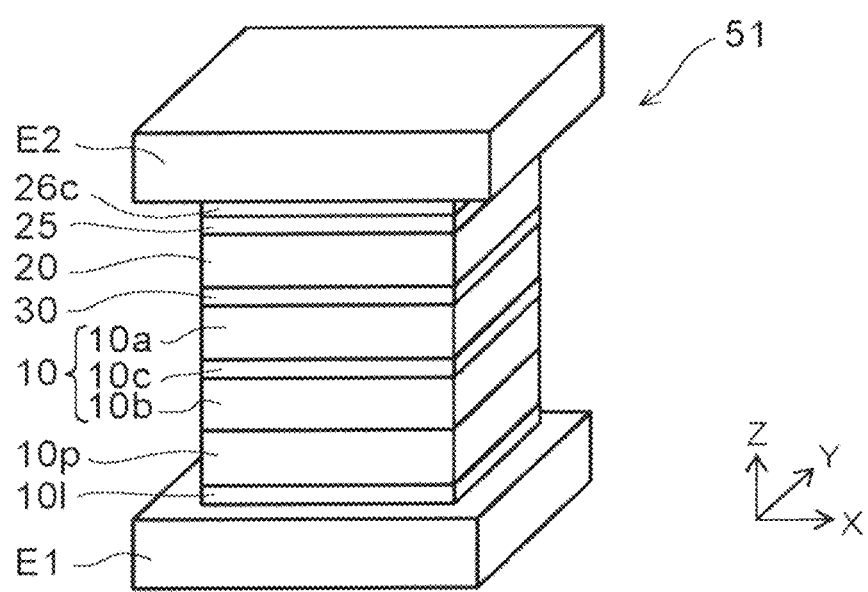
FIG. 3 is a schematic perspective view showing a strain sensing element according to the first embodiment.

According to one embodiment, a strain sensing element is provided on a film unit configured to be deformed. The strain sensing element includes a functional layer, a first magnetic layer, a second magnetic layer, and a spacer layer. The functional layer includes at least one of an oxide and a nitride. The second magnetic layer is provided between the functional layer and the first magnetic layer. A magnetization of the second magnetic layer is variable in accordance with a deformation of the film unit. The spacer layer is provided between the first magnetic layer and the second magnetic layer. At least a part of the second magnetic layer is amorphous and includes boron.

According to one embodiment, a pressure sensor includes a strain sensing element and a film unit. The strain sensing element is provided on the film unit configured to be deformed. The strain sensing element includes a functional layer including at least one of an oxide and a nitride, a first magnetic layer, a second magnetic layer provided between the functional layer and the first magnetic layer, a magnetization of the second magnetic layer being variable in accordance with a deformation of the film unit, and a spacer layer provided between the first magnetic layer and the second magnetic layer. At least a part of the second magnetic layer is amorphous and includes boron.

According to one embodiment, a microphone comprising a pressure sensor. The pressure sensor includes a strain sensing element and a film unit. The strain sensing element is provided on the film unit configured to be deformed. The strain sensing element includes a functional layer including at least one of an oxide and a nitride, a first magnetic layer, a second magnetic layer provided between the functional layer and the first magnetic layer, a magnetization of the second magnetic layer being variable in accordance with a deformation of the film unit, and a spacer layer provided between the first magnetic layer and the second magnetic layer. At least a part of the second magnetic layer is amorphous and includes boron.

According to one embodiment, a blood pressure sensor includes a pressure sensor. The pressure sensor includes a strain sensing element and a film unit. The strain sensing element is provided on the film unit configured to be deformed. The strain sensing element includes a functional layer including at least one of an oxide and a nitride, a first magnetic layer, a second magnetic layer provided between the functional layer and the first magnetic layer, a magnetization of the second magnetic layer being variable in accordance with a deformation of the film unit, and a spacer layer provided between the first magnetic layer and the second magnetic layer. At least a part of the second magnetic layer is amorphous and includes boron.

According to one embodiment, a touch panel includes a pressure sensor. The pressure sensor includes a strain sensing element and a film unit. The strain sensing element is provided on the film unit configured to be deformed. The strain sensing element includes a functional layer including at least one of an oxide and a nitride, a first magnetic layer, a second magnetic layer provided between the functional layer and the first magnetic layer, a magnetization of the second magnetic layer being variable in accordance with a deformation of the film unit, and a spacer layer provided between the first magnetic layer and the second magnetic layer. At least a part of the second magnetic layer is amorphous and includes boron.

Various embodiments will be described hereinafter with reference to the accompanying drawings.

The drawings are schematic or conceptual; and the relationships between the thickness and width of portions, the proportions of sizes among portions, etc. are not necessarily the same as the actual values thereof. Further, the dimensions and proportions may be illustrated differently among drawings, even for identical portions.

In the specification of this application and the drawings, components similar to those described in regard to a drawing thereinabove are marked with the same reference numerals, and a detailed description is omitted as appropriate.

First Embodiment

FIG. 1A and FIG. 1B are schematic views illustrating a strain sensing element according to a first embodiment.

FIG. 1A is a schematic perspective view of the strain sensing element, and FIG. 1B is a schematic cross-sectional view illustrating a pressure sensor in which the strain sensing element is used.

As shown in FIG. 1A, a strain sensing element 50 according to the embodiment includes a functional layer 25, a first magnetic layer 10, a second magnetic layer 20, and a spacer layer 30.

For the functional layer 25, at least one of an oxide and a nitride is used, for example. The functional layer 25 includes at least one of an oxide of at least one selected from a first group consisting of magnesium (Mg), aluminum (Al), silicon (Si), titanium (Ti), vanadium (V), chromium (Cr), manganese (Mn), iron (Fe), cobalt (Co), nickel (Ni), copper (Cu), zinc (Zn), zirconium (Zr), niobium (Nb), molybdenum (Mo), ruthenium (Ru), rhodium (Rh), palladium (Pd), silver (Ag), hafnium (Hf), tantalum (Ta), tungsten (W), tin (Sn), cadmium (Cd), and gallium (Ga) and a nitride of at least one selected from the first group, for example.

The functional layer 25 may include an oxide of at least one selected from a second group consisting of magnesium, titanium, vanadium, zinc, tin, cadmium, and gallium, for example. Magnesium oxide is used for the functional layer 25, for example.

The second magnetic layer 20 is provided between the functional layer 25 and the first magnetic layer 10. The second magnetic layer 20 includes an amorphous portion. The second magnetic layer 20 includes boron (B). The magnetization of the second magnetic layer 20 (the direction thereof) is variable. The magnetization of the second magnetic layer 20 changes in accordance with the strain applied to the second magnetic layer 20. The second magnetic layer 20 has an amorphous structure, for example. As described later, the second magnetic layer 20 may include an amorphous portion and a crystalline portion. That is, at least part of the second magnetic layer 20 is amorphous.

The spacer layer 30 is provided between the first magnetic layer 10 and the second magnetic layer 20.

The second magnetic layer 20 is a magnetization free layer, for example. The first magnetic layer 10 is a reference layer, for example. A magnetization pinned layer or a magnetization free layer is used as the reference layer. The change in magnetization of the second magnetic layer 20 is easier than the change in magnetization of the first magnetic layer 10, for example. When a stress is applied to the strain sensing element 50 and the strain sensing element 50 is provided with a strain, the relative angle between the magnetization of the first magnetic layer 10 and the magnetization of the second magnetic layer 10 is changed.

The direction from the first magnetic layer 10 toward the second magnetic layer 20 is defined as the Z-axis direction (the stacking direction), for example. One direction perpendicular to the Z-axis direction is defined as the X-axis direction. The direction perpendicular to the Z-axis direction and the X-axis direction is defined as the Y-axis direction.

In this example, a first electrode E1 and a second electrode E2 are further provided. The first magnetic layer 10 is provided between the first electrode E1 and the second electrode E2. The spacer layer 30 is provided between the first magnetic layer 10 and the second electrode E2. The second magnetic layer 20 is provided between the spacer layer 30 and the second electrode E2. The functional layer 25 is provided between the second magnetic layer 20 and the second electrode E2. In this example, the second magnetic layer 20 is in contact with the functional layer 25.

By applying a voltage between the first electrode E1 and the second electrode E2, a current can be passed through a stacked body 10s including the first magnetic layer 10, the spacer layer 30, the second magnetic layer 20, and the functional layer 25. The current runs along the Z-axis direction between the first magnetic layer 10 and the second magnetic layer 20, for example.

As shown in FIG. 2B, the strain sensing element 50 is used for a pressure sensor 110. The pressure sensor 110 includes a film unit 70 and the strain sensing element 50. The film unit 70 has a flexible region. The film unit 70 can be deformed. The strain sensing element 50 is fixed to the film unit 70. In the specification of this application, the state of being fixed includes the state of being directly fixed and the state of being indirectly fixed by another component. The state where the sensing element 50 is fixed to the film unit 70 includes a state where the relative positions between the sensing element 50 and the film unit 70 are fixed, for example. The strain sensing element 50 is provided on part of the film unit 70, for example.

In the specification of this application, the state of being "provided on" includes not only the state of being provided in direct contact but also the state of being provided via another component.

When a force 79 is applied to the film unit 70, the film unit 70 is deformed. A strain is generated in the strain sensing element 50 in conjunction with the deformation. The magnetization of the second magnetic layer 20 changes in accordance with the deformation of the film unit, for example.

In the strain sensing element 50 according to the embodiment, a strain is generated in the strain sensing element 50 when the film unit 70 is deformed by a force from the outside, for example. The strain sensing element 50 converts the change in strain to a change in electric resistance.

The operation in which the strain sensing element 50 functions as a strain sensor is based on application of "inverse magnetostriction effect" and "magnetoresistance effect." The "inverse magnetostriction effect" is obtained in a ferromagnetic layer used as a magnetization free layer. The "magnetoresistance effect" is exhibited in a stacked film of a magnetization free layer, a spacer layer, and a reference layer (for example, a magnetization pinned layer).

The "inverse magnetostriction effect" is a phenomenon in which the magnetization of a ferromagnetic material is changed by a strain generated in the ferromagnetic material. That is, when an external strain is applied to the stacked body 10s of the strain sensing element 50, the magnetization direction of the magnetization free layer is changed. Consequently, the relative angle between the magnetization of the magnetization free layer and the magnetization of the reference layer (for example, a magnetization pinned layer) is changed. At this time, a change in electric resistance is caused by the "magnetoresistance effect (MR effect)." The MR effect includes GMR (giant magnetoresistance) effect, TMR (tunneling magnetoresistance) effect, or the like, for example. The MR effect is exhibited by passing a current through the stacked body 10s to read the change in relative angle between the directions of the magnetizations as an electric resistance change. A strain is generated in the stacked body 10s (the strain sensing element 50), the direction of the magnetization of the magnetization free layer is changed by the strain, and the relative angle between the direction of the magnetization of the magnetization free layer and the direction of the magnetization of the reference layer (for example, a magnetization pinned layer) is changed, for example. That is, the MR effect appears due to the inverse magnetostriction effect.

When the ferromagnetic material used for the magnetization free layer has a positive magnetostriction constant, the direction of the magnetization changes so that the angle between the direction of the magnetization and the direction of a tensile strain becomes smaller and the angle between the direction of the magnetization and the direction of a compressive strain becomes larger. When the ferromagnetic material used for the magnetization free layer has a negative magnetostriction constant, the direction of the magnetization changes so that the angle between the direction of the magnetization and the direction of a tensile strain becomes larger and the angle between the direction of the magnetization and the direction of a compressive strain becomes smaller.

When the combination of the materials of the stacked body of the magnetization free layer, the spacer layer, and the reference layer (for example, a magnetization pinned layer) has a positive magnetoresistance effect, the electric resistance decreases as the relative angle between the magnetization free layer and the magnetization pinned layer decreases. When the combination of the materials of the stacked body of the magnetization free layer, the spacer layer, and the magnetization pinned layer has a negative magnetoresistance effect, the electric resistance increases as the relative angle between the magnetization free layer and the magnetization pinned layer decreases.

Examples of the change in magnetization will now be described using an example in which the ferromagnetic materials used for the magnetization free layer has a positive magnetostriction constant, and the stacked body including the magnetization free layer, the spacer layer, and the reference layer (for example, a magnetization pinned layer) has a positive magnetoresistance effect.

FIG. 2A to FIG. 2C are schematic views illustrating operations of the strain sensing element according to the first embodiment.

FIG. 2A corresponds to a state where a tensile stress is is applied to the strain sensing element 50 (a tensile state STt). FIG. 2B corresponds to a state where the strain sensing element 50 has no strain (a no-strain state ST0). FIG. 2C corresponds to a state where a compressive stress cs is applied to the strain sensing element 50 (a compressive state STc).

In the drawings, for easier viewing of the drawings, the first magnetic layer 10, the second magnetic layer 20, and the spacer layer 30 are depicted, and the functional layer 25 is omitted. In this example, the second magnetic layer 20 is a magnetization free layer, and the first magnetic layer 10 is a magnetization pinned layer.

As shown in FIG. 2B, in the no-strain state ST0 where there is no strain (for example, the initial state), the relative angle between the magnetization 20m of the second magnetic layer 20 and the magnetization 10m of the first magnetic layer 10 (for example, a magnetization pinned layer) is set to a prescribed value. The direction of the magnetization of the magnetic layer in the initial state is set by a hard bias, the shape anisotropy of the magnetic layer, or others, for example. In this example, the magnetization 20m of the second magnetic layer 20 (a magnetization free layer) and the magnetization 10m of the first magnetic layer 10 (for example, a magnetization pinned layer) cross each other.

As shown in FIG. 2A, in the tensile state STt, when a tensile stress ts is applied, a strain in accordance with the tensile stress ts is generated in the strain sensing element 50. At this time, the magnetization 20m of the second magnetic layer 20 (a magnetization free layer) changes from the no-strain state ST0 so that the angle between the magnetization 20m and the direction of the tensile stress ts becomes smaller. In the example shown in FIG. 2A, when a tensile stress ts is applied, the relative angle between the magnetization 20m of the second magnetic layer 20 (a magnetization free layer) and the magnetization 10m of the first magnetic layer 10 (for example, a magnetization pinned layer) is decreased as compared to the no-strain state ST0. Thereby, the electric resistance in the strain sensing element 50 is decreased as compared to the electric resistance in the no-strain state ST0.

As shown in FIG. 2C, in the compressive state STc, when a compressive stress cs is applied, the magnetization 20m of the second magnetic layer 20 (a magnetization free layer) changes from the no-strain state ST0 so that the angle between the magnetization 20m and the direction of the compressive stress cs becomes larger. In the example shown in FIG. 2C, when a compressive stress cs is applied, the relative angle between the magnetization 20m of the second magnetic layer 20 (a magnetization free layer) and the magnetization 10m of the first magnetic layer 10 (for example, a magnetization pinned layer) is increased as compared to the no-strain state ST0. Thereby, the electric resistance in the strain sensing element 50 is increased.

Thus, in the strain sensing element 50, the change in strain generated in the strain sensing element 50 is converted to a change in electric resistance. In the operations mentioned above, the amount of change in electric resistance (dR/R) per unit strain (dE) is referred to as a gauge factor (GF). By using a strain sensing element with a high gauge factor, a high-sensitivity strain sensor is obtained.

Examples of the strain sensing element 50 will now be described.

In the following, the description of "material A/material B" refers to the state where a layer of material B is provided on a layer of material A.

FIG. 3 is a schematic perspective view illustrating a strain sensing element according to the first embodiment.

As shown in FIG. 3, a strain sensing element 51 used in the embodiment includes the first electrode E1, an underlayer 10l, a pinning layer 10p, the first magnetic layer 10, the spacer layer 30, the second magnetic layer 20, the functional layer 25, and a cap layer 26c. The underlayer 10l is provided between the first electrode E1 and the first magnetic layer 10. The pinning layer 10p is provided between the underlayer 10l and the first magnetic layer 10. The cap layer 26c is provided between the second magnetic layer 20 and the second electrode E2. In this example, the first magnetic layer 10 includes a first magnetization pinned layer 10a, a second magnetization pinned layer 10b, and a magnetic coupling layer 10c. The first magnetization pinned layer 10a is provided between the second magnetization pinned layer 10b and the spacer layer 30. The magnetic coupling layer 10c is provided between the second magnetization pinned layer 10b and the first magnetization pinned layer 10a.

As the underlayer 10l, Ta/Ru is used, for example. The thickness (the length in the Z-axis direction) of the Ta layer is 3 nanometers (nm), for example. The thickness of the Ru layer is 2 nm, for example.

As the pinning layer 10p, an IrMn layer with a thickness of 7 nm is used, for example.

As the second magnetization pinned layer 10b, a $Co_{75}Fe_{25}$ layer with a thickness of 2.5 nm is used, for example.

As the magnetic coupling layer 10c, a Ru layer with a thickness of 0.9 nm is used, for example.

As the first magnetization pinned layer 10a, a $Co_{40}Fe_{40}B_{20}$ layer with a thickness of 3 nm is used, for example.

As the spacer layer 30, a Mg—O layer with a thickness of 1.6 nm is used, for example.

As the second magnetic layer 20, $Co_{40}Fe_{40}B_{20}$ with a thickness of 4 nm is used, for example.

As the functional layer 25, a Mg—O layer with a thickness of 1.5 nm is used, for example.

As the cap layer 26c, Ta/Ru is used, for example. The thickness of the Ta layer is 1 nm, for example. The thickness of the Ru layer is 5 nm, for example.

As the first electrode E1 and the second electrode E2, a metal is used, for example.

Characteristics of the strain sensing element according to the embodiment will now be described.

The material and thickness of the layers included in a first sample S01 are as follows:

The underlayer 10l: Ta (1 nm)/Ru (2 nm)

The pinning layer 10p: $Ir_{22}Mn_{78}$ (7 nm)

The second magnetization pinned layer 10b: $Co_{75}Fe_{25}$ (2.5 nm)

The magnetic coupling layer 10c: Ru (0.9 nm)

The first magnetization pinned layer 10a: $Co_{40}Fe_{40}B_{20}$ (3 nm)

The spacer layer 30: Mg—O (1.6 nm)

The second magnetic layer 20: $Co_{40}Fe_{40}B_{20}$ (4 nm)

The functional layer 25: Mg—O (1.5 nm)

The cap layer 26c: Cu (1 nm)/Ta (20 nm)/Ru (50 nm)

On the other hand, in a second sample S02, the functional layer 25 is not provided. Otherwise, the configuration of the second sample S02 is the same as the first sample S01.

As mentioned above, in the first sample S01, a $Co_{40}Fe_{40}B_{20}$ layer with a thickness of 4 nm is used as the second magnetic layer 20. A Mg—O layer with a thickness of 1.5 nm is used as the functional layer 25. On the other hand, in the second sample S02, the functional layer 25 is not provided.

The Mg—O layers used as the spacer layer 30 and the functional layer 25 are formed by forming a Mg layer with a thickness of 1.6 nm and then performing surface oxidation using IAO (ion beam-assisted oxidation) processing. The oxidation conditions in the fabrication of the Mg—O layer for the functional layer 25 are weaker than the oxidation conditions in the fabrication of the Mg—O layer for the spacer layer 30, for example. The resistance-area product (RA) of the Mg—O layer for the functional layer 25 is lower than the resistance-area product (RA) of the Mg—O layer for the spacer layer 30. When the resistance-area product (RA) of the Mg—O layer for the functional layer 25 is higher than the resistance-area product (RA) of the Mg—O layer for the spacer layer 30, the parasitic resistance is increased due to the functional layer 25, the MR ratio is reduced, and the gauge factor is decreased. By setting the resistance-area product (RA) of the Mg—O layer for the functional layer 25 lower than the resistance-area product (RA) of the Mg—O layer for the spacer layer 30, the parasitic resistance can be reduced, a high MR ratio is obtained, and a high gauge factor is obtained.

The stacked film mentioned above is formed on the first electrode E1, and the second electrode E2 is formed on the stacked film. The stacked film mentioned above (the first sample S01 and the second sample S02) is processed into a dot-like element. The element size of the stacked film (sample) is 20 μm×20 μm. The vertical current passage characteristics between the first electrode E1 and the second electrode E2 are investigated.

The strain sensor characteristics of the samples mentioned above are investigated by the substrate bending method. In this method, a substrate (wafer) on which the sample is formed is cut into a rectangular shape, and the four point bending method with knife edges is used to apply a stress to the wafer to form a strain in the wafer. A load cell is incorporated in the knife edge that bends the rectangular wafer. The strain applied to the sample (the strain sensing element) on the wafer is found by the load measured by the load cell.

Formula 1 below regarding two side support beams is used for the calculation of the strain.

$$\epsilon = -3(L_1-L_2)G/(2Wt^2 e_s)$$ Formula 1

In Formula 1 above, "$e_s$" is the Young's modulus of the wafer. "$L_1$" is the inter-edge length of the outer knife edges. "$L_2$" is the inter-edge length of the inner knife edges. "W" is the width of the rectangular wafer. "t" is the thickness of the rectangular wafer. "G" is the load applied to the knife edge. The load applied to the knife edge can be altered continuously by motor control.

Figure 4A:
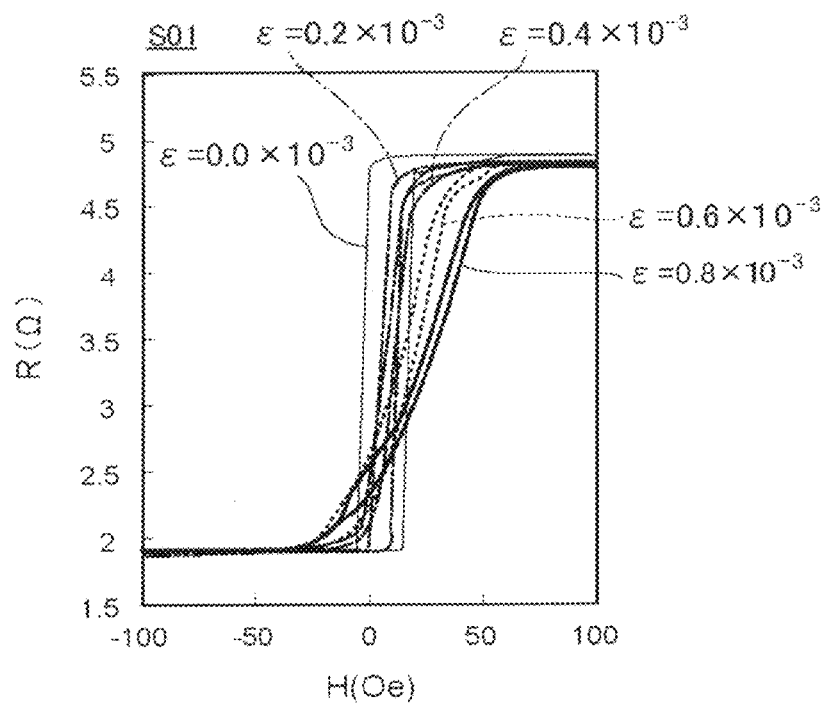
FIG. 4A and FIG. 4B are graphs showing characteristics of a strain sensing element.
Figure 4B:
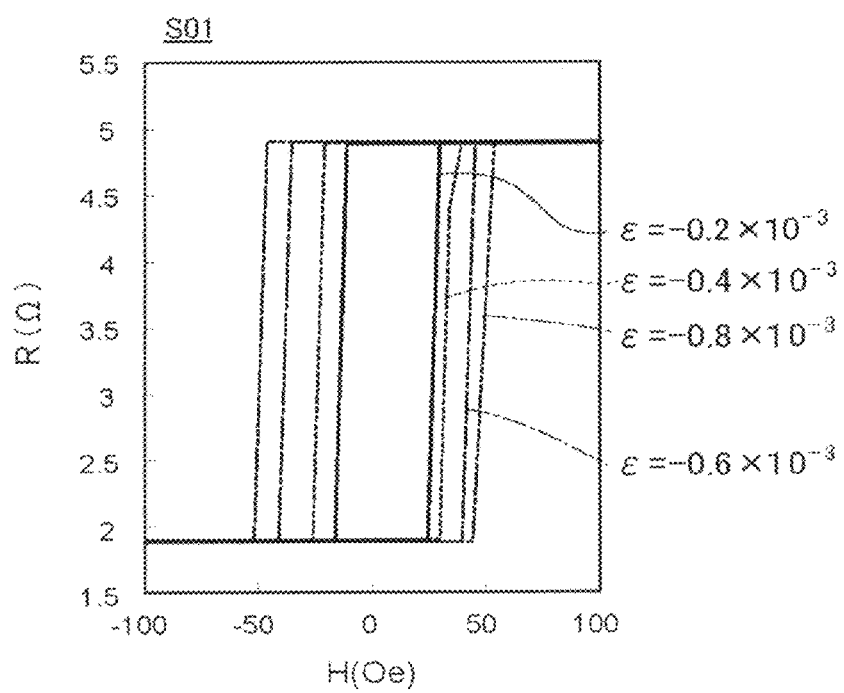

FIG. 4A and FIG. 4B are graphs illustrating characteristics of a strain sensing element.

Figure 5A:
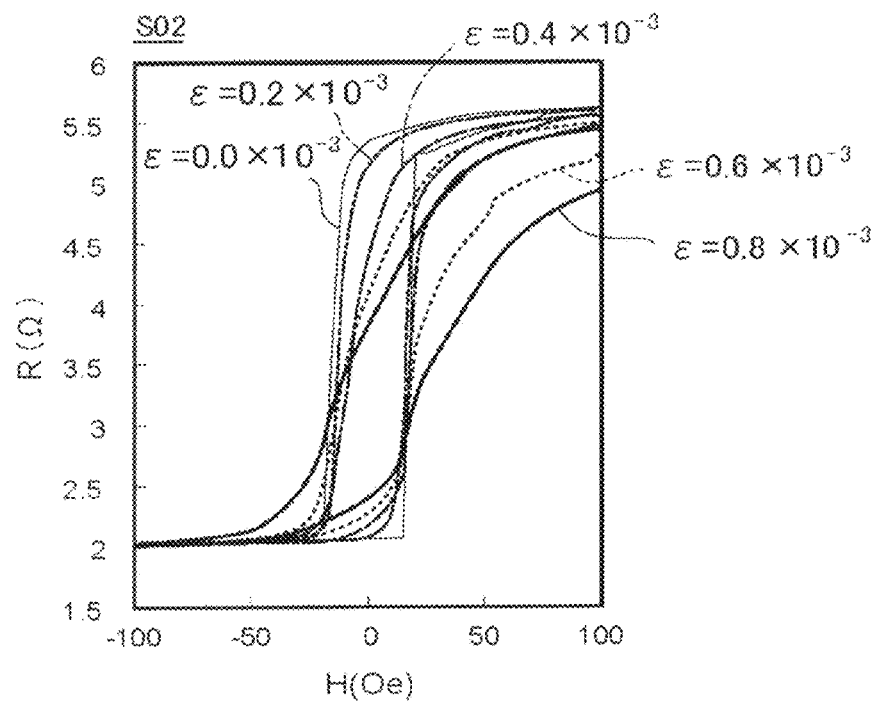
FIG. 5A and FIG. 5B are graphs showing characteristics of a strain sensing element.
Figure 5B:
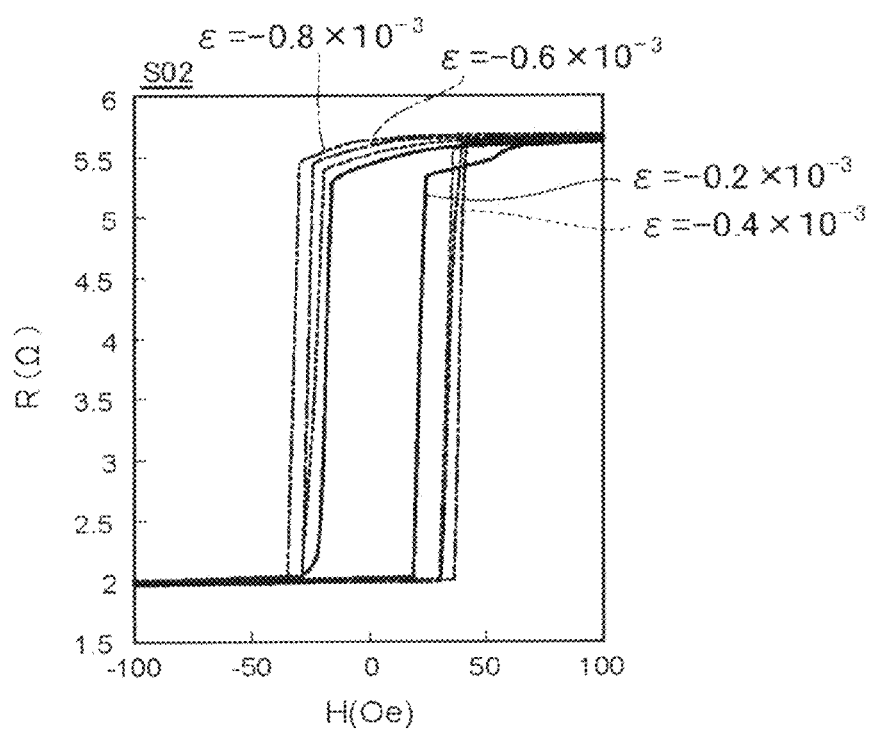

FIG. 5A and FIG. 5B are graphs illustrating characteristics of a strain sensing element.

FIG. 4A and FIG. 4B show the investigation results of the strain sensor characteristics of the first sample S01. FIG. 4A shows the measurement results of the magnetic field dependence of the electric resistance when the strain $\epsilon$ is $0.8\times10^{-3}$, $0.6\times10^{-3}$, $0.4\times10^{-3}$, $0.2\times10^{-3}$, and $0.0\times10^{-3}$. FIG. 4B shows the measurement results of the magnetic field dependence of the electric resistance when the strain $\epsilon$ is $-0.2\times10^{-3}$, $-0.4\times10^{-3}$, $-0.6\times10^{-3}$, and $-0.8\times10^{-3}$.

FIG. 5A and FIG. 5B show the investigation results of the strain sensor characteristics of the second sample S02. FIG. 5A shows the measurement results of the magnetic field dependence of the electric resistance when the strain $\epsilon$ is $0.8\times10^{-3}$, $0.6\times10^{-3}$, $0.4\times10^{-3}$, $0.2\times10^{-3}$, and $0.0\times10^{-3}$. FIG. 5B shows the measurement results of the magnetic field dependence of the electric resistance when the strain $\epsilon$ is $-0.2\times10^{-3}$, $-0.4\times10^{-3}$, $-0.6\times10^{-3}$, and $-0.8\times10^{-3}$.

The horizontal axis of the drawings is the external magnetic field H (oersteds; Oe). The vertical axis is the electric resistance R (ohm; Ω). The direction of the external magnetic field H in the measurement is a direction parallel to the plane of the first magnetization pinned layer 10a. The negative external magnetic field H corresponds to the magnetic field in the same direction as the direction of the magnetization of the first magnetization pinned layer 10a.

The direction of the application of strain $\epsilon$ is a direction perpendicular to the magnetization direction of the first magnetic layer (for example, a magnetization pinned layer) in the X-Y plane. In the specification of this application, the value of the strain $\epsilon$ being positive corresponds to tensile strain. The value of the strain $\epsilon$ being negative corresponds to compressive strain.

As can be seen from FIG. 4A, FIG. 4B, FIG. 5A, and FIG. 5I, the R-H loop shape changes with the value of the strain $\epsilon$ in the first sample S01 and the second sample S02. This indicates that the in-plane magnetic anisotropy of the second magnetic layer 20 (a magnetization free layer) changes due to the inverse magnetostriction effect.

Figure 6A:
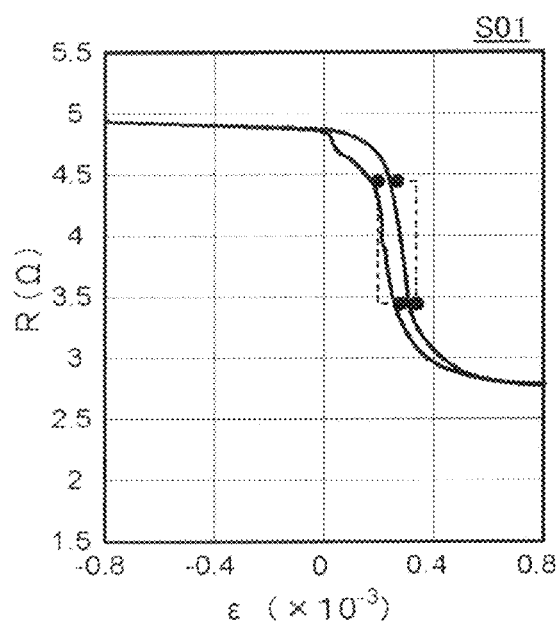
FIG. 6A and FIG. 6B are graphs showing characteristics of strain sensing elements.
Figure 6B:
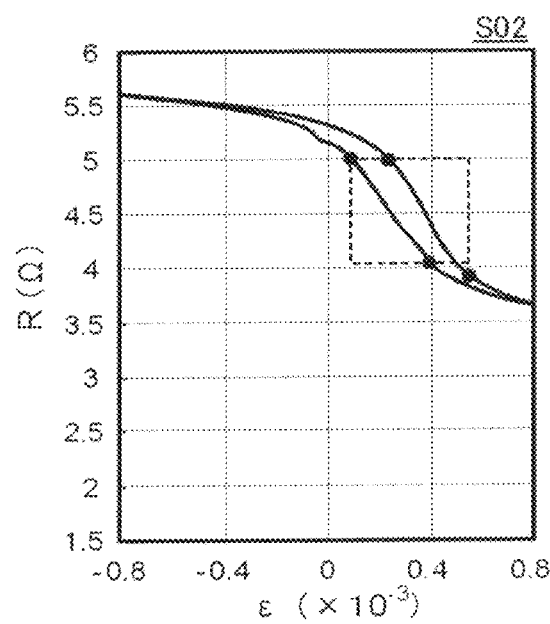

FIG. 6A and FIG. 6B are graphs illustrating characteristics of strain sensing elements.

FIG. 6A corresponds to the first sample S01, and FIG. 6B corresponds to the second sample S02. The drawings show the change in electric resistance R when the external magnetic field H is fixed and the strain $\epsilon$ is changed continuously in a range between $-0.8\times10^{-3}$ and $0.8\times10^{-3}$. The horizontal axis of the drawings is the strain $\epsilon$, and the vertical axis is the electric resistance R. The change in strain $\epsilon$ is both the change from $-0.8\times10^{-3}$ toward $0.8\times10^{-3}$ and the change from $0.8\times10^{-3}$ toward $-0.8\times10^{-3}$. The results show strain sensor characteristics. The gauge factor is calculated from the drawings.

The gauge factor GF is expressed by GF=(dR/R)/dε.

From FIG. 6A, the gauge factor in the first sample S01 is calculated to be 4027. From FIG. 6B, the gauge factor in the second sample S02 is calculated to be 895.

Thus, in the case where the same second magnetic layer 20 (a magnetization free layer of a $Co_{40}Fe_{40}B_{20}$ layer with a thickness of 4 nm) is used, the gauge factor can be significantly improved by using a Mg—O layer with a thickness of 1.5 nm as the functional layer 25.

On the other hand, the MR ratio of the first sample S01 is 149%. The MR ratio of the second sample S02 is 188%. The coercivity Hc of the first sample S01 is 3.2 Oe. The coercivity Hc of the second sample S02 is 27 Oe. The magnetostriction constant λ of the first sample S01 is 20 ppm. The magnetostriction constant λ of the second sample S02 is 30 ppm.

Such a difference in gauge factor dependent on the presence or absence of the functional layer 25 is presumed to be due to the fact that the coercivity Hc of the $Co_{40}Fe_{40}B_{20}$ layer that is the second magnetic layer 20 (a magnetization free layer) is different.

As mentioned above, the coercivity Hc of the second sample S02 is 27 Oe, whereas the coercivity Hc of the first sample S01 is 3.2 Oe. The coercivity Hc of the first sample S01 is very small. The improvement in gauge factor due to the decrease in coercivity Hc can be explained as follows.

As described in regard to FIG. 2A to FIG. 2C, when a strain is generated in a magnetization free layer (the second magnetic layer 20), the magnetization direction of the magnetization free layer changes due to the inverse magnetostriction effect. At this time, by using a magnetic material with a large magnetostriction constant λ as the magnetization free layer, the force of rotating magnetization works greatly with respect to the strain; therefore, the gauge factor can be improved. On the other hand, the gauge factor depends also on the coercivity of the magnetization free layer. The coercivity is a physical parameter reflecting the ease of magnetization rotation of the magnetization free layer. Materials with a large coercivity have a strong force of keeping the magnetization direction as it is. Therefore, in materials with a large coercivity, a change in magnetization direction due to the inverse magnetostriction effect is less likely to occur.

Thus, a high gauge factor is obtained when the magnetostriction constant λ is large in the magnetization free layer. A high gauge factor is obtained when the coercivity in the magnetization free layer is small.

As mentioned above, the value of the magnetostriction constant λ in the first sample S01 is relatively close to that in the second sample S02, and is sufficiently large. On the other hand, the coercivity Hc in the first S01 is significantly smaller than that in the second sample S02, and is approximately 1/10 of that. In the first sample S01, it is presumed that the effect of the reduction in coercivity Hc greatly contributes to the increase in gauge factor.

The small coercivity Hc and the large magnetostriction constant λ obtained in the first sample S01 are obtained by providing the Mg—O layer as the functional layer 25 on the second magnetic layer 20 (a magnetization free layer) of a $Co_{40}Fe_{40}B_{20}$ layer.

An investigation by the inventors of this application has revealed that the crystal structure of the $Co_{40}Fe_{40}B_{20}$ layer of the second magnetic layer 20 (a magnetization free layer) changes with the presence or absence of the functional layer 25. It has been found that the difference in crystal structure of $Co_{40}Fe_{40}B_{20}$ has relation to the difference in coercivity Hc. The difference in crystal structure will now be described.

FIG. 7A to FIG. 7D are microscope images illustrating characteristics of a strain sensing element.

Figure 7A:
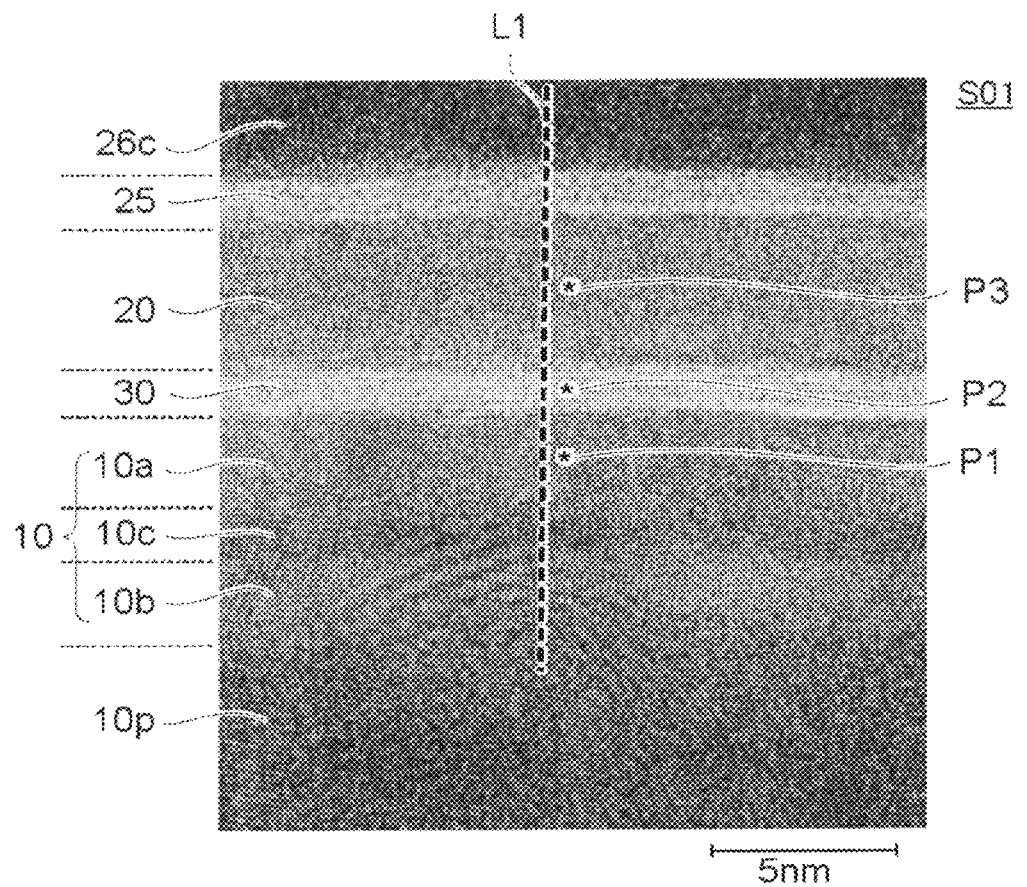
FIG. 7A to FIG. 7D are microscope images showing characteristics of a strain sensing element.

FIG. 7A is a cross-sectional transmission electron microscope (cross-sectional TEM) photographic image of the strain sensing element of the first sample S01. FIG. 7A is a photograph of the stacked structure of the first sample S01.

Figures 7B, 7C, 7D:
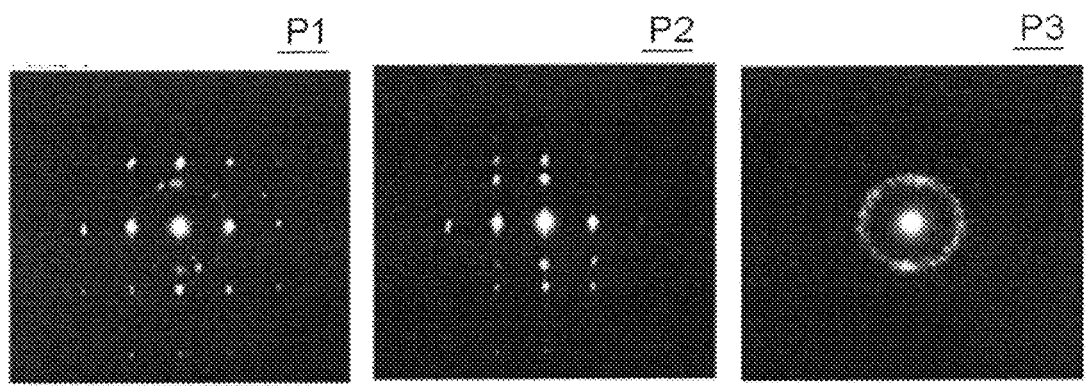

FIG. 7B to FIG. 7D are crystal lattice diffraction images obtained by nanodiffraction of an electron beam of points P1 to P3 of FIG. 7A, respectively.

FIG. 7A shows a region including a part of the second magnetization pinned layer 10b (a $Co_{50}Fe_{50}$ layer) to a part of the cap layer 26c (a Ru layer).

As can be seen from FIG. 7A, the first magnetization pinned layer 10a (a Co—Fe—B layer) includes a crystal portion. Also the spacer layer 30 (a Mg—O layer) is a crystal. On the other hand, in the most part of the second magnetic layer 20 (a Co—Fe—B layer that is a magnetization free layer) sandwiched by the spacer layer 30 and the functional layer 25 (a Mg—O layer), a regular atomic arrangement is not observed. That is, the second magnetic layer 20 is amorphous.

The crystal state can be checked by a crystal lattice diffraction image. The crystal lattice diffraction images of points P1 to P3 in FIG. 7A are shown in FIG. 7B to FIG. 7D, respectively. Point P1 corresponds to the first magnetization pinned layer 10a. Point P2 corresponds to the spacer layer 30. Point P3 corresponds to the second magnetic layer 20 (a magnetization free layer).

As shown in FIG. 7B, diffraction spots are observed in the diffraction image of point P1 corresponding to the first magnetization pinned layer 10a (a Co—Fe—B layer). The diffraction spots are due to the fact that the first magnetization pinned layer 10a has a crystal structure.

As shown in FIG. 7C, diffraction spots are observed in the diffraction image of point P2 corresponding to the spacer layer 30 (a Mg—O layer). The diffraction spots are due to the fact that the spacer layer 30 has a crystal structure.

On the other hand, as shown in FIG. 7D, distinct diffraction spots are not observed in the diffraction image of point P3 corresponding to the second magnetic layer 20 (a Co—Fe—B layer of a magnetization free layer). In the diffraction image, a ring-like diffraction image reflecting an amorphous structure is observed. The result shows that the second magnetic layer 20 (a Co—Fe—B layer of a magnetization free layer) of the first sample S01 includes an amorphous portion.

FIG. 8A to FIG. 8D are microscope images illustrating characteristics of a strain sensing element.

Figure 8A:
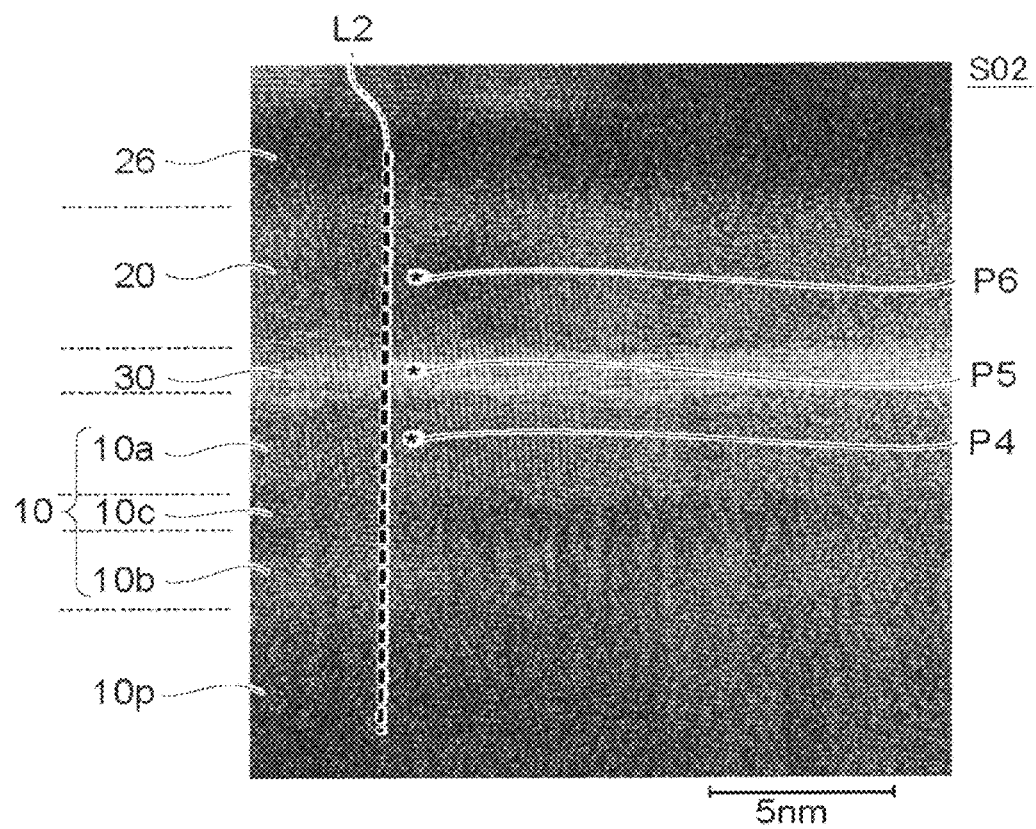
FIG. 8A to FIG. 8D are microscope images showing characteristics of a strain sensing element.
Figures 8B, 8C, 8D:
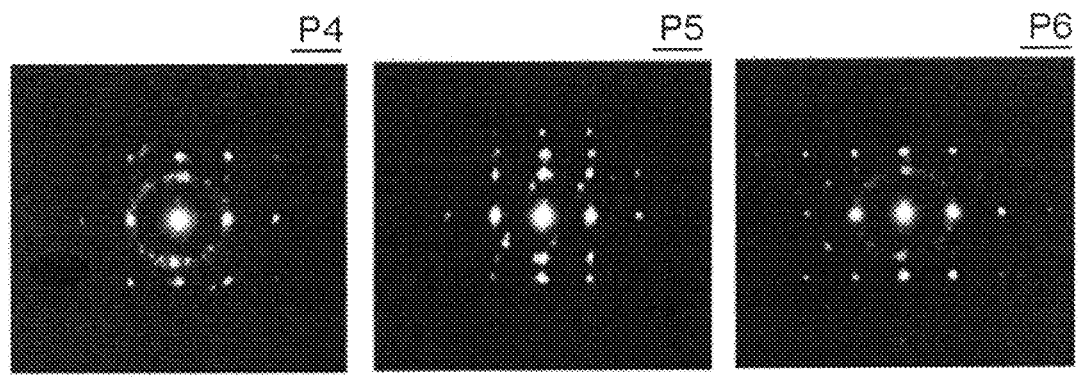

FIG. 8A is a cross-sectional transmission electron microscope (cross-sectional TEM) photographic image of the strain sensing element of the second sample S02. FIG. 8B to FIG. 8D are crystal lattice diffraction images obtained by nanodiffraction of an electron beam of points P4 to P6 of FIG. 8A, respectively.

As can be seen from FIG. 8A, the first magnetization pinned layer 10a (a Co—Fe—B layer) includes a crystal portion, and also the spacer layer 30 (a Mg—O layer) is a crystal. Also the second magnetic layer 20 (a Co—Fe—B layer that is a magnetization free layer) on the spacer layer 30 includes a large amount of crystal portions.

As shown in FIG. 8B, diffraction spots due to a crystal structure are found in the diffraction image of the first magnetization pinned layer 10a (a Co—Fe—B layer).

As shown in FIG. 8C, diffraction spots due to a crystal structure are found in the diffraction image of the spacer layer 30 (a Mg—O layer).

As shown in FIG. 8D, diffraction spots due to a crystal structure are found also in the diffraction image of the second magnetic layer 20 (a Co—Fe—B layer of a magnetization free layer). The result shows that the most part of the second magnetic layer 20 (a Co—Fe—B layer of a magnetization free layer) of the second sample S02 has a crystal structure.

As can be seen from FIG. 7A to FIG. 7D, the magnetization free layer of the first sample S01 showing a high gauge factor includes an amorphous structure. On the other hand, as can be seen from FIG. 8A to FIG. 8D, the magnetization free layer of the second sample S02 that has showed a low gauge factor has a crystal structure.

As described above, in each of the first sample S01 and the second sample S02, a $Co_{40}Fe_{40}B_{20}$ layer (4 nm) of the same composition is used as the magnetization free layer. In spite of this, the first sample S01 and the second sample S02 have different gauge factors and different crystal states. It is presumed that this reflects the presence or absence of the functional layer 25 provided on the magnetization free layer (a $Co_{40}Fe_{40}B_{20}$ layer (4 nm)).

The difference between the crystal states of the magnetization free layers of the first sample S01 and the second sample S02 is further described.

FIG. 9A, FIG. 9B, FIG. 10A, and FIG. 10B are schematic diagrams illustrating characteristics of strain sensing elements.

Figures 9A, 9B:
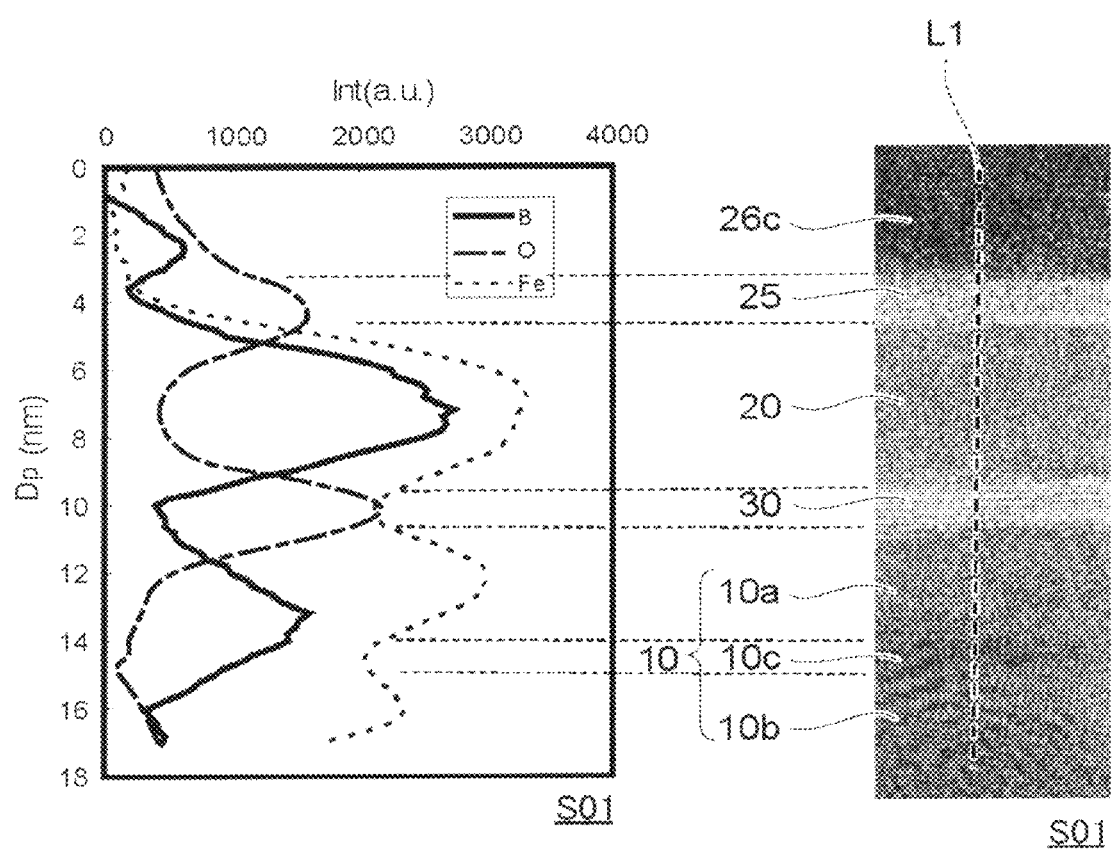
FIG. 9A and FIG. 9B, are schematic diagrams showing characteristics of strain sensing elements.
Figures 10A, 10B:
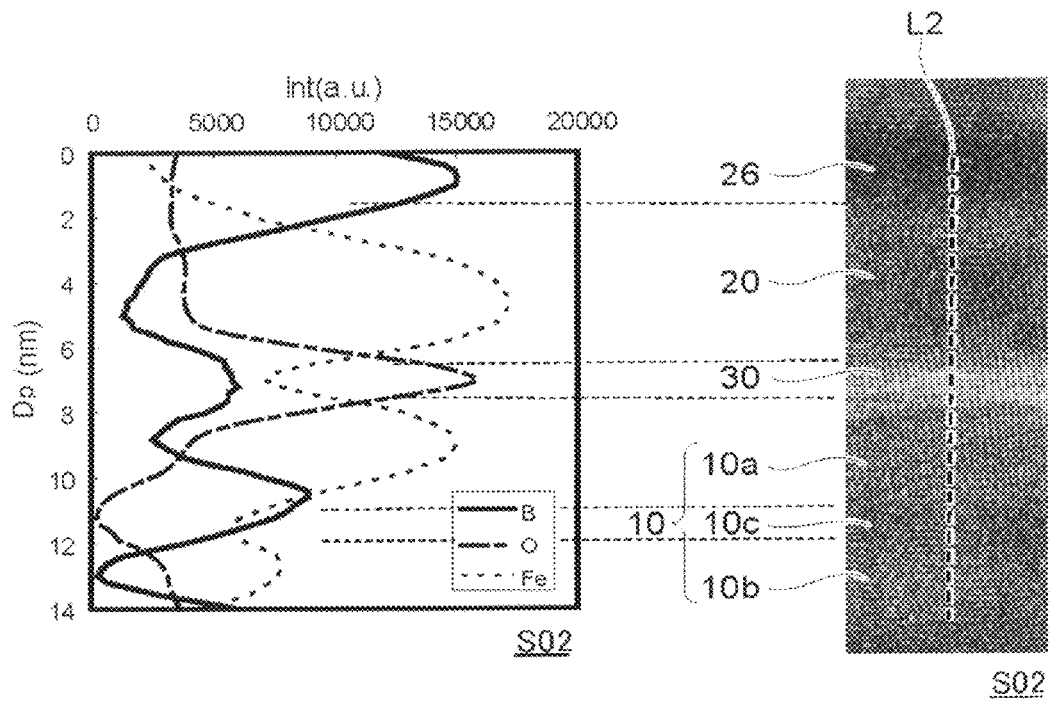
FIG. 10A and FIG. 10B are schematic diagrams showing characteristics of strain sensing elements.

FIG. 9B corresponds to part of FIG. 7A, and FIG. 10B corresponds to part of FIG. 8A.

FIG. 9A and FIG. 10A are the investigation results of the depth profile of elements of the samples obtained by electron energy-loss spectroscopy (EELS). FIG. 9A corresponds to the sample S01, and shows the depth profile of elements on line L1 shown in FIG. 7A. FIG. 10B corresponds to the second sample S02, and shows the depth profile of elements on line L2 shown in FIG. 8A. In these drawings, the horizontal axis is the intensity Int (an arbitrary unit) of detection of elements. The vertical axis is the depth Dp (nm). The depth Dp corresponds to the distance in the Z-axis direction, for example. These drawings show depth profiles regarding iron, boron, and oxygen.

As shown in FIG. 10A, in the second sample S02, the intensity Int of boron in the cap layer 26c is higher than the intensity Int of boron in the second magnetic layer 20 (a Co—Fe—B layer that is a magnetization free layer). In the second magnetic layer 20, the intensity Int of boron in a portion on the cap layer 26c side is higher than the intensity Int of boron in a central portion of the second magnetic layer 20. It is presumed that boron is diffused from the second magnetic layer 20 to the cap layer 26c side, and the concentration of boron in the second magnetic layer 20 is reduced.

On the other hand, as shown in FIG. 9A, in the first sample S01, a peak of boron appears in a central portion of the second magnetic layer 20 (a Co—Fe—B layer of a magnetization free layer). The boron content of the cap layer 26c is small. The boron concentration of the second magnetic layer 20 (a Co—Fe—B layer of a magnetization free layer) is hardly diffused to other layers, and maintains the initial state at the time of film formation.

From the foregoing, it is presumed that the functional layer (in this example, a Mg—O layer) provided on the second magnetic layer 20 (a magnetization free layer) has the effect of a diffusion barrier that suppresses the diffusion of boron from the second magnetic layer 20.

The above results suggest that the crystallization in the $Co_{40}Fe_{40}B_{20}$ layer of the second sample S02 in which the functional layer 25 is not provided proceeds more than that in the $Co_{40}Fe_{40}B_{20}$ layer of the first sample S01. That is, in the first sample S01, the $Co_{40}Fe_{40}B_{20}$ layer maintains the amorphous structure. On the other hand, crystallization has proceeded in the second sample S02 in which the functional layer 25 is not provided. The cause that crystallization is progressed in the second sample S02 is probably that boron of the magnetization free layer is diffused and the boron content of the magnetization free layer is reduced.

Figures 11A, 11B:
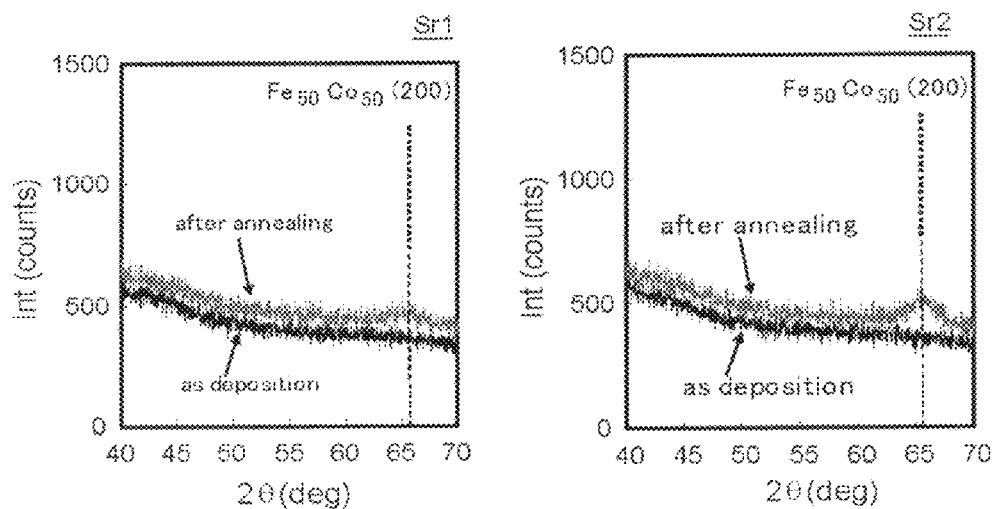
FIG. 11A and FIG. 11B are graphs showing characteristics of strain sensing elements.

FIG. 11A and FIG. 11B are graphs illustrating characteristics of strain sensing elements.

The drawings show the investigation results of X-ray diffraction of $Co_{40}Fe_{40}B_{20}$ layers. FIG. 11A and FIG. 11B correspond to the first sample S01 and the second sample S02, respectively. The horizontal axis of the drawings is the rotation angle 2θ (degrees). The vertical axis is the intensity Int.

It is difficult to obtain diffraction peaks of only the $Co_{40}Fe_{40}B_{20}$ layer in the sample in X-ray diffraction. Hence, the following model films are used in these samples. Sample Sr1 shown in FIG. 11A has a stacked structure of a first Mg—O layer (the spacer layer 30)/a $Co_{40}Fe_{40}B_{20}$ layer/a second Mg—O (the functional layer 25)/Ta (corresponding to the cap layer 26c). Sample Sr1 has the functional layer 25, and corresponds to the first sample S01. On the other hand, sample Sr2 shown in FIG. 11B has a stacked structure of a first Mg—O layer (the spacer layer 30)/a $Co_{40}Fe_{40}B_{20}$ layer/Ta (corresponding to the cap layer 26c). Sample Sr2 does not have the functional layer 25, and corresponds to the second sample S02.

In FIG. 11A and FIG. 11B, X-ray diffraction results after annealing of 320° C. and 1 H and before the annealing are shown for reference.

As can be seen from FIG. 11A and FIG. 11B, it is found that before annealing, no X-ray diffraction peak is found in either sample Sr1 or sample Sr2, and the magnetization free layers of both sample Sr1 and sample Sr2 are amorphous. On the other hand, after annealing, a diffraction peak of $Co_{50}Fe_{50}$ appears in sample Sr2 more strongly than in sample Sr1.

This means that the crystallization in the $Co_{40}Fe_{40}B_{20}$ layer of the second sample S02 in which the functional layer 25 is not provided has proceeded more than that in the $Co_{40}Fe_{40}B_{20}$ layer of the first sample S01. That is, in the first sample S01, the $Co_{40}Fe_{40}B_{20}$ layer maintains the amorphous structure even after annealing. On the other hand, in the second sample S02 in which the functional layer 25 is not provided, crystallization proceeds after annealing.

Figure 12A:
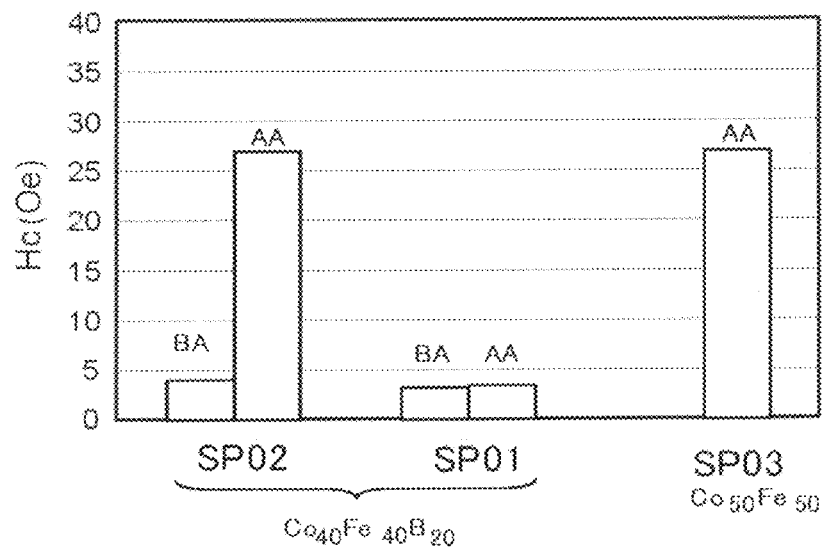
FIG. 12A and FIG. 12B are graphs showing characteristics of strain sensing elements.
Figure 12B:
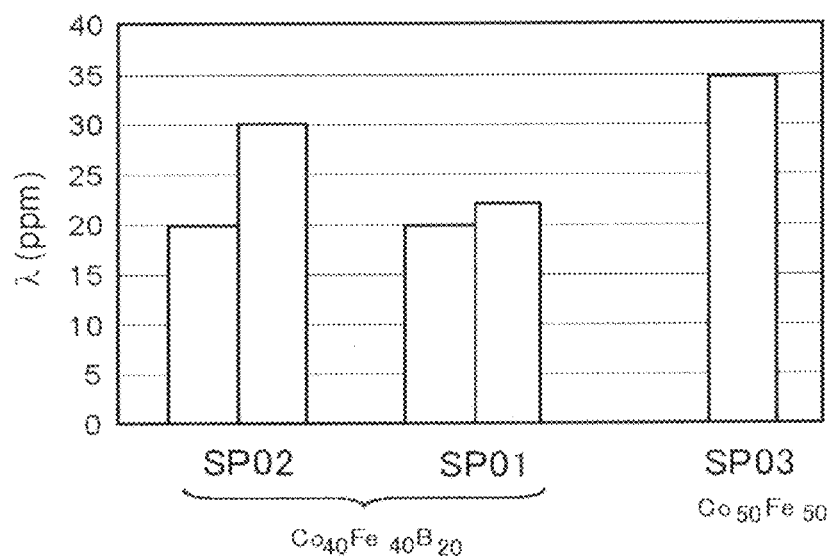

FIG. 12A and FIG. 12B are graphs illustrating characteristics of strain sensing elements.

The drawings show characteristics of the first sample S01 and the second sample S02 mentioned above and a third sample S03. In the third sample S03, $Fe_{50}Co_{50}$ (thickness: 4 nm) including no boron is used as the magnetization free layer. The third sample S03 has the same configuration as the second sample S02 except for the magnetization free layer.

FIG. 12A shows the coercivity (Oe). FIG. 12B shows the magnetostriction constant λ (ppm). For the first sample S01 and the second sample S02, values of before annealing (BA) and values after annealing (AA) are shown.

As shown in FIG. 8A, in the first sample S01 and the second sample S02 before annealing (BA), the coercivity Hc is approximately 3 Oe to 4 Oe. Good soft magnetic characteristics are exhibited before annealing (BA). However, before annealing (BA), the MR ratio is low and therefore a high gauge factor cannot be obtained.

In the second sample S02, the coercivity Hc increases to 27 Oe after annealing (AA). This value is almost equal to the value of the third sample S03 using a $Co_{50}Fe_{50}$ layer including no boron. The increase in coercivity Hc in the second sample S02 after annealing (AA) is due to the fact that crystallization proceeds in the second sample S02 after annealing (AA).

On the other hand, in the first sample S01, the coercivity Hc after annealing (AA) keeps the value before annealing (BA). This is due to the fact that in the first sample S01, crystallization does not proceed and the amorphous structure is maintained even after annealing (BA).

As shown in FIG. 8B, in the first sample S01, the magnetostriction constant λ after annealing (AA) substantially keeps the value before annealing (BA).

Figure 13:
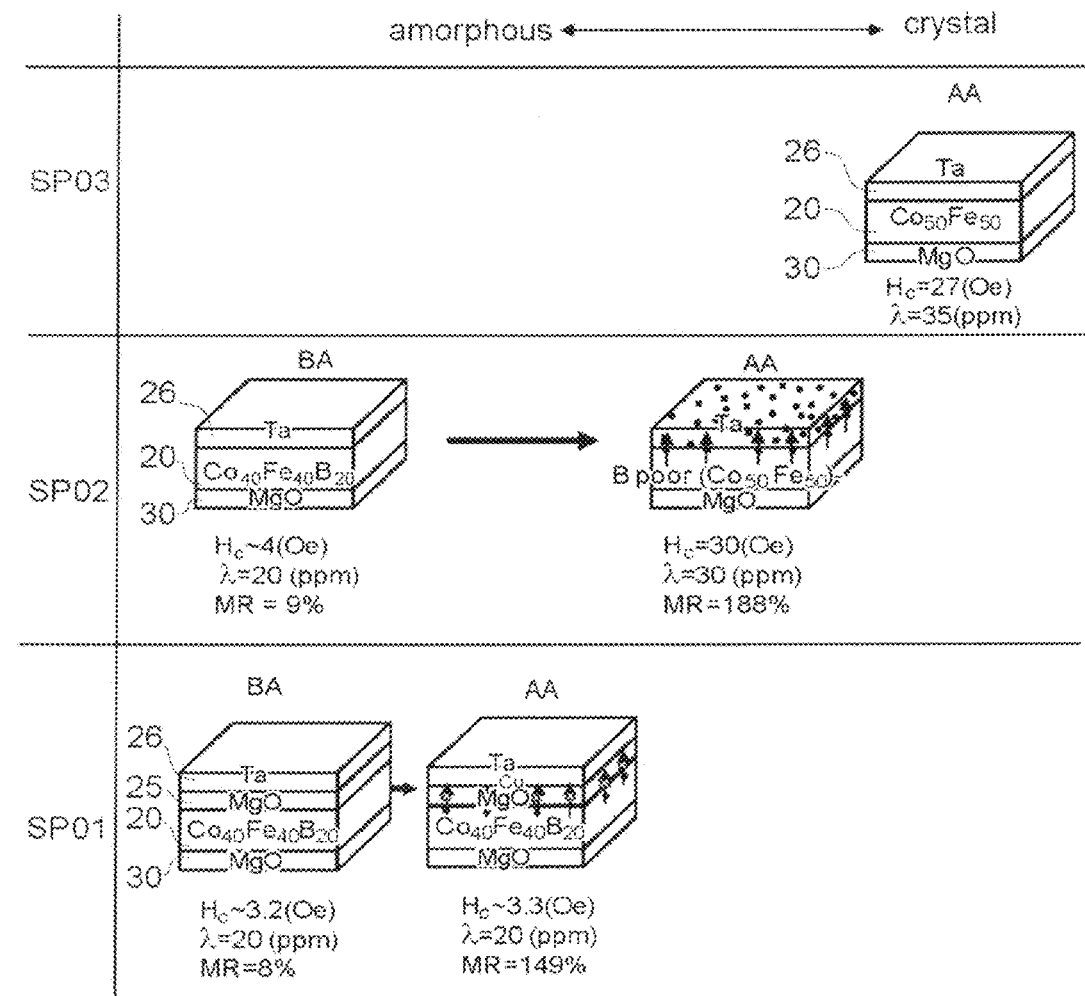
FIG. 13 is a schematic diagram showing characteristics of strain sensing elements.

FIG. 13 is a schematic diagram illustrating characteristics of strain sensing elements.

FIG. 13 shows characteristics of the first to third samples S01 to S03 mentioned above in a model way.

As shown in FIG. 13, the coercivity Hc of the $Co_{40}Fe_{40}B_{20}$ layer including a large amount of boron is small before annealing (the first sample S01 and the second sample S02). On the other hand, the $Co_{50}Fe_{50}$ layer including no boron has a large coercivity Hc.

In the second sample S02, boron of the $Co_{40}Fe_{40}B_{20}$ layer is diffused to the cap layer 26c side during annealing and the boron concentration is reduced; consequently, crystallization proceeds, and the coercivity Hc is increased to a level equal to that of the third sample S03. On the other hand, in the first sample S01, the diffusion of boron is suppressed by the functional layer 25, and the boron concentration in the $Co_{40}Fe_{40}B_{20}$ layer is maintained; thus, the progress of crystallization is suppressed. Consequently, even after annealing (AA), the coercivity Hc can be kept small at a level equal to that before annealing (BA). Consequently, in the first sample S01, a large magnetostriction constant λ of 20 ppm, a small coercivity Hc of approximately 3 Oe, and a high MR ratio of 149% are obtained. Thus, a high gauge factor of 4000 or more is obtained.

By combining the second magnetic layer 20 (a magnetization free layer) including boron and the functional layer 25 that suppresses the diffusion of boron in the above manner, even after annealing (AA), the boron content in the magnetization free layer can be maintained and the amorphous structure can be maintained.

Thus, in the embodiment, the second magnetic layer 20 including an amorphous portion and including boron and the functional layer 25 of at least one of an oxide and a nitride that suppresses the diffusion of boron are used. Thereby, a high-sensitivity strain sensing element can be provided.

Examples of the strain sensing element according to the embodiment will now be described.

For the first electrode E1 and the second electrode E2, at least one of aluminum (Al), aluminum-copper alloy (Al—Cu), copper (Cu), silver (Ag), and gold (Au) is used, for example. By using such a material with a relatively small electric resistance as the first electrode E1 and the second electrode E2, a current can be passed through the strain sensing element 51 efficiently. A nonmagnetic material may be used for the first electrode E1.

The first electrode E1 may include an underlayer (not shown) for the first electrode E1, a cap layer (not shown) for the first electrode E1, and a layer of at least one of Al, Al—Cu, Cu, Ag, and Au provided between them, for example. Tantalum (Ta)/copper (Cu)/tantalum (Ta) or the like is used as the first electrode E1, for example. By using Ta as the underlayer for the first electrode E1, the adhesion between the film unit 70 and the first electrode E1 is improved, for example. Also titanium (Ti), titanium nitride (TiN), or the like may be used as the underlayer for the first electrode E1.

By using Ta as the cap layer for the first electrode E1, the oxidation of copper (Cu) or the like under the cap layer can be prevented. Also titanium (Ti), titanium nitride (TiN), or the like may be used as the cap layer for the first electrode E1.

As the underlayer 10l, a stacked structure including a buffer layer (not shown) and a seed layer (not shown) may be used, for example. The buffer layer eases the roughness of the surface of the first electrode E1 or the film unit 70, and improves the crystallinity of a layer stacked on the buffer layer, for example. As the buffer layer, at least one selected from the group consisting of tantalum (Ta), titanium (Ti), vanadium (V), tungsten (W), zirconium (Zr), hafnium (Hf), and chromium (Cr) is used, for example. An alloy including at least one selected from these materials may be used as the buffer layer.

The thickness of the buffer layer of the underlayer 10l is preferably not less than 1 nm and not more than 10 nm. The thickness of the buffer layer is more preferably not less than 1 nm and not more than 5 nm. If the thickness of the buffer layer is too small, the buffer effect will be lost. If the thickness of the buffer layer is too large, the thickness of the strain sensing element 51 will be too large. The seed layer may be formed on the buffer layer, and may have buffer effect. In this case, the buffer layer may be omitted. A Ta layer with a thickness of 3 nm is used as the buffer layer, for example.

The seed layer of the underlayer 10l controls the crystal orientation of a layer stacked on the seed layer. The seed layer controls the crystal grain size of a layer stacked on the seed layer. A metal of the fcc structure (face-centered cubic structure), the hcp structure (hexagonal close-packed structure), or the bcc structure (body-centered cubic structure) or the like is used as the seed layer.

As the seed layer of the underlayer 10l, ruthenium (Ru) of the hcp structure, NiFe of the fcc structure, or Cu of the fcc structure may be used. Thereby, the crystal orientation of a spin valve film on the seed layer can be made the fcc(111) orientation, for example. A Cu layer with a thickness of 2 nm or a Ru layer with a thickness of 2 nm is used as the seed layer, for example. When it is attempted to enhance the crystal orientation properties of a layer formed on the seed layer, the thickness of the seed layer is preferably not less than 1 nm and not more than 5 nm. The thickness of the seed layer is more preferably not less than 1 nm and not more than 3 nm. Thereby, the function as a seed layer of improving the crystal orientation is exhibited sufficiently.

On the other hand, when it is not necessary to provide a crystal orientation to a layer provided on the seed layer (for example, when an amorphous magnetization free layer is formed, etc.), the seed layer may be omitted, for example. A Ru layer with a thickness of 2 nm is used as the seed layer, for example.

The pinning layer 10p provides unidirectional anisotropy to the first magnetic layer 10 (a ferromagnetic layer) formed on the pinning layer 10p, and fixes the magnetization 10m of the first magnetic layer 10, for example. An antiferromagnetic layer is used as the pinning layer 10p, for example. At least one selected from the group consisting of Ir—Mn, Pt—Mn, Pd—Pt—Mn, and Ru—Rh—Mn is used for the pinning layer 10p, for example. The thickness of the pinning layer 10p is appropriately set to provide unidirectional anisotropy of a sufficient strength.

When PtMn or PdPtMn is used as the pinning layer 10p, the thickness of the pinning layer 10p is preferably not less than 8 nm and not more than 20 nm. The thickness of the pinning layer 10p is more preferably not less than 10 nm and not more than 15 nm. When IrMn is used as the pinning layer 10p, unidirectional anisotropy can be provided by a smaller thickness than when PtMn is used as the pinning layer 10p. In this case, the thickness of the pinning layer 10p is preferably not less than 4 nm and not more than 18 nm. The thickness of the pinning layer 10p is more preferably not less than 5 nm and not more than 15 nm. An $Ir_{22}Mn_{78}$ layer with a thickness of 7 nm is used as the pinning layer 10p, for example.

A hard magnetic layer may be used as the pinning layer 10p. As the hard magnetic layer, CoPt (the ratio of Co being not less than 50 at. % and not more than 85 at. %), $(Co_xPt_{100-x})_{100-y}Cr_y$ (x being not less than 50 at. % and not more than 85 at. %, y being not less than 0 at. % and not more than 40 at. %), FePt (the ratio of Pt being not less than 40 at. % and not more than 60 at. %), or the like may be used, for example.

As the second magnetization pinned layer 10b, $Co_xFe_{100-x}$ alloy (x being not less than 0 at. % and not more than 100 at. %), $Ni_xFe_{100-x}$ alloy (x being not less than 0 at. % and not more than 100 at. %), or a material in which a nonmagnetic element is added to these is used, for example. As the second magnetization pinned layer 10b, at least one selected from the group consisting of Co, Fe, and Ni is used, for example. As the second magnetization pinned layer 10b, an alloy including at least one material selected from these materials may be used. As the second magnetization pinned layer 10b, $(Co_xFe_{100-x})_{100-y}B_y$ alloy (x being not less than 0 at. % and not more than 100 at. %, y being not less than 0 at. % and not more than 30 at. %) may be used. By using an amorphous alloy of $(Co_xFe_{100-x})_{100-y}B_y$ as the second magnetization pinned layer 10b, the variation in characteristics of the strain sensing element 51 can be suppressed even when the size of the strain sensing element 51 is small.

The thickness of the second magnetization pinned layer 10b is preferably not less than 1.5 nm and not more than 5 nm, for example. Thereby, the strength of the unidirectional anisotropic magnetic field caused by the pinning layer 10p can be increased, for example. The strength of the antiferromagnetic coupling magnetic field between the second magnetization pinned layer 10b and the first magnetization pinned layer 10a can be increased via the magnetic coupling layer 10c formed on the second magnetization pinned layer 10b, for example. The magnetic thickness (the product of the saturation magnetization Bs and the thickness t (Bs·t)) of the second magnetization pinned layer 10b is preferably substantially equal to the magnetic thickness of the first magnetization pinned layer 10a, for example.

The saturation magnetization of $Co_{40}Fe_{40}B_{20}$ in a thin film form is approximately 1.9 T (tesla). When a $Co_{40}Fe_{40}B_{20}$ layer with a thickness of 3 nm is used as the first magnetization pinned layer 10a, the magnetic thickness of the first magnetization pinned layer 10a is 1.9 T×3 nm, which is 5.7 T nm, for example. On the other hand, the saturation magnetization of $Co_{75}Fe_{25}$ is approximately 2.1 T. The thickness of the second magnetization pinned layer 10b by which a magnetic thickness equal to the above is obtained is 5.7 T nm/2.1 T, which is 2.7 nm. In this case, a $Co_{75}Fe_{25}$ layer with a thickness of approximately 2.7 nm is preferably used as the second magnetization pinned layer 10b. A $Co_{75}Fe_{25}$ layer with a thickness of 2.5 nm is used as the second magnetization pinned layer 10b, for example.

In the strain sensing element 51, a synthetic pin structure composed of the second magnetization pinned layer 10b, the magnetic coupling layer 10c, and the first magnetization pinned layer 10a is used as the first magnetic layer 10. A single pin structure formed of one magnetization pinned layer may be used as the first magnetic layer 10. In the case where a single pin structure is used, a $Co_{40}Fe_{40}B_{20}$ layer with a thickness of 3 nm is used as the magnetization pinned layer, for example. The same material as the material of the second magnetization pinned layer 10b described above may be used as the ferromagnetic layer used as the magnetization pinned layer of the single pin structure.

The magnetic coupling layer 10c produces an antiferromagnetic coupling between the second magnetization pinned layer 10b and the first magnetization pinned layer 10a. The magnetic coupling layer 10c forms a synthetic pin structure. Ru is used as the magnetic coupling layer 10c, for example. The thickness of the magnetic coupling layer 10c is preferably not less than 0.8 nm and not more than 1 nm, for example. Other materials than Ru may be used as the magnetic coupling layer 10c to the extent that they produce a sufficient antiferromagnetic coupling between the second magnetization pinned layer 10b and the first magnetization pinned layer 10a. The thickness of the magnetic coupling layer 10c may be set to a thickness of not less than 0.8 nm and not more than 1 nm corresponding to the second peak (2nd peak) of the RKKY (Ruderman-Kittel-Kasuya-Yosida) coupling. The thickness of the magnetic coupling layer 10c may be set to a thickness of not less than 0.3 nm and not more than 0.6 nm corresponding to the first peak (1st peak) of the RKKY coupling. Ru with a thickness of 0.9 nm is used as the magnetic coupling layer 10c, for example. Thereby, a highly reliable coupling is obtained more stably.

The magnetic layer used as the first magnetization pinned layer 10a directly contributes to the MR effect. Co—Fe—B alloy is used as the first magnetization pinned layer 10a, for example. Specifically, $(Co_xFe_{100-x})_{100-y}B_y$ alloy (x being not less than 0 at. % and not more than 100 at. %, y being not less than 0 at. % and not more than 30 at. %) may be used as the first magnetization pinned layer 10a. When an amorphous alloy of $(Co_xFe_{100-x})_{100-y}B_y$ is used as the first magnetization pinned layer 10a, the variation between elements due to crystal grains can be suppressed even when the size of the strain sensing element 51 is small, for example.

A layer (for example, a tunnel insulating layer (not shown)) formed on the first magnetization pinned layer 10a may be planarized. By the planarization of the tunnel insulating layer, the defect density of the tunnel insulating layer can be reduced. Thereby, a larger MR ratio is obtained with a lower resistance-area product (RA). When Mg—O is used as the material of the tunnel insulating layer, an amorphous alloy of $(Co_xFe_{100-x})_{100-y}B_y$ may be used as the first magnetization pinned layer 10a; thereby, the (100) orientation properties of the Mg—O layer formed on the tunnel insulating layer can be enhanced, for example. By enhancing the (100) orientation properties of the MgO layer, a larger MR ratio is obtained. The $(Co_xFe_{100-x})_{100-y}B_y$ alloy is crystallized during annealing, with the (100) plane of the Mg—O layer as a template. Thus, good crystal matching between the Mg—O and the $(Co_xFe_{100-x})_{100-y}B_y$ alloy is obtained. By obtaining good crystal matching, a larger MR ratio is obtained.

As the first magnetization pinned layer 10a, Fe—Co alloy may be used as well as Co—Fe—B alloy, for example.

When the first magnetization pinned layer 10a is thicker, a larger MR ratio is obtained. To obtain a larger fixed magnetic field, the first magnetization pinned layer 10a is preferably thinner. Between the MR ratio and the fixed magnetic field, there is a trade-off in the thickness of the first magnetization pinned layer 10a. When Co—Fe—B alloy is used as the first magnetization pinned layer 10a, the thickness of the first magnetization pinned layer 10a is preferably not less than 1.5 nm and not more than 5 nm. The thickness of the first magnetization pinned layer 10a is more preferably not less than 2.0 nm and not more than 4 nm.

For the first magnetization pinned layer 10a, $Co_{90}Fe_{10}$ alloy of the fcc structure, Co of the hcp structure, or a Co alloy of the hcp structure is used as well as the material described above. As the first magnetization pinned layer 10a, at least one selected from the group consisting of Co, Fe, and Ni is used, for example. As the first magnetization pinned layer 10a, an alloy including at least one material selected from these materials is used. As the first magnetization pinned layer 10a, an FeCo alloy material of the bcc structure, a Co alloy with a cobalt content of 50 at. % or more, or a material with a Ni content of 50 at. % or more (a Ni alloy) may be used; thereby, a larger MR ratio is obtained, for example.

As the first magnetization pinned layer 10a, a Heusler magnetic alloy layer of $Co_2MnGe$, $Co_2FeGe$, $Co_2MnSi$, $Co_2FeSi$, $Co_2MnAl$, $Co_2FeAl$, $Co_2MnGa_{0.5}Ge_{0.5}$, $Co_2FeGa_{0.5}Ge_{0.5}$, and the like may be used, for example. As the first magnetization pinned layer 10a, a $Co_{40}Fe_{40}B_{20}$ layer with a thickness of 3 nm is used, for example.

The spacer layer 30 cuts the magnetic coupling between the first magnetic layer 10 and the second magnetic layer 20, for example. A metal, an insulator, or a semiconductor is used for the spacer layer 30, for example. Cu, Au, Ag, or the like is used as the metal, for example. In the case where a metal is used as the spacer layer 30, the thickness of the spacer layer 30 is approximately not less than 1 nm and not more than 7 nm, for example. As the insulator or the semiconductor, a magnesium oxide (Mg—O etc.), an aluminum oxide ($Al_2O_3$ etc.), a titanium oxide (Ti—O etc.), a zinc oxide (Zn—O etc.), a gallium oxide (Ga—O), or the like is used, for example. In the case where an insulator or a semiconductor is used as the spacer layer 30, the thickness of the spacer layer 30 is approximately not less than 0.6 nm and not more than 2.5 nm, for example. A CCP (currentconfined-path) spacer layer may be used as the spacer layer 30, for example. In the case where a CCP spacer layer is used as the spacer layer, a structure is used in which a copper (Cu) metal path is formed in an insulating layer of aluminum oxide ($Al_2O_3$), for example. A Mg—O layer with a thickness of 1.6 nm is used as the spacer layer 30, for example.

For the second magnetic layer 20, a ferromagnetic material is be used. In the embodiment, a high gauge factor can be obtained by using a ferromagnetic material of an amorphous structure including boron as the second magnetic layer 20. For the second magnetic layer 20, an alloy including at least one element selected from the group consisting of Fe, Co, and Ni and boron (B) may be used. For the second magnetic layer 20, Co—Fe—B alloy, Fe—B alloy, Fe—Co—Si—B alloy, or the like may be used, for example. For the second magnetic layer 20, an alloy including at least one element selected from the group consisting of Fe, Co, and Ni and boron (B) may be used. As the second magnetic layer 20, a $Co_{40}Fe_{40}B_{20}$ layer with a thickness of 4 nm may be used, for example.

The second magnetic layer 20 may have a multiple-layer structure. The second magnetic layer 20 may have a two-layer structure, for example. When a tunnel insulating layer of Mg—O is used as the spacer layer 30, it is preferable that a layer of Co—Fe—B alloy or Fe—B alloy be provided in a portion in contact with the spacer layer 30 of the second magnetic layer 20. Thereby, a high magnetoresistance effect is obtained.

The second magnetic layer 20 includes a first portion on the spacer layer 30 side and a second portion on the functional layer 25 side, for example. The first portion includes a portion in contact with the spacer layer 30 of the second magnetic layer 20, for example. A layer of Co—Fe—B alloy is used as the first portion. Fe—B alloy is used for the second portion, for example. That is, Co—Fe—B/Fe—B alloy is used as the second magnetic layer 20, for example. The thickness of the $Co_{40}Fe_{40}B_{20}$ layer is 0.5 nm, for example. The thickness of the Fe—B alloy layer mentioned above used as the second magnetic layer 20 is 6 nm, for example.

In the embodiment, a high gauge factor can be obtained by using a ferromagnetic material including boron and including an amorphous portion as the second magnetic layer 20. Examples of the material that may be used for the second magnetic layer 20 are described later.

In the embodiment, an oxide or a nitride may be used for the functional layer 25. A Mg—O layer with a thickness of 1.5 nm may be used as the functional layer 25, for example. In the embodiment, by using an oxide layer or a nitride layer as the functional layer 25, the diffusion of boron included in the second magnetic layer 20 is suppressed, for example. Thereby, the amorphous structure in the second magnetic layer 20 can be maintained. Consequently, a high gauge factor can be obtained. Examples of the material that may be used for the functional layer 25 are described later.

The cap layer 26c protects a layer provided under the cap layer 26c. A plurality of metal layers are used as the cap layer 26c, for example. A two-layer structure of a Ta layer and a Ru layer (Ta/Ru) is used as the cap layer 26c, for example. The thickness of the Ta layer is 1 nm, for example, and the thickness of the Ru layer is 5 nm, for example. Other metal layers may be provided as the cap layer 26c in place of the Ta layer and the Ru layer. The configuration of the cap layer 26c is arbitrary. A nonmagnetic material may be used as the cap layer 26c, for example. Other materials may be used as the cap layer 26c to the extent that they can protect a layer provided under the cap layer 26c.

Examples of the configuration and material of the second magnetic layer 20 (a magnetization free layer) are further described.

For the second magnetic layer 20, an alloy including at least one element selected from Fe, Co, and Ni and boron (B) may be used. Co—Fe—B alloy, Fe—B alloy, or the like may be used for the second magnetic layer 20, for example. $(Co_xFe_{100-x})_{100-y}B_y$ alloy (x being not less than 0 at. % and not more than 100 at. %, y being larger than 0 at. % and not more than 40 at. %) may be used for the second magnetic layer 20, for example. A $Co_{40}Fe_{40}B_{20}$ layer with a thickness of 4 nm may be used as the second magnetic layer 20, for example.

In the case where an alloy including at least one element selected from the group consisting of Fe, Co, and Ni and boron (B) is used for the second magnetic layer 20, at least one of Ga, Al, Si, and W may be added as an element that facilitates the increase in magnetostriction constant λ. Fe—Ga—B alloy, Fe—Co—Ga—B alloy, or Fe—Co—Si—B alloy may be used as the second magnetic layer 20, for example.

When $Fe_{1-y}B_y$ (0<y≤0.3) or $(Fe_aX_{1-a})_{1-y}B_y$ (X being Co or Ni; 0.8≤a<1, 0<y≤0.3) is used as at least part of the second magnetic layer 20, a large magnetostriction constant λ and a low coercivity are well balanced easily; thus, this case is particularly preferable. An $Fe_{80}B_{20}$ layer with a thickness of 4 nm may be used, for example.

The second magnetic layer 20 includes an amorphous portion as mentioned above. Part of the second magnetic layer 20 may be crystallized. The second magnetic layer 20 may include both a crystallized portion and an amorphous portion.

The magnetostriction constant λ and the coercivity Hc in the magnetization free layer are summable properties in accordance with the volume ratio of the ferromagnetic material included in the magnetization free layer. Even when a crystallized portion exists in the magnetization free layer, a small coercivity Hc can be obtained because the magnetic properties of the amorphous portion are obtained. In the case where a tunneling magnetoresistance effect using an insulator for the spacer layer 30 is used, it is preferable that a portion including the interface with the spacer layer 30 of the second magnetic layer 20 be crystallized, for example. Thereby, a high MR ratio is obtained, for example.

The boron concentration (for example, the composition ratio of boron) in the second magnetic layer 20 is preferably 5 at. % (atomic percent) or more. Thereby, it becomes easy to obtain an amorphous structure. The boron concentration in the second magnetic layer 20 is preferably 35 at. % or less. If the boron concentration is too high, the magnetostriction constant is reduced, for example. The boron concentration in the second magnetic layer 20 is preferably not less than 5 at. % and not more than 35 at. %, and more preferably not less than 10 at. % and not more than 30 at. %, for example.

The second magnetic layer 20 includes a first portion on the spacer layer 30 side and a second portion on the functional layer 25 side, for example. The first portion includes a portion in contact with the spacer layer 30 of the second magnetic layer 20, for example. A layer of Co—Fe—B alloy is used as the first portion. Fe—Ga—B alloy is used for the second portion, for example. That is, Co—Fe—B/Fe—Ga—B alloy is used as the second magnetic layer 20, for example. The thickness of the $Co_{40}Fe_{40}B_{20}$ layer is 2 nm, for example. The thickness of the Fe—Ga—B layer is 6 nm, for example. Also Co—Fe—B/Fe—B alloy may be used. The thickness of the $Co_{40}Fe_{40}B_{20}$ is 0.5 nm, for example. The thickness of the Fe—B is 4 nm, for example. As described above, Co—Fe—B/Fe—B alloy may be used as the second magnetic layer 20, for example. In this case, the thickness of the $Co_{40}Fe_{40}B_{20}$ layer is 0.5 nm, for example. The thickness of the Fe—B layer is 4 nm, for example. Thus, a high MR ratio can be obtained by using Co—Fe—B alloy for the first portion on the spacer layer 30 side.

Crystallized $Fe_{50}Co_{50}$ (thickness: 0.5 nm) may be used for the first portion including the interface with the spacer layer 30 of the second magnetic layer 20. A two-layer structure such as crystallized $Fe_{50}Co_{50}$ (thickness: 0.5 nm)/$Co_{40}Fe_{40}B_{20}$ (thickness: 2 nm) may be used as the first portion including the interface with the spacer layer 30 of the second magnetic layer 20.

Also a stacked film of $Fe_{50}Co_{50}$ (thickness: 0.5 nm)/$Co_{40}Fe_{40}B_{20}$ (thickness: 4 nm) may be used as the second magnetic layer 20. Also a stacked film of $Fe_{50}Co_{50}$ (thickness: 0.5 nm)/$Co_{40}Fe_{40}B_{20}$ (thickness: 2 nm)/$Co_{35}Fe_{35}B_{30}$ (thickness: 4 nm) may be used as the second magnetic layer 20. In this stacked film, the boron concentration increases with distance from the spacer layer 30.

Figure 14:
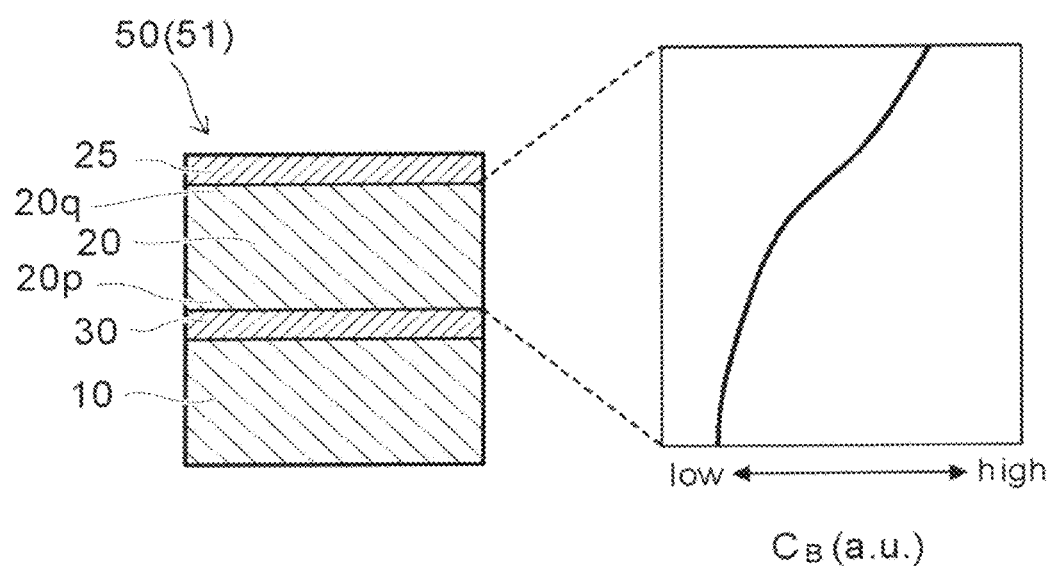
FIG. 14 is a schematic diagram showing the strain sensing element according to the first embodiment.

FIG. 14 is a schematic diagram illustrating the strain sensing element according to the first embodiment.

FIG. 14 illustrates the distribution of boron concentration in the strain sensing element 50 (the strain sensing element 51) according to the embodiment.

As shown in FIG. 14, the second magnetic layer 20 includes a first portion 20p and a second portion 20q. The first portion 10p is provided between the spacer layer 30 and the second portion 20q. The first portion 20p includes a portion in contact with the spacer layer 30 of the second magnetic layer 20, for example. The second portion 20q includes a portion in contact with the functional layer 25 of the second magnetic layer 20, for example.

As shown in FIG. 14, by reducing the boron concentration $C_B$ of the first portion 20p of the second magnetic layer 20 (a portion on the spacer layer 30 side), the MR ratio in the first portion 20p can be improved. Thereby, the change in electric resistance R with respect to the change in magnetization direction can be increased, and a high gauge factor can be obtained. On the other hand, by increasing the boron concentration $C_B$ in the second portion 20q (a portion away from the spacer layer 30), the coercivity Hc can be reduced in the second portion 20q, and the coercivity Hc of the whole second magnetic layer 20 can be reduced.

In the case where a tunneling magnetoresistance effect using Mg—O or the like for the spacer layer is used, the MR ratio depends on the composition and crystal structure of the magnetic material with a thickness of approximately 0.5 nm in contact with the spacer layer. In other words, the MR ratio is determined only by the magnetic layer near the spacer layer. On the other hand, in the case where the magnetization free layer is a stacked film, features in accordance with the thickness of the layers included in the stacked film, for example features of the thickest layer, are reflected most strongly in the magnetic properties such as magnetostriction and coercivity. This is because the stacked body of the magnetic materials included in the magnetization free layer is exchange-coupled and averaged. In the embodiment, a layer of a magnetic material having crystallinity is provided near the spacer layer, for example. Thereby, a high MR ratio is obtained. On the other hand, a layer of an amorphous magnetic material including boron is provided in the second portion 20q not in contact with the spacer layer. Thereby, a low coercivity is obtained. Thus, a low coercivity can be obtained as well as a high MR ratio.

Information on such a distribution of boron concentration $C_B$ is obtained by SIMS analysis (secondary ion mass spectrometry), for example. This information is obtained by the combination of cross-sectional TEM and EELS. This information is obtained by EELS analysis. This information is obtained also by three-dimensional atom probe analysis.

The thickness of the first portion 20p (a portion with a relatively high level of crystallization) is smaller than the thickness of the second portion 20q (a portion with a relatively low level of crystallization, an amorphous portion), for example. Thereby, it becomes easy to obtain a small coercivity Hc, for example. The thickness of the first portion 20p is not more than ⅓ of the thickness of the second portion 20q, for example.

A fourth sample S04 will now be described. In the fourth sample S04, the boron concentration in the first portion 20p of the second magnetic layer 20 is set lower than the boron concentration in the second portion 20q.

The material and thickness of the layers included in the fourth sample S04 are as follows:

The underlayer 10l: Ta (1 nm)/Ru (2 nm)
The pinning layer 10p: $Ir_{22}Mn_{78}$ (7 nm)
The second magnetization pinned layer 10b: $Co_{75}Fe_{25}$ (2.5 nm)
The magnetic coupling layer 10c: Ru (0.9 nm)
The first magnetization pinned layer 10a: $Co_{40}Fe_{40}B_{20}$ (3 nm)
The spacer layer 30: Mg—O (1.6 nm)
The second magnetic layer 20: $Co_{50}Fe_{50}$ (0.5 nm)/$Co_{40}Fe_{40}B_{20}$ (8 nm)
The functional layer 25: Mg—O (1.5 nm)
The cap layer 26c: Cu (1 nm)/Ta (2 nm)/Ru (5 nm)

In the fourth sample S04, $Co_{50}Fe_{50}$ (0.5 nm)/$Co_{40}Fe_{40}B_{20}$ (8 nm) is used as the magnetization free layer, and the first portion 20p with a low boron concentration and the second portion 20q with a high boron concentration are provided in the magnetization free layer.

Investigation results of the fourth sample S04 will now be described.

Figure 15:
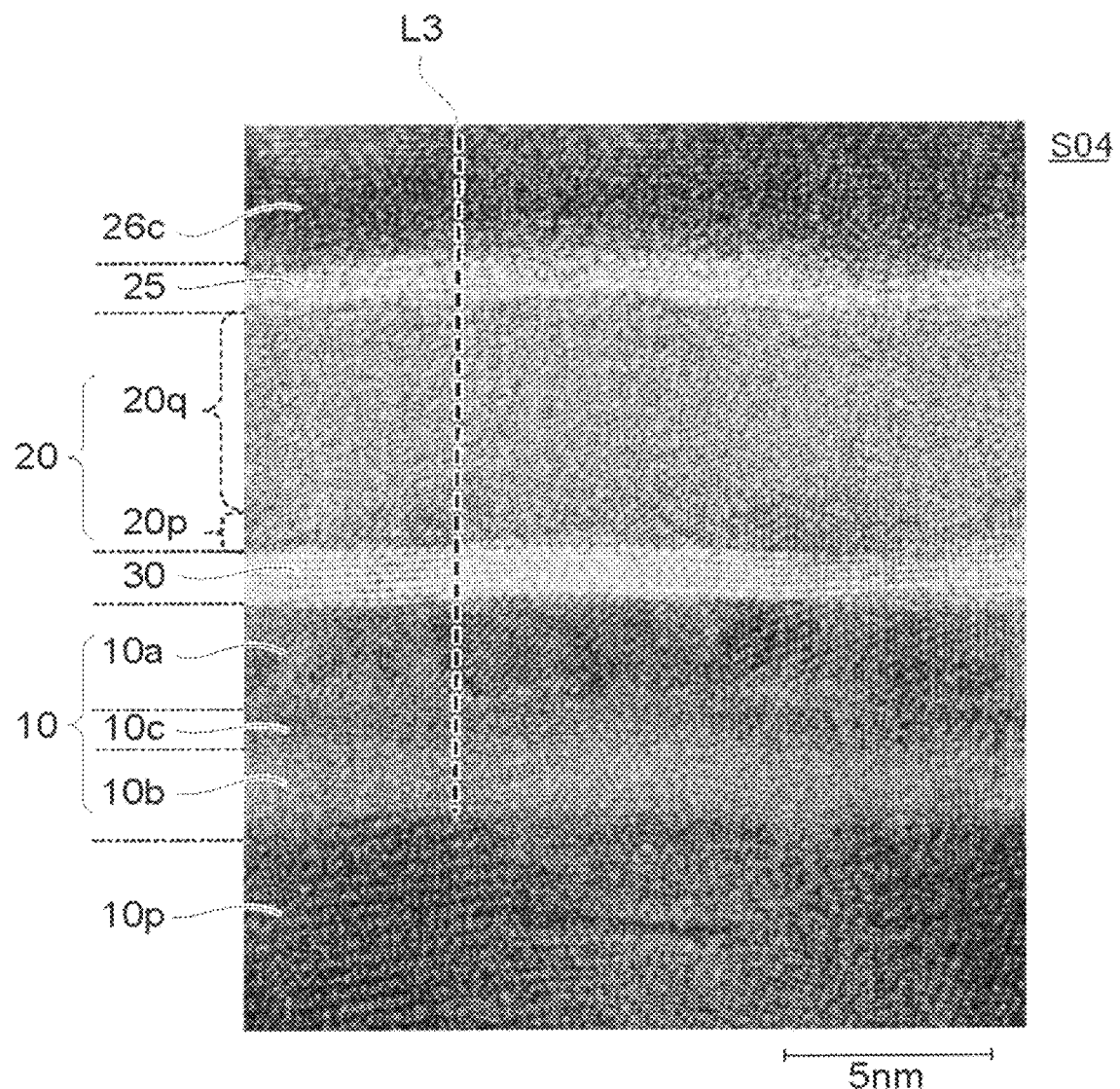
FIG. 15 is a microscope photographic image showing characteristics of a strain sensing element.

FIG. 15 is a microscope photographic image illustrating characteristics of a strain sensing element.

FIG. 15 is a cross-sectional transmission electron microscope photographic image of the strain sensing element of the fourth sample S04.

As can be seen from FIG. 15, in the second magnetic layer 20, the first portion 20p on the spacer layer 30 side has a crystal structure. It is found that the second portion 20q on the functional layer 25 side has an amorphous structure.

Figures 16A, 16B:
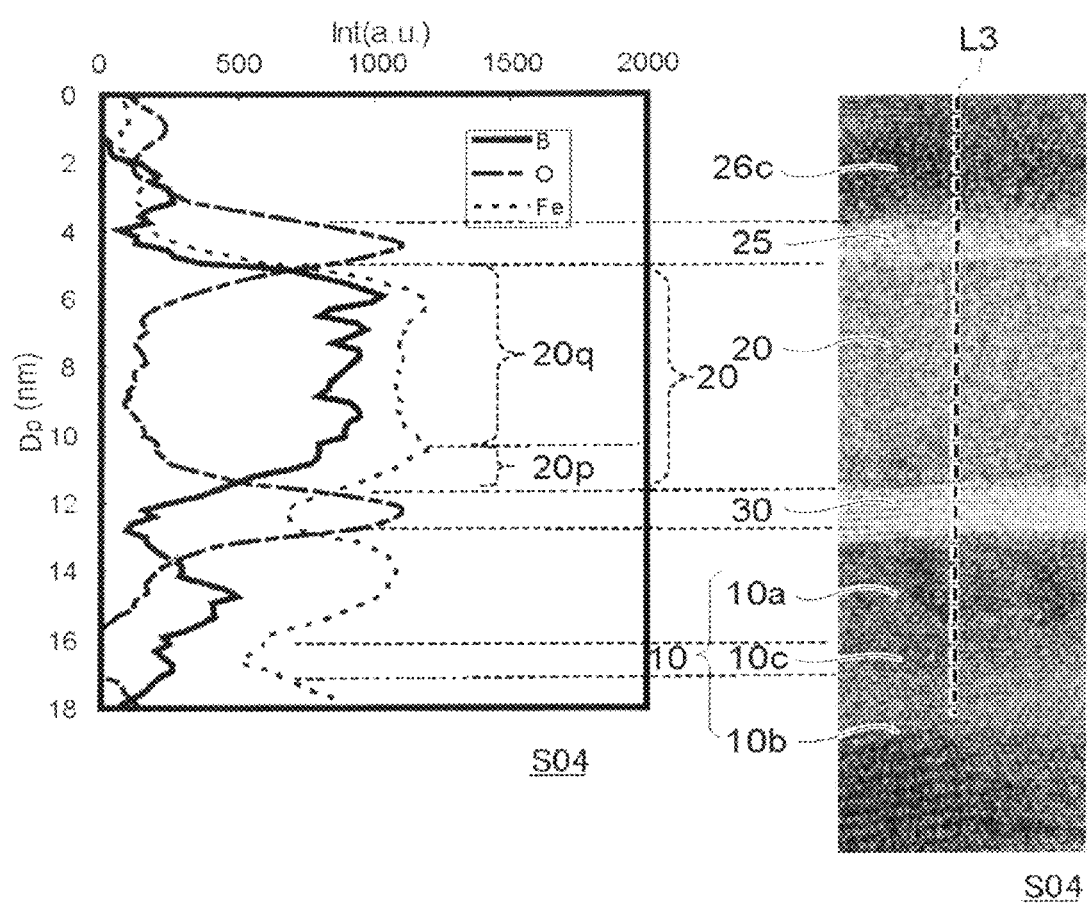
FIG. 16A and FIG. 16B are schematic diagrams showing characteristics of the strain sensing element.

FIG. 16A and FIG. 16B are schematic diagrams illustrating characteristics of the strain sensing element.

FIG. 16B corresponds to part of FIG. 15A.

FIG. 16A is investigation results of the depth profile of elements of the fourth sample S04 obtained by EELS. FIG. 16A shows the depth profile of elements on line L3 shown in FIG. 15A.

As can be seen from FIG. 16A, it is found that boron of the magnetization free layer (the second magnetic layer) is not diffused to other layers but remains in the magnetization free layer by providing the functional layer 25, similarly to the first sample S01. The EELS intensity of boron in the first portion 20p on the spacer layer 30 side of the magnetization free layer is lower than the EELS intensity of boron in the second portion 20q on the functional layer 25 side.

The MR ratio of the fourth sample S04 is 187%. The MR ratio of the fourth sample S04 is higher than the MR ratio of the first sample S01. The MR ratio is improved in the fourth sample S04. This is presumed to be due to the fact that the first portion 20p having crystallinity is provided on the spacer layer 30 (a Mg—O layer) side. In the fourth sample S04, the gauge factor can be improved by the high MR ratio.

In the fourth sample S04, the magnetostriction is 20 ppm, and the coercivity is 3.8 Oe. From the results, even when the first portion 20p having crystallinity is provided, a low coercivity can be achieved by providing the second portion 20q of an amorphous structure. The magnetic properties in the second magnetic layer 20 are the sum of the magnetic properties of the first portion 20p and the magnetic properties of the second portion 20q, for example.

For the functional layer 25, an oxide material or a nitride material is used. In the oxide material or the nitride material, atoms are chemically bonded. Therefore, the effect of suppressing the diffusion of boron is high. A Mg—O layer with a thickness of 2.0 nm may be used as the functional layer 25, for example.

As the oxide material or the nitride material used for the functional layer 25, an oxide material including at least one element selected from the first group consisting of Mg, Al, Si, Ti, V, Cr, Mn, Fe, Co, Ni, Cu, Zn, Zr, Nb, Mo, Ru, Rh, Pd, Ag, Hf, Ta, W, Sn, Cd, and Ga or a nitride material including at least one element selected from the first group may be used, as described above.

The functional layer 25 does not contribute to the magnetoresistance effect. Hence, the resistance-area product (RA) of the functional layer 25 is preferably low. The resistance-area product (RA) of the functional layer 25 is preferably lower than the resistance-area product (RA) of the spacer layer 30 contributing to the magnetoresistance effect, for example. For the functional layer 25, an oxide including at least one element selected from the group consisting of Mg, Ti, V, Zn, Sn, Cd, and Ga or a nitride including the element is used, for example. The barrier height of oxides or nitrides of these elements is low. The resistance-area product (RA) of the functional layer 25 can be reduced by using an oxide or a nitride of these elements.

It is more preferable to use an oxide for the functional layer 25. Chemical bonds in oxides are stronger than chemical bonds in nitrides. The diffusion of boron can be suppressed more effectively by using an oxide for the functional layer 25, for example.

In the specification of this application, oxynitrides are included in either of oxides and nitrides. In the case where the ratio of oxygen is higher than the ratio of nitrogen in an oxynitride, the oxynitride can be included in oxides, for example. In the case where the ratio of nitrogen is higher than the ratio of oxygen in an oxynitride, the oxxynitride can be included in nitrides, for example.

In the case where an oxide or a nitride is used for the functional layer 25, the thickness of the functional layer 25 is preferably 0.5 nm or more. Thereby, the diffusion of boron is suppressed effectively, for example. The thickness of the functional layer 25 is preferably 5 nm or less. Thereby, the resistance-area product (RA) can be reduced, for example. The thickness of the functional layer 25 is preferably not less than 0.5 nm and not more than 5 nm, and more preferably not less than 1 nm and not more than 3 nm. The thickness of the functional layer 25 may be 2 nm or more.

Another metal layer or the like may be interposed between the second magnetic layer 20 and the functional layer 25. If the distance between the second magnetic layer 20 and the functional layer 25 is too long, boron may be diffused in the region between them, and the boron concentration of the second magnetic layer 20 may be reduced, for example. The distance between the second magnetic layer 20 and the functional layer 25 is preferably 10 nm or less, and more preferably 3 nm or less, for example.

FIG. 17A to FIG. 17E are schematic views illustrating other strain sensing elements according to the first embodiment.

Figure 17A:
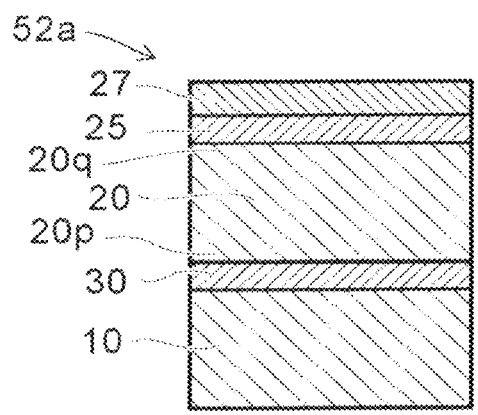
FIG. 17A to FIG. 17E are schematic views showing other strain sensing elements according to the first embodiment.
Figure 17B:
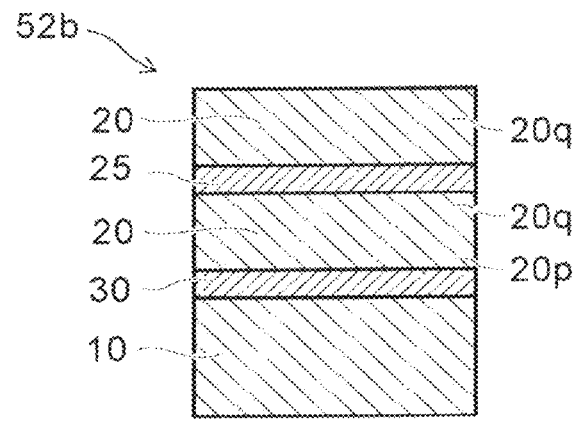

As shown in FIG. 17A, in a strain sensing element 52a according to the embodiment, a magnetic layer 27 is further provided. The functional layer 25 is disposed between the magnetic layer 27 and the second magnetic layer 20. The magnetization of the magnetic layer 27 (the direction thereof) is variable. The material and configuration described in regard to the second magnetic layer 20 may be used for the magnetic layer 27. The magnetic layer 27 and the second magnetic layer 20 may be integrated together to function as a magnetization free layer.

When the magnetic layer 27 and the second magnetic layer 20 are regarded as a magnetization free layer, the functional layer 25 can be regarded as being provided in the magnetization free layer. Also in this case, by the functional layer 25, the diffusion of boron from the second magnetic layer 20 can be suppressed, and a small coercivity Hc is obtained. Although it is presumed that in the magnetic layer 27 boron is diffused and an increase in coercivity Hc occurs, the coercivity Hc as the whole magnetization free layer can be kept small. Thus, the functional layer 25 may be provided in the magnetization free layer. In the case where the functional layer 25 is provided in the magnetization free layer, a stacked film including a plurality of layers may be used as the functional layer 25.

As shown in FIG. 17B to FIG. 17E, in strain sensing elements 52b to 52e according to the embodiment, the functional layer 25 is provided in the second magnetic layer 20. Also in this case, a high gauge factor is obtained.

Figure 17C:
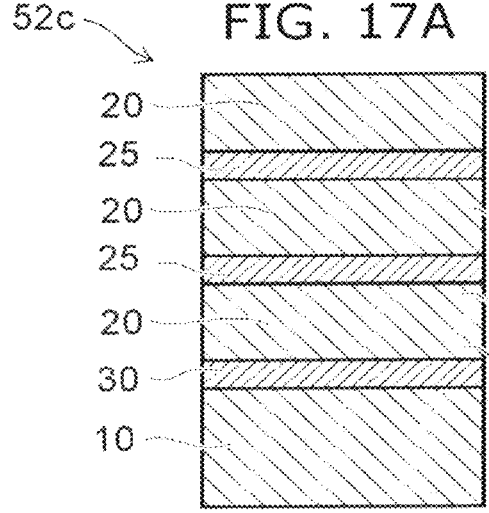

In the strain sensing element 52c illustrated in FIG. 17C, two functional layers 25 are provided in the second magnetic layer 20. The number of functional layers 25 may be 3 or more.

Figure 17D:
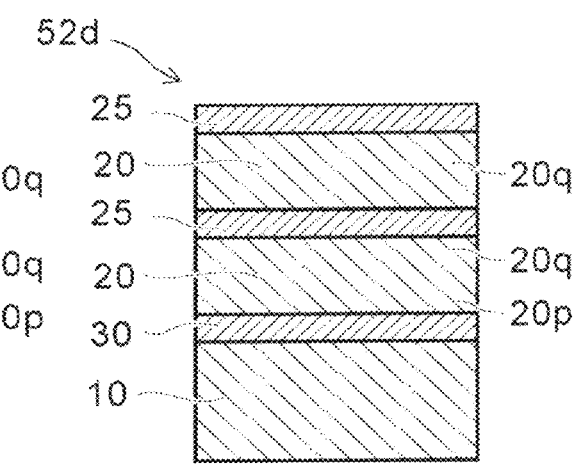

In the strain sensing element 52d illustrated in FIG. 17D, one functional layer 25 is provided on the cap layer side. Furthermore, a functional layer 25 is provided in the second magnetic layer 20.

Figure 17E:
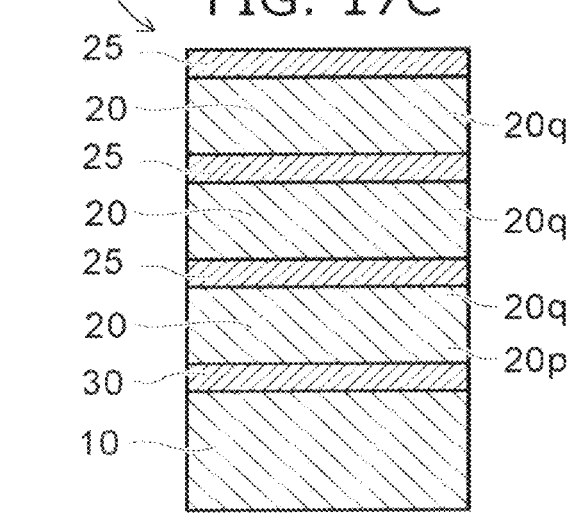

In the strain sensing element 52e illustrated in FIG. 17E, one functional layer 25 is provided on the cap layer side. Furthermore, a plurality of functional layers 25 are provided in the second magnetic layer 20. The number of functional layers 25 may be 3 or more.

As shown in FIGS. 17A to 17E, the MR ratio in the first portion 20p can be improved by reducing the boron concentration CB in the first portion 20p of the second magnetic layer 20 (a portion on the spacer layer 30 side). Thereby, the change in electric resistance R with respect to the change in magnetization direction can be increased, and a high gauge factor can be obtained. On the other hand, by increasing the boron concentration CB in the second portion 20q (a portion away from the spacer layer 30), the coercivity Hc can be reduced in the second portion 20q, and the coercivity Hc of the whole second magnetic layer 20 can be reduced. As shown in FIGS. 17C to 17E, in the case where there are a plurality of functional layers 25, a layer in the second magnetic layer 20 that is located farther from the spacer layer than the first portion 20p and located further to the spacer layer 30 side than any one of the plurality of functional layers 25 can be regarded as the second portion 20q.

As mentioned above, the functional layer 25 may be provided in the magnetization free layer. In this case, diffusion of boron in a portion of the magnetization free layer located between the functional layer 25 and the spacer layer 30 can be suppressed. Thereby, a small coercivity Hc is obtained. That is, the coercivity Hc of the whole magnetization free layer can be kept small. In the case where the functional layer 25 is provided in the magnetization free layer, a plurality of functional layers 25 may be provided.

FIG. 18A to FIG. 18C are schematic diagrams illustrating other strain sensing elements according to the first embodiment.

FIG. 18A is a schematic cross-sectional view showing a strain sensing element 52f according to the embodiment. FIG. 18B illustrates the distribution of boron concentration in the strain sensing element 52f.

As shown in FIG. 18A, the second magnetic layer 20 includes a magnetic film 21a, a magnetic film 21b, and a nonmagnetic film 21c. The nonmagnetic film 21c is disposed between the magnetic film 21a and the magnetic film 21b. The magnetic film 21a is disposed between the second magnetic film 21b and the spacer layer 30. A nonmagnetic material is used for the nonmagnetic film 21c.

For the magnetic film 21a, $Co_{40}Fe_{40}B_{20}$ is used, for example. The thickness of the magnetic film 21a is 1.5 nm or more, and is 2.5 nm, for example. For the magnetic film 21b, $Co_{35}Fe_{35}B_{30}$ is used, for example. The thickness of the magnetic film 21b is not less than 3 nm and not more than 5 nm, for example. For the nonmagnetic film 21c, Ru is used, for example. The thickness of the nonmagnetic film 21c is not less than 0.4 nm and not more than 1.2 nm.

The magnetization of the magnetic film 21b and the magnetization of the magnetic film 21a work together. The magnetic film 21b and the magnetic film 21a work in an integrated manner. The stacked body of the magnetic film 21a, the magnetic film 21b, and the nonmagnetic film 21c forms a magnetization free layer. When the thickness of the nonmagnetic film 21c is, for example, approximately 1.2 nm or less, the magnetization of the magnetic film 21b and the magnetization of the magnetic film 21a work together.

FIG. 18C is a schematic cross-sectional view showing a strain sensing element 52g according to the embodiment.

As shown in FIG. 18C, the second magnetic layer 20 includes the magnetic film 21a, the nonmagnetic film 21c, the magnetic film 21b, a nonmagnetic film 21e, and a magnetic film 21d. These films are stacked in this order. The configuration described in regard to the magnetic film 21a may be used for the magnetic film 21d, for example. The configuration described in regard to the nonmagnetic film 21c may be used for the nonmagnetic film 21e. Thus, a plurality of nonmagnetic films may be provided in the second magnetic layer 20. The number of nonmagnetic films in the second magnetic layer 20 may be 3 or more.

In the embodiment, the spacer layer 30 may have a stacked structure. The spacer layer 30 may include a first nonmagnetic film and a second nonmagnetic film, for example. The second nonmagnetic film is provided between the first nonmagnetic film and the second magnetic layer 20. A Mg—O film is provided in the first nonmagnetic film, for example. A film with a higher Mg concentration than the first nonmagnetic film is used as the second nonmagnetic film.

Figure 19:
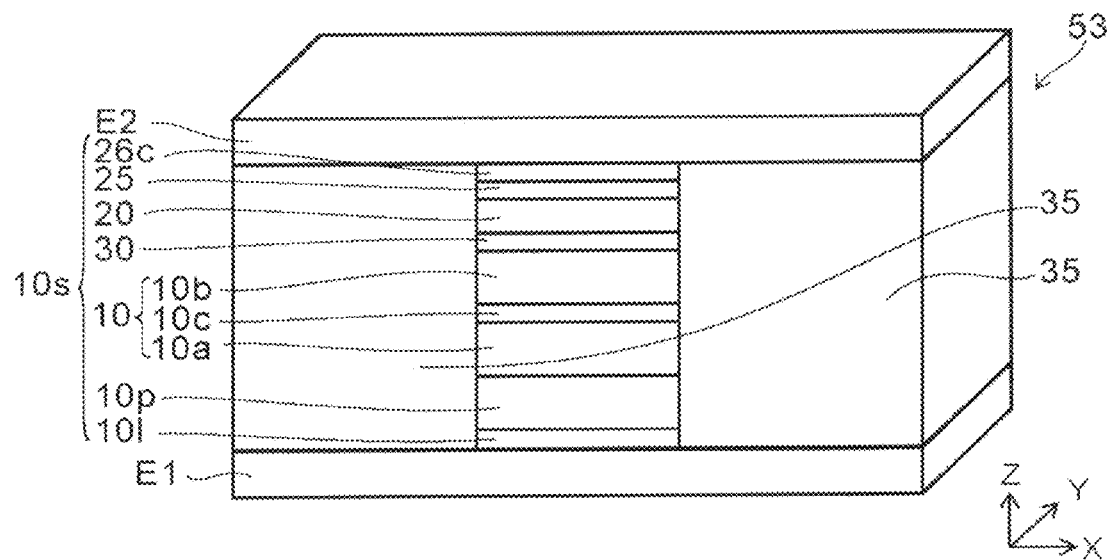
FIG. 19 is a schematic perspective view showing another strain sensing element according to the first embodiment.

FIG. 19 is a schematic perspective view illustrating another strain sensing element according to the first embodiment.

As illustrated in FIG. 19, an insulating layer 35 is provided in a strain sensing element 53 according to the embodiment. The insulating layer 35 (an insulating portion) is provided between the first electrode E1 and the second electrode E2, for example. The insulating layer 35 surrounds the stacked body 10s between the first electrode E1 and the second electrode E2. The insulating layer 35 is provided to oppose the side wall of the stacked body 10s.

For the insulating layer 35, an aluminum oxide (for example, $Al_2O_3$), a silicon oxide (for example, $SiO_2$), or the like may be used, for example. By the insulating layer 35, leakage current around the stacked body 10s can be suppressed.

Figure 20:
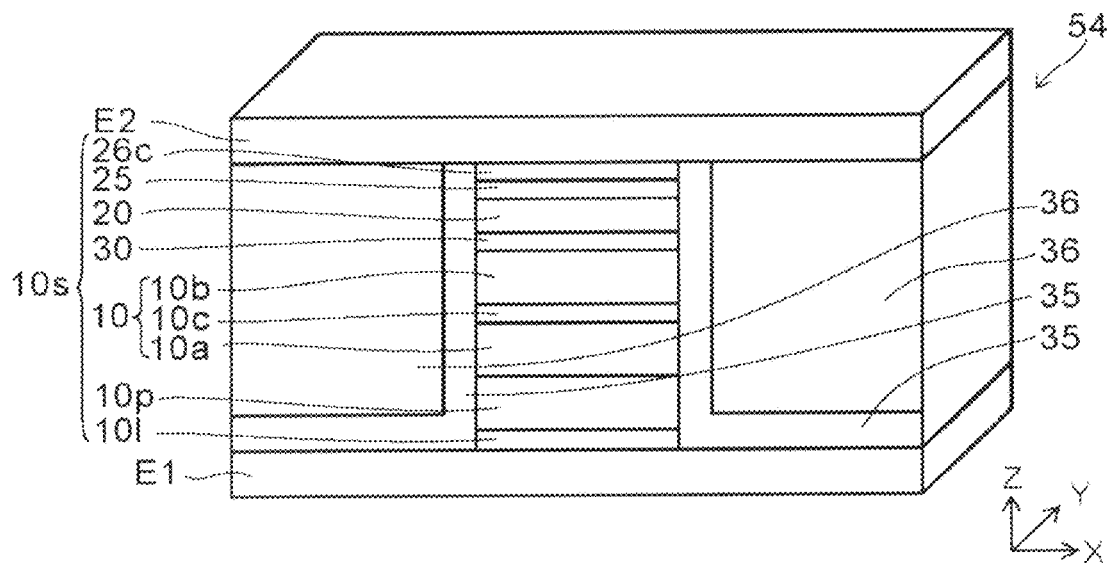
FIG. 20 is a schematic perspective view showing another strain sensing element according to the first embodiment.

FIG. 20 is a schematic perspective view illustrating another strain sensing element according to the first embodiment.

As illustrated in FIG. 20, a hard bias layer 36 is further provided in a strain sensing element 54 according to the embodiment. The hard bias layer 36 (a hard bias portion) is provided between the first electrode E1 and the second electrode E2. The insulating layer 35 is disposed between the hard bias layer 36 and the stacked body 10s, for example. In this example, the insulating layer 35 extends between the hard bias layer 36 and the first electrode E1.

By the magnetization of the hard bias layer 36, at least one of the magnetization 10m of the first magnetic layer 10 and the magnetization 20m of the second magnetic layer 20 is set to a desired direction. By the hard bias layer 36, at least one of the magnetization 10m and the magnetization 20m can be set to a desired direction in a state where no force is applied to the strain sensing element.

For the hard bias layer 36, a hard ferromagnetic material with a relatively high magnetic anisotropy such as CoPt, CoCrPt, and FePt is used, for example. As the hard bias layer 36, a structure in which a layer of a soft magnetic material such as FeCo and Fe and an antiferromagnetic layer are stacked may be used. In this case, the magnetization runs along a prescribed direction due to an exchange coupling. The thickness (for example, the length along the direction from the first electrode E1 toward the second electrode E2) of the hard bias layer 36 is not less than 5 nm and not more than 50 nm, for example.

The hard bias layer 36 and the insulating layer 35 mentioned above can be used for any one of the strain sensing elements described above and below.

Figure 21:
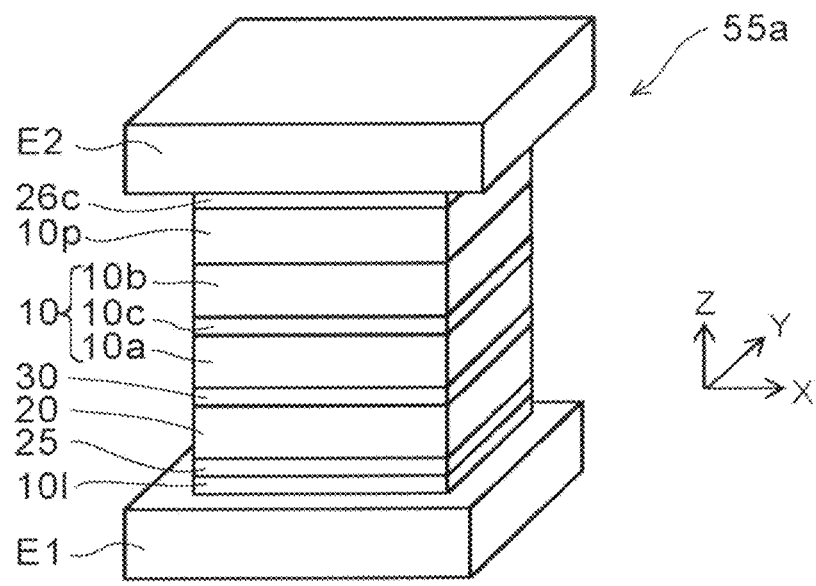
FIG. 21 is a schematic perspective view showing another strain sensing element according to the first embodiment.

FIG. 21 is a schematic perspective view illustrating another strain sensing element according to the first embodiment.

As shown in FIG. 21, another strain sensing element 55a according to the embodiment includes the first electrode E1 (for example, a lower electrode), the underlayer 10l, the functional layer 25, the second magnetic layer 20 (a magnetization free layer), the spacer layer 30, the first magnetization pinned layer 10a, the magnetic coupling layer 10c, the second magnetization pinned layer 10b, the pinning layer 10p, the cap layer 26c, and the second electrode E2 (for example, an upper electrode) that are sequentially aligned. The strain sensing element 55a is a top spin valve type.

As the underlayer 10l, Ta/Cu is used, for example. The thickness of the Ta layer is 3 nm, for example. The thickness of the Ru layer is 5 nm, for example.

As the functional layer 25, Mg—O is used, for example. The thickness of the Mg—O layer is 1.5 nm, for example.

As the second magnetic layer 20, $Co_{40}Fe_{40}B_{20}$ is used, for example.

The thickness of the $Co_{40}Fe_{40}B_{20}$ layer is 4 nm, for example.

As the spacer layer 30, a Mg—O layer with a thickness of 1.6 nm is used, for example.

As the first magnetization pinned layer 10a, $Co_{40}Fe_{40}B_{20}$/$Fe_{50}Co_{50}$ is used, for example. The thickness of the $Co_{40}Fe_{40}B_{20}$ layer is 2 nm, for example. The thickness of the $Fe_{50}Co_{50}$ layer is 1 nm, for example.

As the magnetic coupling layer 10c, a Ru layer with a thickness of 0.9 nm is used, for example.

As the second magnetization pinned layer 10b, a Co$_{75}$Fe$_{25}$ layer with a thickness of 2.5 nm is used, for example.

As the pinning layer 10p, an IrMn layer with a thickness of 7 nm is used, for example.

As the cap layer 26c, Ta/Ru is used. The thickness of the Ta layer is 1 nm, for example. The thickness of the Ru layer is 5 nm, for example.

The material described in regard to the strain sensing element 51 may be used for the layers included in the strain sensing element 55a, for example.

Figure 22:
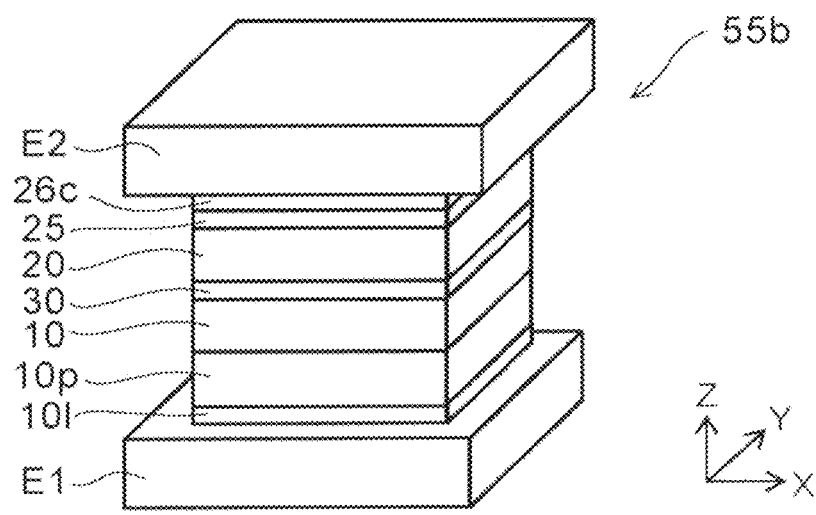
FIG. 22 is a schematic perspective view showing another strain sensing element according to the first embodiment.

FIG. 22 is a schematic perspective view illustrating another strain sensing element according to the first embodiment.

As shown in FIG. 22, another strain sensing element 55b according to the embodiment includes the first electrode E1 (for example, a lower electrode), the underlayer 10l, the pinning layer 10p, the first magnetic layer 10, the spacer layer 30, the second magnetic layer 20, the functional layer 25, the cap layer 26c, and the second electrode E2 (for example, an upper electrode) that are sequentially aligned. A single pin structure using a single magnetization pinned layer is used in the strain sensing element 55b.

As the underlayer 10l, Ta/Ru is used, for example. The thickness of the Ta layer is 3 nm, for example. The thickness of the Ru layer is 2 nm, for example.

As the pinning layer 10p, an IrMn layer with a thickness of 7 nm is used, for example.

As the first magnetic layer 10, a Co$_{40}$Fe$_{40}$B$_{20}$ layer with a thickness of 3 nm is used, for example.

As the spacer layer 30, a Mg—O layer with a thickness of 1.6 nm is used, for example.

As the second magnetic layer 20, Co$_{40}$Fe$_{40}$B$_{20}$ is used, for example. The thickness of the Co$_{40}$Fe$_{40}$B$_{20}$ layer is 4 nm, for example.

As the functional layer 25, a Mg—O layer with a thickness of 1.5 nm is used, for example.

As the cap layer 26c, Ta/Ru is used, for example. The thickness of the Ta layer is 1 nm, for example. The thickness of the Ru layer is 5 nm, for example.

The material described in regard to the strain sensing element 51 may be used for the layers included in the strain sensing element 55b, for example.

Figure 23:
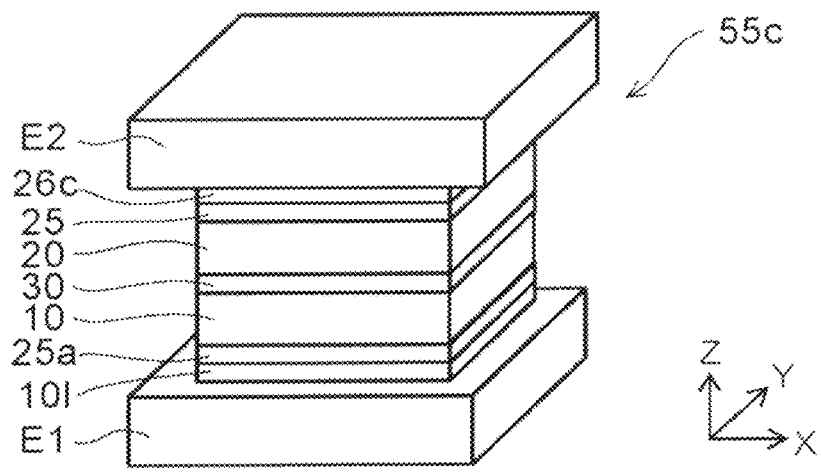
FIG. 23 is a schematic perspective view showing another strain sensing element according to the first embodiment.

FIG. 23 is a schematic perspective view illustrating another strain sensing element according to the first embodiment.

As shown in FIG. 23, another strain sensing element 55b according to the embodiment includes the first electrode E1 (for example, a lower electrode), the underlayer 10l, another functional layer 25a (a second functional layer), the first magnetic layer 10, the spacer layer 30, the second magnetic layer 20, the functional layer 25 (a first functional layer), the cap layer 26c, and the second electrode E2 (for example, an upper electrode) that are sequentially aligned. In this example, the first magnetic layer 10 is a magnetization free layer, and also the second magnetic layer 20 is a magnetization free layer.

As the underlayer 10l, Ta/Ru is used, for example, The thickness of the Ta layer is 3 nm, for example. The thickness of the Ru layer is 5 nm, for example.

As the functional layer 25a, a Mg—O layer with a thickness of 1.5 nm is used, for example.

As the first magnetic layer 10, a Co$_{40}$Fe$_{40}$B$_{20}$ layer with a thickness of 4 nm is used, for example.

As the spacer layer 30, a Mg—O layer with a thickness of 1.6 nm is used, for example.

As the second magnetic layer 20, Co$_{40}$Fe$_{40}$B$_{20}$ is used, for example. The thickness of the Co$_{40}$Fe$_{40}$B$_{20}$ layer is 4 nm, for example.

As the functional layer 25, a Mg—O layer with a thickness of 1.5 nm is used, for example.

As the cap layer 26c, Ta/Ru is used, for example. The thickness of the Ta layer is 1 nm, for example. The thickness of the Ru layer is 5 nm, for example.

The material described in regard to the strain sensing element 51 may be used for the layers included in the strain sensing element 55c, for example. The material and configuration described in regard to the second magnetic layer 20 in the stain sensing element 51 may be used for the first magnetic layer 10 in the strain sensing element 55c. The material and configuration described in regard to the functional layer 25 in the strain sensing element 51 may be used for the functional layer 25a in the strain sensing element 55c.

In this example, the first magnetic layer 10 may be regarded as the second magnetic layer 20, and the functional layer 25 may be regarded as the functional layer 25a.

In the case where two magnetization free layers are provided like the strain sensing element 55c, the relative angle between the magnetizations of the two magnetization free layers changes in accordance with the strain E. Thereby, the element can be made to function as a strain sensor. In this case, the value of the magnetostriction of a second magnetization free layer and the value of the magnetostriction of a first magnetization free layer may be designed so as to be different from each other. Thereby, the relative angle between the magnetizations of the two magnetization free layers changes in accordance with the strain E.

Second Embodiment

Figure 24:
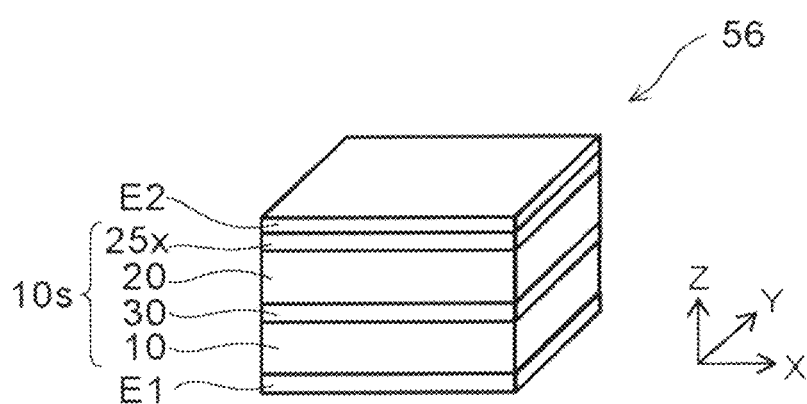
FIG. 24 is a schematic cross-sectional view showing a strain sensing element according to a second embodiment.

FIG. 24 is a schematic cross-sectional view illustrating a strain sensing element according to a second embodiment.

As shown in FIG. 24, also a strain sensing element 56 according to the embodiment includes a functional layer 25x, the first magnetic layer 10, the second magnetic layer 20, and the spacer layer 30. The arrangement of these layers is the same as the arrangement described in regard to the first embodiment, and a description is omitted.

In the embodiment, the material used for the functional layer 25x is different from the material used for the functional layer 25 described in regard to the first embodiment. Otherwise, the embodiment is similar to the first embodiment. Examples of the functional layer 25x will now be described.

In the strain sensing element 56, for the functional layer 25x, at least one selected from the group consisting of magnesium (Mg), silicon (Si), and aluminum (Al) is used, for example. For the functional layer 25x, a material including these light elements is used. These light elements combine with boron to produce compounds. At least one of a Mg—B compound, an Al—B compound, and a Si—B compound is formed in a portion including the interface with the second magnetic layer 20 of the functional layer 25x, for example. These compounds suppress the diffusion of boron.

In the embodiment, by providing the functional layer 25x, the diffusion of boron included in the second magnetic layer 20 can be suppressed, and the amorphous structure of the second magnetic layer 20 can be maintained. Consequently, a high gauge factor can be obtained.

Also in the strain sensing element 56 according to the embodiment, the first magnetic layer 10 may include the second magnetization pinned layer 10b, the magnetic coupling layer 10c, and the first magnetization pinned layer 10a described in regard to FIG. 3.

Characteristics of strain sensing elements according to the embodiment will now be described.

The configuration of a fifth sample is as follows:
The underlayer 10l: Ta (1 nm)/Ru (2 nm)
The pinning layer 10p: $Ir_{22}Mn_{78}$ (7 nm)
The second magnetization pinned layer 10b: $Co_{75}Fe_{25}$ (2.5 nm)
The magnetic coupling layer 10c: Ru (0.9 nm)
The first magnetization pinned layer 10a: $Co_{40}Fe_{40}B_{20}$ (3 nm)
The spacer layer 30: Mg—O (1.6 nm)
The second magnetic layer 20: $Co_{40}Fe_{40}B_{20}$ (4 nm)
The functional layer 25x: Mg (1.6 nm)
The cap layer 26c: Cu (1 nm)/Ta (20 nm)/Ru (50 nm)

That is, in the fifth sample, a Mg layer with a thickness of 1.6 nm is used as the functional layer 25x.

On the other hand, in a sixth sample, a Si layer with a thickness of 0.8 nm is used as the functional layer 25x.

In a seventh sample, the functional layer 25x is not provided. In the seventh sample, the second magnetic layer 20 is in contact with the cap layer 26c. The seventh sample is the same as the second sample S02.

Characteristics of these samples have been investigated similarly to those described in regard to the first sample. The results are as follows.

In the fifth sample, the MR is 126%, the coercivity Hc is 2.3 Oe, the magnetostriction constant λ is 21 ppm, and the gauge factor is 2861.

In the sixth sample, the MR is 104%, the coercivity Hc is 3.8 Oe, the magnetostriction constant λ is 19 ppm, and the gauge factor is 2091.

In the seventh sample, the MR is 190%, the coercivity Hc is 27 Oe, the magnetostriction constant λ is 30 ppm, and the gauge factor is 895.

Thus, a high gauge factor is obtained by using the functional layer 25x.

The diffusion of boron from the second magnetic layer 20 can be suppressed by providing the functional layer 25x mentioned above on the second magnetic layer 20 including boron. Consequently, a small coercivity Hc and a large magnetostriction constant λ are obtained. Thereby, a high gauge factor is obtained.

Characteristics of other strain sensing elements according to the embodiment will now be described.

The configuration of an eighth sample is as follows:
The underlayer 10l: Ta (1 nm)/Ru (2 nm)
The pinning layer 10p: $Ir_{22}Mn_{78}$ (7 nm)
The second magnetization pinned layer 10b: $Co_{75}Fe_{25}$ (2.5 nm)
The magnetic coupling layer 10c: Ru (0.9 nm)
The first magnetization pinned layer 10a: $Co_{40}Fe_{40}B_{20}$ (3 nm)
The spacer layer 30: Mg—O (2 nm)
The second magnetic layer 20: described later
The cap layer 26c: Ta (20 nm)/Ru (50 nm)

In the eighth sample, the stacked film of the second magnetic layer 20 that forms a magnetization free layer and the functional layer 25x has the following configuration. $Co_{40}Fe_{40}B_{20}$ (4 nm)/three layers of the combination of {$Co_{40}Fe_{40}B_{20}$ (1 nm)/Si (0.25 nm)}/$Co_{40}Fe_{40}B_{20}$ (1 nm) is used as the stacked film. The layer of $Co_{40}Fe_{40}B_{20}$ (4 nm) of the stacked film is regarded as the second magnetic layer 20, for example. At least one of the three Si (0.25 nm) layers of the stacked film is regarded as the functional layer 25x.

In a ninth sample, the stacked film of the second magnetic layer 20 that forms a magnetization free layer and the functional layer 25x has the following configuration. $Co_{40}Fe_{40}B_{20}$ (4 nm)/three layers of the combination of {$Co_{40}Fe_{40}B_{20}$ (1 nm)/Al (0.25 nm)}/$Co_{40}Fe_{40}B_{20}$ (1 nm) is used as the stacked film. The layer of $Co_{40}Fe_{40}B_{20}$ (4 nm) of the stacked film is regarded as the second magnetic layer 20, for example. At least one of the three Al (0.25 nm) layers of the stacked film is regarded as the functional layer 25x. In the ninth sample, the configuration excluding the second magnetic layer 20 and the functional layer 25x is similar to the eighth sample.

In a tenth sample, $Co_{40}Fe_{40}B_{20}$ (4 nm) is used as the second magnetic layer 20 that forms a magnetization free layer. The functional layer 25x is not provided. In the tenth sample, the configuration excluding the second magnetic layer 20 and the functional layer 25x is similar to the eighth sample. That is, the tenth sample is the same as the second sample S02 mentioned above.

Characteristics of these samples have been investigated similarly to those described in regard to the first embodiment. The results are as follows.

In the eighth sample, the MR is 176%, the coercivity Hc is 4.8 Oe, the magnetostriction constant λ is 22 ppm, and the gauge factor is 2849.

In the ninth sample, the MR is 169%, the coercivity Hc is 7.1 Oe, the magnetostriction constant λ is 20 ppm, and the gauge factor is 2195.

In the tenth sample (the seventh sample), the MR is 190%, the coercivity Hc is 27 Oe, the magnetostriction constant λ is 30 ppm, and the gauge factor is 895.

Thus, a high gauge factor is obtained by using the functional layer 25x.

Thus, the diffusion of boron from the magnetization free layer can be suppressed by interposing a layer of a material including at least one light element selected from the group consisting of Mg, Al, and Si in the magnetization free layer including boron. Consequently, a small coercivity Hc and a large magnetostriction constant λ are obtained. Thereby, a high gauge factor is obtained.

In the embodiment, in the case where a material including at least one selected from the group consisting of Mg, Al, and Si is used as the functional layer 25x, the thickness of the functional layer 25x is preferably 0.5 nm or more, for example. Thereby, the diffusion of boron is suppressed effectively, for example. The thickness of the functional layer 25x is preferably 5 nm or less. Thereby, the diffusion of the surplus Mg, Al, or Si to the second magnetic layer 20 can be suppressed, for example. The thickness of the functional layer 25x is preferably not less than 0.5 nm and not more than 5 nm, and preferably not less than 1 nm and not more than 3 nm. The thickness of the functional layer 25x may be 2 nm or more.

Another metal layer or the like may be interposed between the functional layer 25x and the second magnetic layer 20. If the distance between the functional layer 25x and the second magnetic layer 20 is too long, boron may be diffused in the region between them, and the boron concentration in the second magnetic layer 20 may be reduced. The distance between the functional layer 25x and the second magnetic layer 20 is preferably 10 nm or less, and more preferably 3 nm or less, for example.

The functional layer 25x may be provided in the magnetization free layer as mentioned above. In this case, the diffusion of boron in a portion of the magnetization free layer located between the functional layer 25x and the spacer layer 30 can be suppressed. Thereby, a small coercivity Hc is obtained. That is, the coercivity Hc of the whole magnetization free layer can be kept small. In the case where the functional layer 25x is provided in the magnetization free layer, a plurality of functional layers 25x may be provided.

Third Embodiment

The embodiment relates to a pressure sensor. In the pressure sensor, a strain sensing element of at least one of the first embodiment and the second embodiment and modifications thereof is used. In the following, the case where the strain sensing element 50 is used as the strain sensing element is described.

Figure 25A:
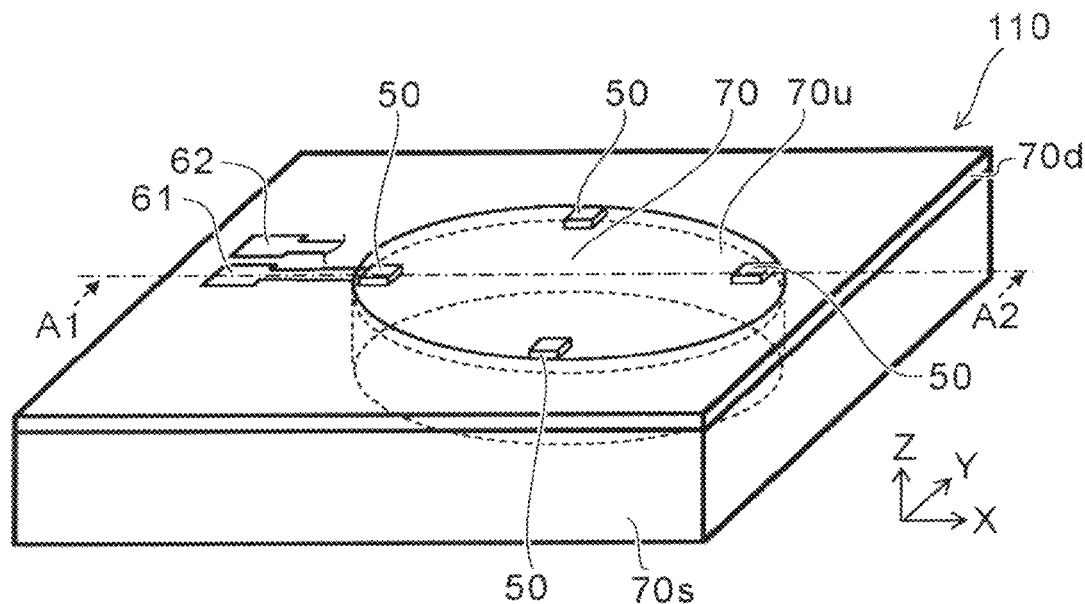
FIG. 25A and FIG. 25B are schematic perspective views showing a pressure sensor according to a third embodiment.
Figure 25B:
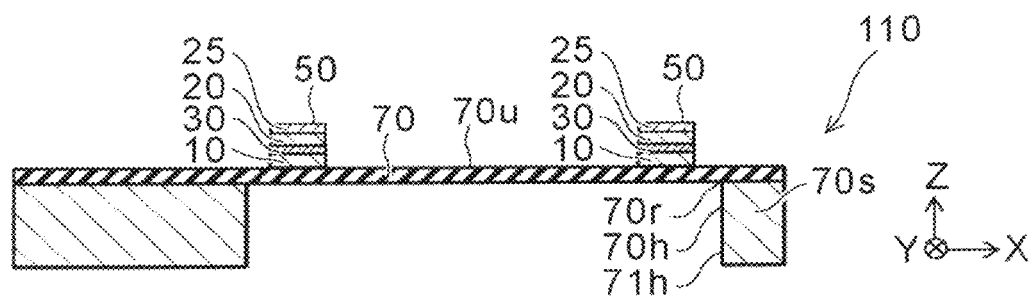

FIG. 25A and FIG. 25B are schematic perspective views illustrating a pressure sensor according to a third embodiment.

FIG. 25A is a schematic perspective view. FIG. 25B is a cross-sectional view taken along line A1-A2 of FIG. 25A.

As shown in FIG. 25A and FIG. 25B, the pressure sensor 110 according to the embodiment includes the film unit 70 and the strain sensing element 50.

The film unit 70 is supported by a support 70s, for example. The support 70s is a substrate, for example. The film unit 70 has a flexible region, for example. The film unit 70 is a diaphragm, for example. The film unit 70 may be integrated with or separated from the support 70s. For the film unit 70, the same material as the support 70s may be used, or a different material from the support 70s may be used. Part of a substrate that forms the support 70s may be removed, and a portion of the substrate with a smaller thickness may form the film unit 70.

The thickness of the film unit 70 is smaller than the thickness of the support 70s. In the case where the same material is used for the film unit 70 and the support 70s and they are integrated together, a portion with a smaller thickness forms the film unit 70, and a portion with a larger thickness forms the support 70s.

The support 70s may have a through hole 70h penetrating through the support 70s in the thickness direction, and the film unit 70 may be provided so as to cover the through hole 70h. At this time, the film of the material that forms the film unit 70 may extend also on a portion other than the through hole 70h of the support 70s, for example. At this time, of the film of the material that forms the film unit 70, a portion overlapping with the through hole 70h forms the film unit 70.

The film unit 70 has an outer edge 70r. In the case where the same material is used for the film unit 70 and the support 70s and they are integrated together, the outer edge of the portion with a smaller thickness is the outer edge 70r of the film unit 70. In the case where the support 70s has the through hole 70h penetrating through the support 70s in the thickness direction and the film unit 70 is provided so as to cover the through hole 70h, the outer edge of the portion overlapping with the through hole 70h of the film of the material that forms the film unit 70 is the outer edge 70r of the film unit 70.

The support 70s may continuously support the outer edge 70r of the film unit 70, and may support part of the outer edge 70r of the film unit 70.

The strain sensing element 50 is provided on the film unit 70. The strain sensing element 50 is provided on part of the film unit 70, for example. In this example, a plurality of strain sensing elements 50 are provided on the film unit 70. The number of strain sensing elements provided on the film unit may be one.

As shown in FIG. 25B, in the strain sensing element 50, the first magnetic layer 10 is disposed between the functional layer 25 and the film unit 70, for example. The first magnetic layer 10 is disposed between the second magnetic layer 20 and the film unit 70.

In this example, a first interconnection 61 and a second interconnection 62 are provided. The first interconnection 61 is connected to the strain sensing element 50. The second interconnection 62 is connected to the strain sensing element 50. An interlayer insulation film is provided between the first interconnection 61 and the second interconnection 62, and the first interconnection 61 and the second interconnection 62 are electrically insulated, for example. A voltage is applied between the first interconnection 61 and the second interconnection 62, and the voltage is applied to the strain sensing element 50 via the first interconnection 61 and the second interconnection 62. When a pressure is applied to the pressure sensor 110, the film unit 70 is deformed. In the strain sensing element 50, the electric resistance R changes in accordance with the deformation of the film unit 70. The pressure can be sensed by sensing the change in electric change R via the first interconnection 61 and the second interconnection 62.

As the support 70s, a plate-like substrate may be used, for example. A hollow portion 71h (the through hole 70h) is provided in the substrate, for example.

For the support 70s, a semiconductor material such as silicon, a conductive material such as a metal, or an insulating material may be used, for example. The support 70s may include silicon oxide, silicon nitride, or the like, for example. The interior of the hollow portion 71h is in a reduced pressure state (vacuum state), for example. The interior of the hollow portion 71h may be filled with a gas such as air or a liquid. The interior of the hollow portion 71h is designed so that the film unit 70 can bend. The interior of the hollow portion 71h may be connected to the outside air.

The film unit 70 is provided on the hollow portion 71h. As the film unit 70, a portion thinned by processing of a substrate that forms the support 70s is used, for example. The thickness (the length in the Z-axis direction) of the film unit 70 is smaller than the thickness (the length in the Z-axis direction) of the substrate.

When a pressure is applied to the film unit 70, the film unit is deformed. The pressure corresponds to the pressure that is to be sensed by the pressure sensor 110. The applied pressure includes pressure caused by sound waves, ultrasonic waves, or the like. In the case of sensing pressure caused by sound waves, ultrasonic waves, or the like, the pressure sensor 110 functions as a microphone.

For the film unit 70, an insulating material is used, for example. The film unit 70 includes at least one of silicon oxide, silicon nitride, and silicon oxynitride, for example. A semiconductor material such as silicon may be used for the film unit 70, for example. A metal material may be used for the film unit 70, for example.

The thickness of the film unit 70 is not less than 0.1 micrometers ($\mu$m) and not more than 3 $\mu$m, for example. The thickness is preferably not less than 0.2 $\mu$m and not more than 1.5 $\mu$m. A stacked body including a silicon oxide film with a thickness of 0.2 $\mu$m and a silicon film with a thickness of 0.4 $\mu$m may be used as the film unit 70, for example.

A plurality of strain sensing elements 50 may be arranged on the film unit 70. A substantially equal change in electric resistance with respect to the pressure can be obtained in the plurality of strain sensing elements 50. As described later, the S/N ratio can be increased by connecting a plurality of strain sensing elements 50 in series or in parallel.

The size of the strain sensing element 50 may be very small. The area of the strain sensing element 50 may be sufficiently smaller than the area of the film unit 70 that is deformed by pressure. The area of the strain sensing element 50 may be not more than 1/5 of the area of the film unit 70, for example.

When the diameter of the film unit 70 is approximately 60 µm, the dimension of the strain sensing element 50 may be 12 µm or less, for example. When the diameter of the film unit 70 is approximately 600 µm, the dimension of the strain sensing element 50 may be 120 µm or less, for example. In view of the processing accuracy of the strain sensing element 50 etc., it is not necessary to set the dimension of the strain sensing element 50 too small. Thus, the dimension of the strain sensing element 50 may be set not less than 0.05 µm and not more than 30 µm, for example.

In this example. the planar shape of the film unit 70 is a circle. The planar shape of the film unit 70 may be also an ellipse (for example, a flat circle), a square, a rectangle, a polygon, or a regular polygon, for example.

Figure 26A:
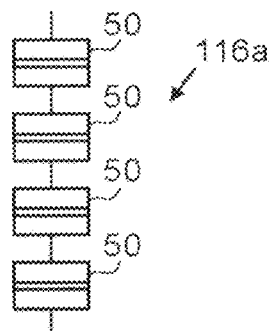
FIG. 26A to FIG. 26C are schematic diagrams showing pressure sensors according to the embodiment. The drawings show examples of the connection state of a plurality of sensing elements.
Figure 26B:
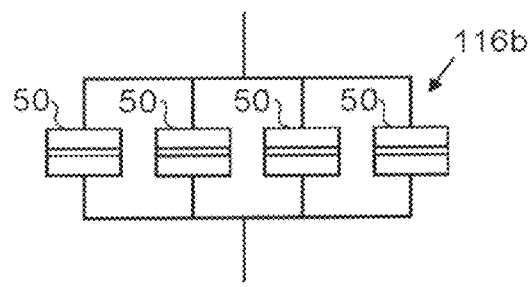
Figure 26C:
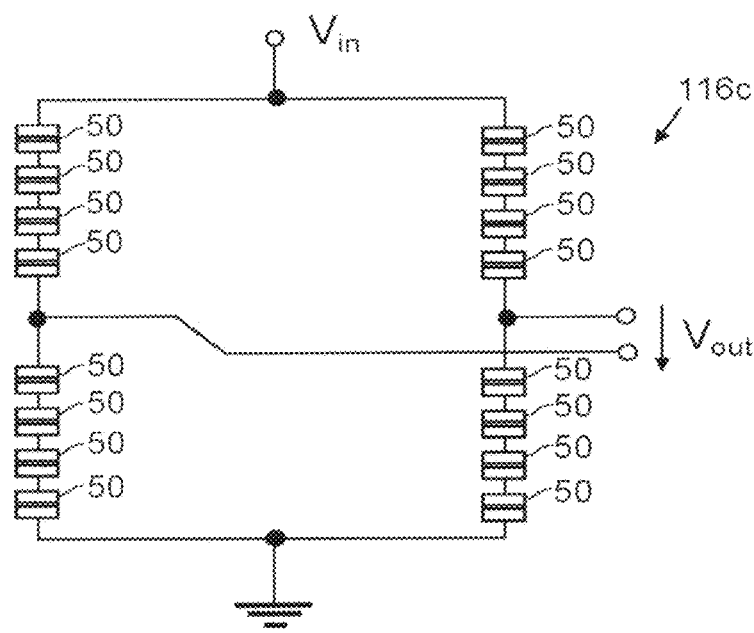

FIG. 26A to FIG. 26C are schematic diagrams illustrating pressure sensors according to the embodiment. The drawings show examples of the connection state of a plurality of sensing elements.

As shown in FIG. 26A, in a pressure sensor 116a according to the embodiment, a plurality of sensing elements 50 are electrically connected in series. When the number of sensing elements 50 connected in series is denoted by N, the electric signal obtained is N times of that when the number of sensing elements 50 is one. On the other hand, the thermal noise and the Schottky noise are $N^{1/2}$ times. That is, the S/N ratio (signal-noise ratio; SNR) is $N^{1/2}$ times. By increasing the number N of sensing elements 50 connected in series, the S/N ratio can be improved without increasing the size of the film unit 70.

A plurality of strain sensing elements 50 provided on the film unit 70 may be electrically connected in series. When the number of strain sensing elements 50 connected in series is denoted by N, the electric signal obtained is N times of that when the number of strain sensing elements 50 is one. On the other hand, the thermal noise and the Schottky noise are $N^{1/2}$ times. That is, the S/N ratio (signal-noise ratio; SNR) is $N^{1/2}$ times. By increasing the number N of strain sensing elements 50 connected in series, the S/N ratio can be improved without increasing the size of the film unit 70.

The bias voltage applied to one strain sensing element is not less than 50 millivolts (mV) and not more than 150 mV, for example. When N strain sensing elements 50 are connected in series, the bias voltage is not less than 50 mV×N and not more than 150 mV×N. When the number N of strain sensing elements 50 connected in series is 25, the bias voltage is not less than 1 V and not more than 3.75 V, for example.

When the value of the bias voltage is 1 V or more, the design of an electric circuit that processes the electric signal obtained from the strain sensing element is easy, and this is preferable in practical terms.

Bias voltages (inter-terminal voltages) exceeding 10 V are not preferable in the electric circuit that processes the electric signal obtained from the strain sensing element. In the embodiment, the number N of strain sensing elements connected in series and the bias voltage are set so that an appropriate voltage range is obtained.

The voltage when the plurality of strain sensing elements are electrically connected in series is preferably not less than 1 V and not more than 10 V, for example. The voltage applied between the terminals of strain sensing elements 50 electrically connected in series (between the terminal of one end and the terminal of the other end) is not less than 1 V and not more than 10 V, for example.

To generate this voltage, when the bias voltage applied to one strain sensing element is 50 my, the number N of strain sensing elements 50 connected in series is preferably not less than 20 and not more than 200. When the bias voltage applied to one strain sensing element is 150 mV, the number N of strain sensing elements connected in series is preferably not less than 7 and not more than 66.

As shown in FIG. 26B, in a pressure sensor 116b according to the embodiment, a plurality of sensing elements 50 are electrically connected in parallel. In the embodiment, at least part of a plurality of strain sensing elements 50 may be electrically connected in parallel.

As shown in FIG. 26C, in a pressure sensor 116c according to the embodiment, a plurality of strain sensing elements 50 may be connected so as to form a Wheatstone bridge circuit. Thereby, the temperature compensation of detected characteristics can be made, for example.

A method for manufacturing a pressure sensor according to the embodiment will now be described. The following is a method for manufacturing a pressure sensor.

FIG. 27A to FIG. 27E are schematic cross-sectional views in order of the steps, illustrating a method for manufacturing a pressure sensor according to the embodiment.

Figure 27A:
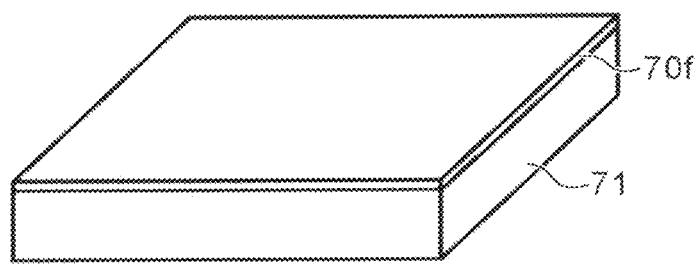
FIG. 27A to FIG. 27E are schematic cross-sectional views in order of the steps, showing a method for manufacturing a pressure sensor according to the embodiment.

As shown in FIG. 27A, a thin film 70f is formed on a substrate 71 (for example, a Si substrate). The substrate 71 forms the support 70s. The thin film 70f forms the film unit 70.

A thin film 70f of $SiO_x/Si$ is formed by sputtering on a Si substrate, for example. A $SiO_x$ single layer, a SiN single layer, or a metal layer of Al or the like may be used as the thin film 70f. A flexible plastic material such as a polyimide and a paraxylene-based polymer may be used as the thin film 70f. An SOI (silicon on insulator) substrate may be used as the substrate 71 and the thin film 70f. In the SOI, a stacked film of $SiO_2/Si$ is formed on a Si substrate by attaching the substrates, for example.

Figure 27B:
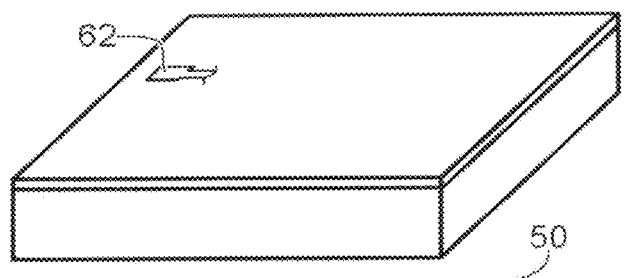

As shown in FIG. 27B, the second interconnection 62 is formed. In this process, a conductive film that forms the second interconnection 62 is formed, and the conductive film is processed by photolithography and etching. In the case where the surroundings of the second interconnection 62 are filled with an insulating film, lift-off process may be used. In the lift-off process, after the etching of the pattern of the second interconnection 62 and before the peeling of the resist, an insulating film is formed into a film over the entire surface and then the resist is removed, for example.

Figure 27C:
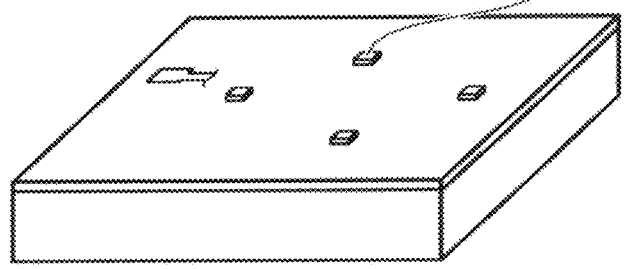

As shown in FIG. 27C, strain sensing elements 50 are formed. In this process, a stacked film that forms the strain sensing element 50 is formed, and the stacked film is processed by photolithography and etching. In the case where the space on the side wall of the stacked body 10s of the strain sensing element 50 is filled with the insulating layer 35, lift-off process may be used. In the lift-off process, after the processing of the stacked body 10s and before the peeling of the resist, the insulating layer 35 is formed into a film over the entire surface and then the resist is removed, for example.

Figure 27D:
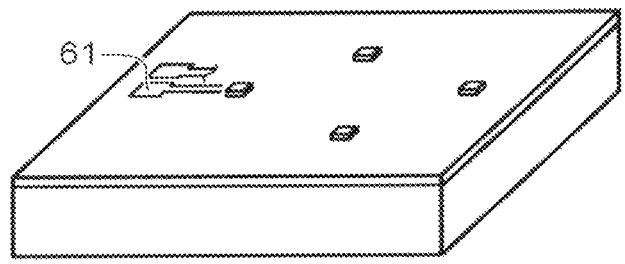

As shown in FIG. 27D, the first interconnection 61 is formed. In this process, a conductive film that forms the first interconnection 61 is formed, and the conductive film is processed by photolithography and etching. In the case where the surroundings of the first interconnection 61 are filled with an insulating film, lift-off process may be used. In the lift-off process, after the processing of the first interconnection 61 and before the peeling of the resist, an insulating film is formed into a film over the entire surface and then the resist is removed.

Figure 27E:
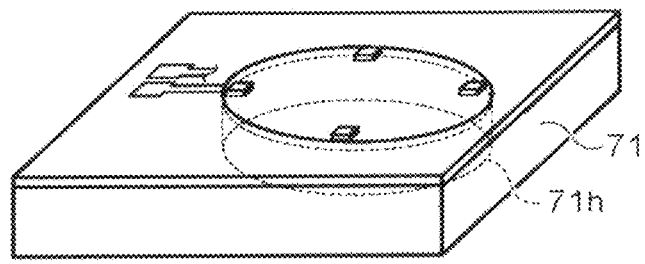

As shown in FIG. 27E, etching is performed from the back surface of the substrate 71 to form the hollow portion 71h. Thereby, the film unit 70 and the support 70s are formed. In the case where a stacked film of SiO$_x$/Si is used as the thin film 70f that forms the film unit 70, deep digging processing of the substrate 71 is performed from the back surface (the lower surface) toward the front surface (the upper surface) of the thin film 70f, for example. Thereby, the hollow portion 71h is formed. In the formation of the hollow portion 71h, a both-surface aligner exposure apparatus may be used, for example. Thereby, the hole pattern of the resist can be formed on the back surface in accordance with the position of the strain sensing element 50 on the front surface.

In the etching of the Si substrate, the Bosch process using RIE may be used, for example. In the Bosch process, an etching process using SF$_6$ gas and a deposition process using C$_4$F$_8$ gas are repeated, for example. Thereby, etching is performed selectively in the depth direction of the substrate 71 (the Z-axis direction) while the etching of the side wall of the substrate 71 is suppressed. A SiO$_x$ layer is used as the end point of the etching, for example. That is, the etching is finished using a SiO$_x$ layer, which is different in etching selectivity from Si. The SiO$_x$ layer functioning as an etching stopper layer may be used as part of the film unit 70. The SiO$_x$ layer may be removed after the etching by treatment with anhydrous hydrogen fluoride and an alcohol, or the like, etc., for example.

Thus, the pressure sensor 110 according to the embodiment is formed. Other pressure sensors according to the embodiment can be manufactured by similar methods.

Figure 28A:
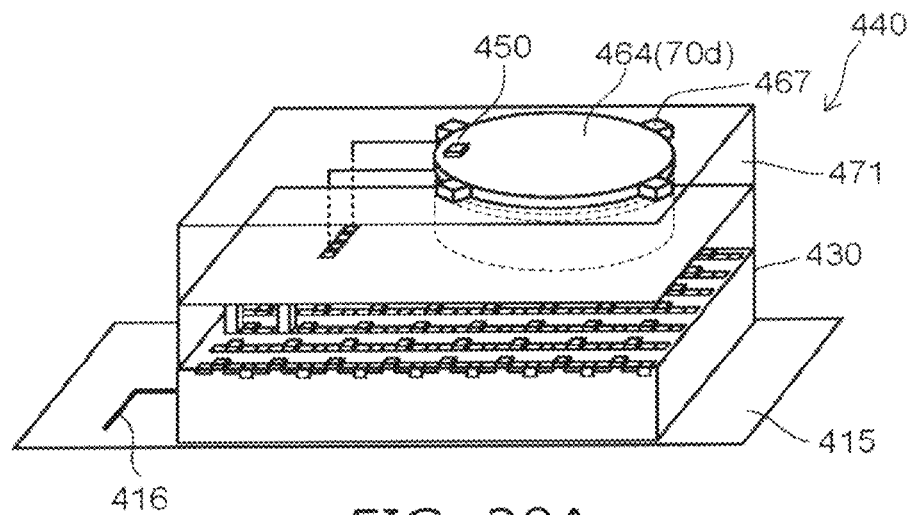
FIG. 28A to FIG. 28C are schematic diagrams showing a pressure sensor according to the embodiment.
Figure 28B:
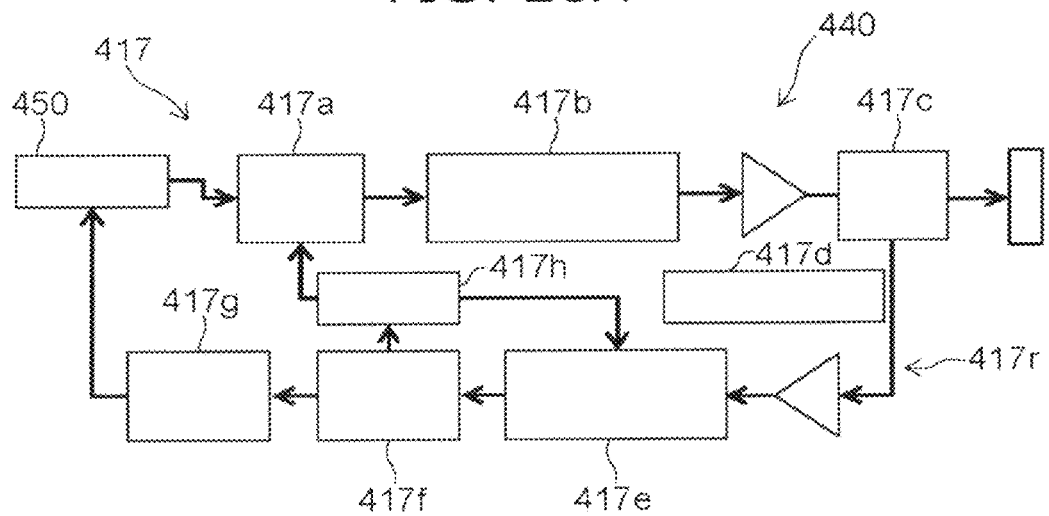
Figure 28C:
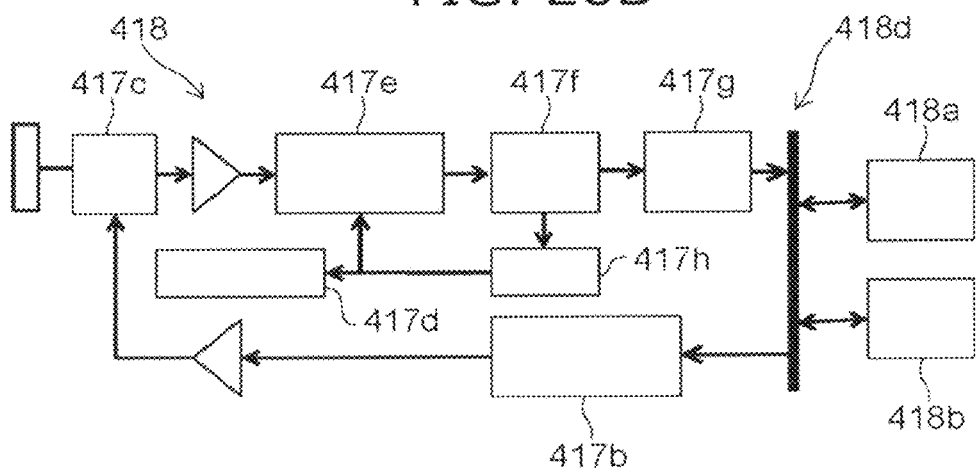

FIG. 28A to FIG. 28C are schematic diagrams illustrating a pressure sensor according to the embodiment. FIG. 28A is a schematic perspective view, and FIG. 28B and FIG. 28C are block diagrams illustrating a pressure sensor 440.

As shown in FIG. 28A and FIG. 28B, in the pressure sensor 440, a base 471, a sensing unit 450, a semiconductor circuit unit 430, an antenna 415, an electric interconnection 416, a transmitting circuit 417, and a receiving circuit 417r are provided.

The antenna 415 is electrically connected to the semiconductor circuit unit 430 via the electric interconnection 416.

The transmitting circuit 417 transmits data based on an electric signal traveling through the sensing unit 450 wirelessly. At least part of the transmitting circuit 417 may be provided in the semiconductor circuit unit 430.

The receiving circuit 417r receives a control signal from an electronic device 418d. At least part of the receiving circuit 417r may be provided in the semiconductor circuit unit 430. By providing the receiving circuit 417r, the operation of the pressure sensor 440 can be controlled by operating the electronic device 418d, for example.

As shown in FIG. 28B, in the transmitting circuit 417, an A/D converter 417a connected to the sensing unit 450 and a Manchester encoding unit 417b may be provided, for example. A switching unit 417c may be provided to switch between transmission and reception. In this case, a timing controller 417d may be provided, and switching in the switching unit 417c can be controlled by the timing controller 417d. A data correction unit 417e, a synchronization unit 417f, a determination unit 417g, and a voltage-controlled oscillator 417h (VCO) may be further provided.

As shown in FIG. 28C, a receiving unit 418 is provided in the electronic device 418d used in combination with the pressure sensor 440. As the electronic device 418d, an electronic device such as a mobile terminal may be given, for example.

In this case, the pressure sensor 440 including the transmitting circuit 417 and the electronic device 418d including the receiving unit 418 may be used in combination.

In the electronic device 418d, a Manchester encoding unit 417b, a switching unit 417c, a timing controller 417d, a data correction unit 417e, a synchronization unit 417f, a determination unit 417g, a voltage-controlled oscillator 417h, a memory unit 418a, and a central processing unit 418b (CPU) may be provided.

In this example, the pressure sensor 440 further includes a fixing unit 467. The fixing unit 467 fixes a film unit 464 (70d) to the base 471. The fixing unit 467 may have a larger thickness dimension than the film unit 464 so as to bend less easily even when an external pressure is applied.

Fixing units 467 may be provided at equal intervals at the edge of the film unit 464, for example.

The fixing unit 467 may be provided so as to continuously surround the entire periphery of the film unit 464 (70d).

The fixing unit 467 may be formed of the same material as the material of the base 471, for example. In this case, the fixing unit 467 may be formed of silicon or the like, for example.

The fixing unit 467 may be formed of the same material as the material of the film unit 464 (70d), for example.

A method for manufacturing a pressure sensor according to the embodiment will now be described.

FIG. 29A, FIG. 29B, FIG. 30A, FIG. 30B, FIG. 31A, FIG. 31B, FIG. 32A, FIG. 32B, FIG. 33A, FIG. 33B, FIG. 34A, FIG. 34B, FIG. 35A, FIG. 35B, FIG. 36A, FIG. 36B, FIG. 37A, FIG. 37B, FIG. 38A, FIG. 38B, FIG. 39A, FIG. 39B, FIG. 40A, and FIG. 40B are schematic views illustrating a method for manufacturing a pressure sensor according to the embodiment.

FIG. 29A to FIG. 40A are schematic plan views, and FIG. 29B to FIG. 40B are schematic cross-sectional views.

As shown in FIG. 29A and FIG. 29B, a semiconductor layer 512M is formed on a surface portion of a semiconductor substrate 531. Subsequently, an element isolation insulating layer 512I is formed on the upper surface of the semiconductor layer 512M. Subsequently, a gate 512G is formed on the semiconductor layer 512M via a not-shown insulating layer. Subsequently, a source 512S and a drain 512D are formed on both sides of the gate 512G to form a transistor 532. Subsequently, an interlayer insulating film 514a is formed thereon, and an interlayer insulating film 514b is formed.

Subsequently, in the region that forms a non-hollow portion, trenches and holes are formed in parts of the interlayer insulating films 514a and 514b. Subsequently, a conductive material is buried in the holes to form connection pillars 514c to 514e. In this case, the connection pillar 514c is electrically connected to the source 512S of a transistor 532, and the connection pillar 514d is electrically connected to the drain 512D, for example. The connection pillar 514e is electrically connected to the source 512S of another transistor 532, for example. Subsequently, a conductive material is buried in the trenches to form interconnection units 514f and 514g. The interconnection unit 514f is electrically connected to the connection pillar 514c and the connection pillar 514d. The interconnection unit 514g is electrically connected to the connection pillar 514e. Subsequently, an interlayer insulating film 514h is formed on the interlayer insulating film 514b.

As shown in FIG. 30A and FIG. 30B, an interlayer insulating film 514*i* made of silicon oxide (SiO$_2$) is formed on the interlayer insulating film 514*h* using the CVD (chemical vapor deposition) method, for example. Subsequently, holes are formed in prescribed positions of the interlayer insulating film 514*i*, a conductive material (for example, a metal material) is buried, and the upper surface is planarized using the CMP (chemical mechanical polishing) method. Thereby, a connection pillar 514*j* connected to the interconnection unit 514*f* and a connection pillar 514*k* connected to the interconnection unit 514*g* are formed.

Figure 31A:
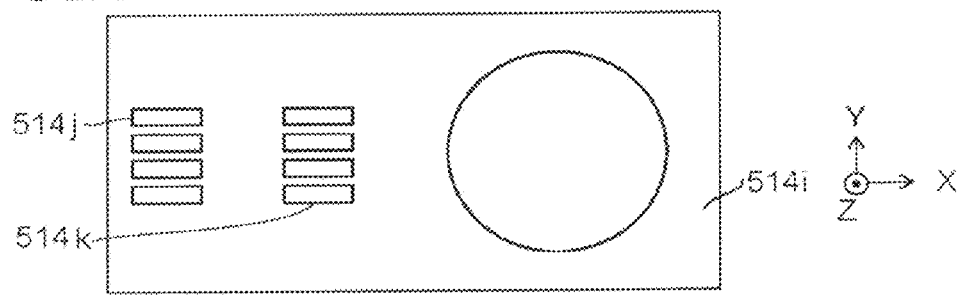
FIG. 31A and FIG. 31B are schematic views showing a method for manufacturing a pressure sensor according to the embodiment.
Figure 31B:
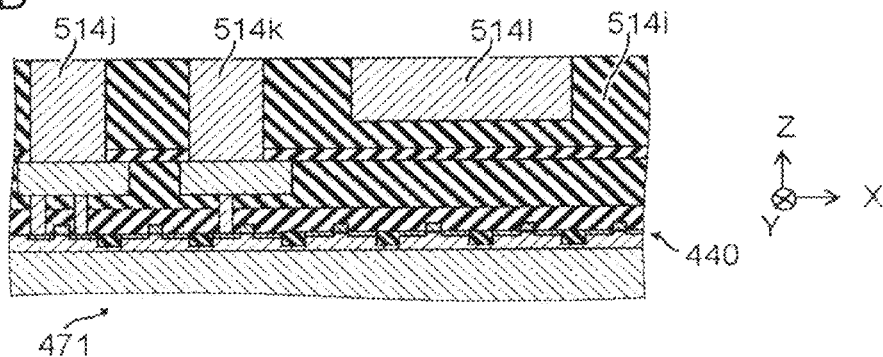

As shown in FIG. 31A and FIG. 31B, a recess is formed in a region of the interlayer insulating film 514*i* that forms a hollow portion 570, and a sacrifice layer 514*l* is buried in the recess. The sacrifice layer 514*l* may be formed using a material that can be formed into a film at low temperature, for example. The material that can be made into a film at low temperature is silicon germanium (SiGe) or the like, for example.

Figure 32A:
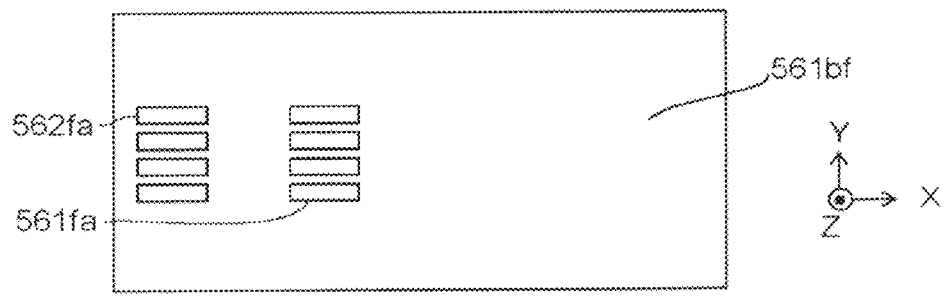
FIG. 32A and FIG. 32B are schematic views showing a method for manufacturing a pressure sensor according to the embodiment.
Figure 32B:
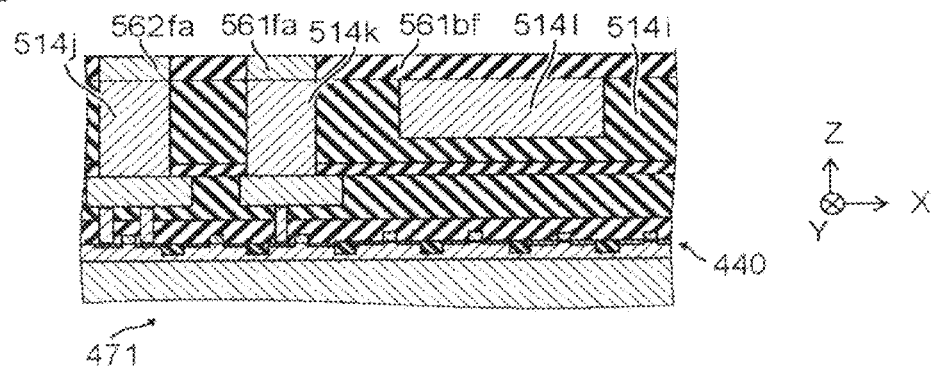

As shown in FIG. 32A and FIG. 32B, an insulating film 561*bf* that forms a film unit 564 (70*d*) is formed on the interlayer insulating film 514*i* and the sacrifice layer 514*l*. The insulating film 561*bf* may be formed using silicon oxide (SiO$_2$) or the like, for example. A plurality of holes are provided in the insulating film 561*bf*, and a conductive material (for example, a metal material) is buried in the plurality of holes to form a connection pillar 561*fa* and a connection pillar 562*fa*. The connection pillar 561*fa* is electrically connected to the connection pillar 514*k*, and the connection pillar 562*fa* is electrically connected to the connection pillar 514*j*.

Figure 33A:
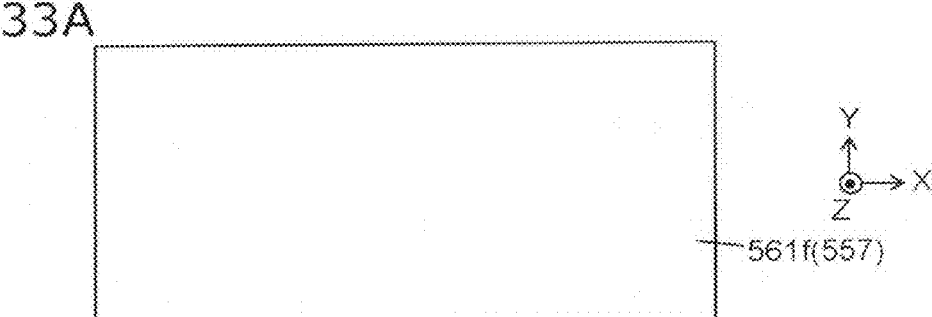
FIG. 33A and FIG. 33B are schematic views showing a method for manufacturing a pressure sensor according to the embodiment.
Figure 33B:
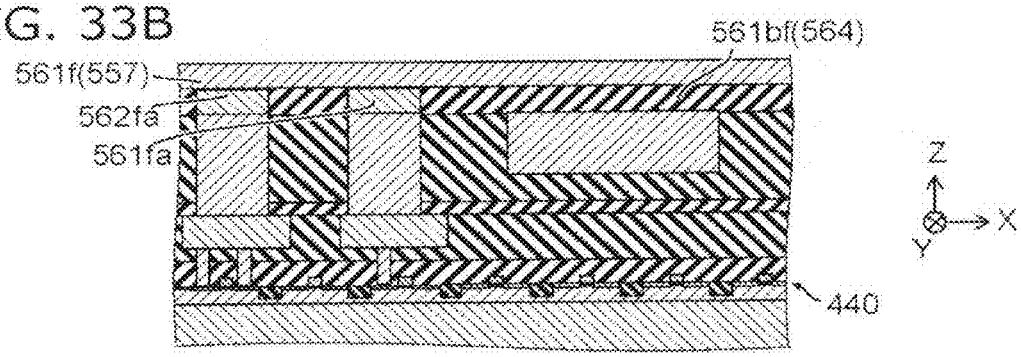

As shown in FIG. 33A and FIG. 33B, a conductive layer 561*f* that forms an interconnection 557 is formed on the insulating film 561*bf*, the connection pillar 561*fa*, and the connection pillar 562*fa*.

Figure 34A:
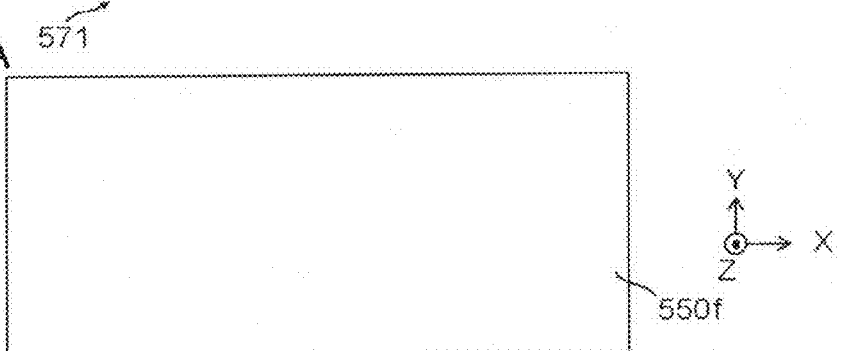
FIG. 34A and FIG. 34B are schematic views showing a method for manufacturing a pressure sensor according to the embodiment.
Figure 34B:
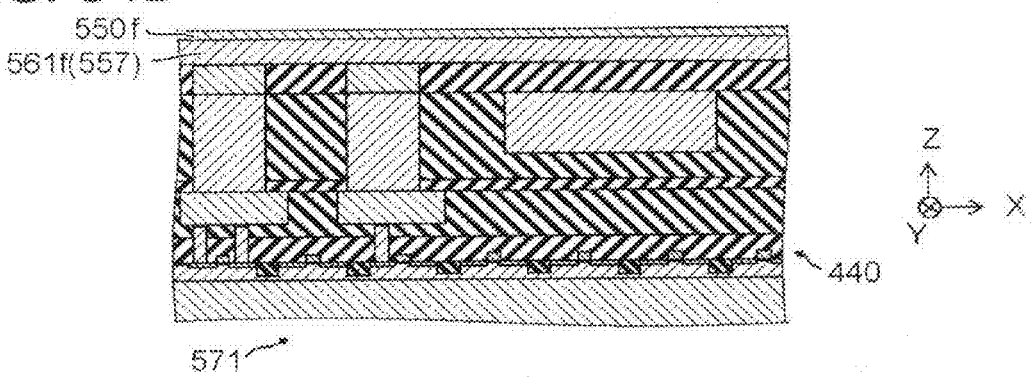

As shown in FIG. 34A and FIG. 34B, a stacked film 550*f* is formed on the conductive layer 561*f*.

Figure 35A:
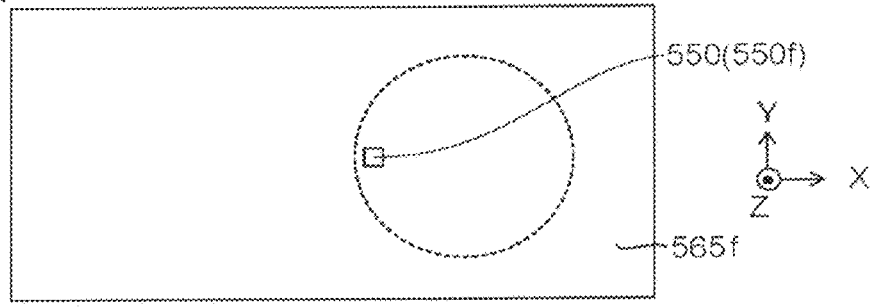
FIG. 35A and FIG. 35B are schematic views showing a method for manufacturing a pressure sensor according to the embodiment.
Figure 35B:
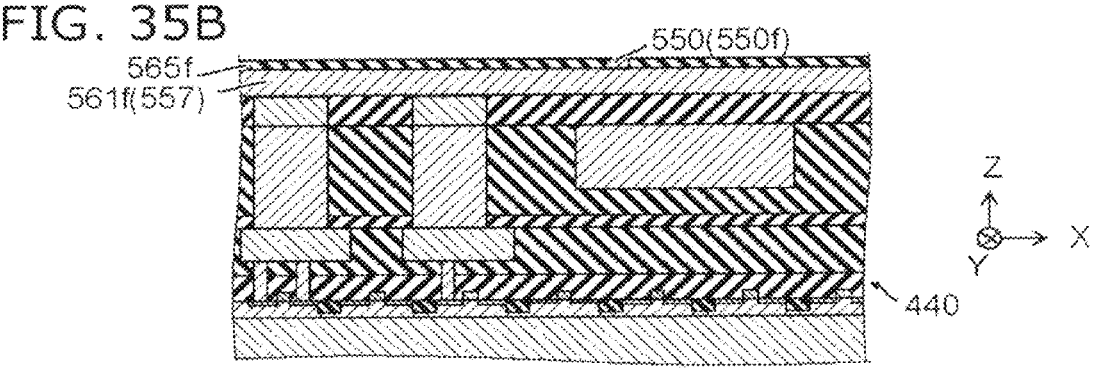

As shown in FIG. 35A and FIG. 35B, the stacked film 550*f* is processed into a prescribed shape, and an insulating film 565*f* that forms an insulating layer 565 is formed thereon. The insulating film 565*f* may be formed using silicon oxide (SiO$_2$) or the like, for example.

Figure 36A:
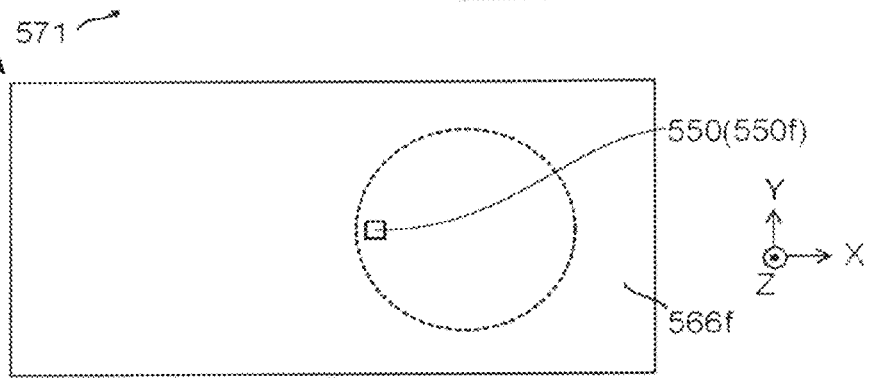
FIG. 36A and FIG. 36B are schematic views showing a method for manufacturing a pressure sensor according to the embodiment.
Figure 36B:
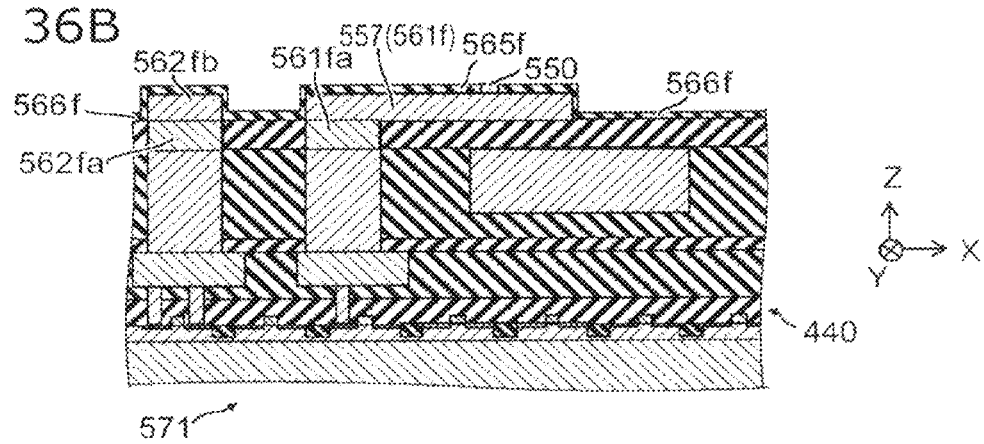

As shown in FIG. 36A and FIG. 36B, part of the insulating film 565*f* is removed, and the conductive layer 561*f* is processed into a prescribed shape. Thereby, an interconnection 557 is formed. At this time, part of the conductive layer 561*f* forms a connection pillar 562*fb* electrically connected to the connection pillar 562*fa*. Then, an insulating film 566*f* that forms an insulating layer 566 is formed thereon.

Figure 37A:
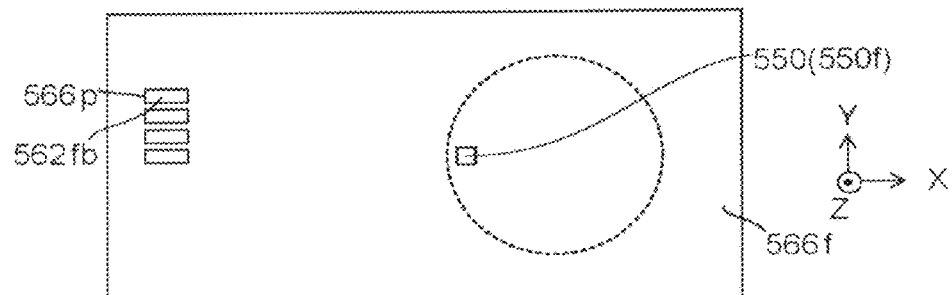
FIG. 37A and FIG. 37B are schematic views showing a method for manufacturing a pressure sensor according to the embodiment.
Figure 37B:
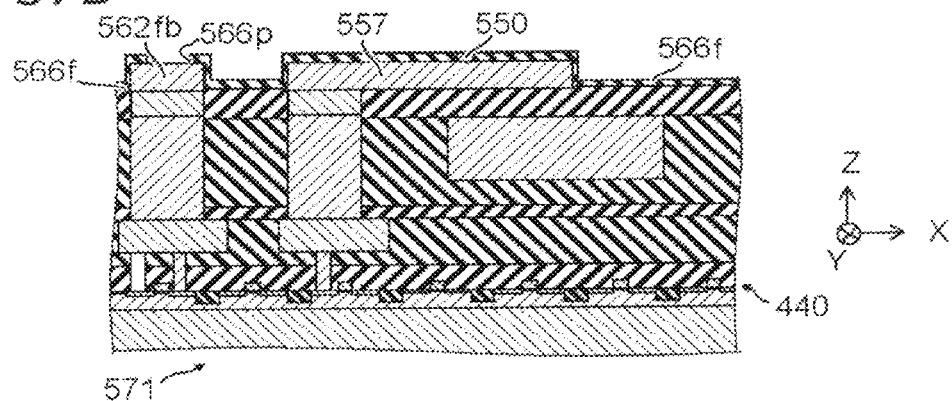

As shown in FIG. 37A and FIG. 37B, an opening 566*p* is formed in the insulating film 566*f*. Thereby, the connection pillar 562*fb* is exposed.

Figure 38A:
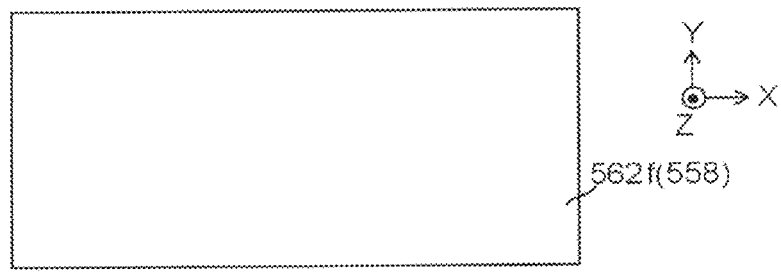
FIG. 38A and FIG. 38B are schematic views showing a method for manufacturing a pressure sensor according to the embodiment.
Figure 38B:
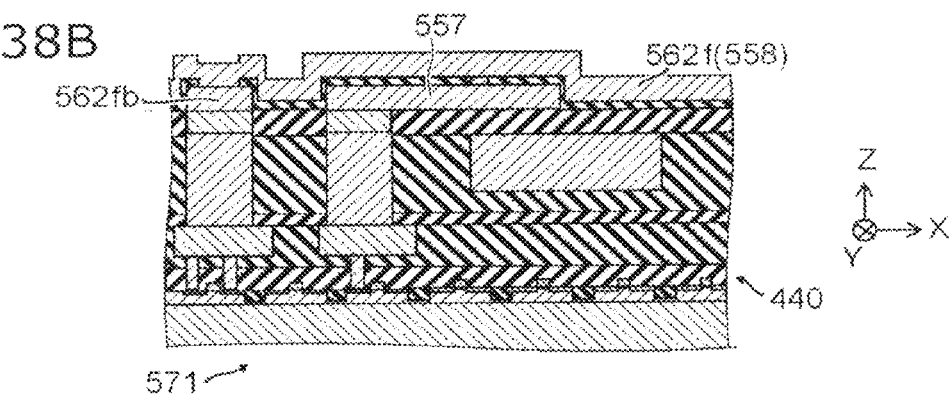

As shown in FIG. 38A and FIG. 38B, a conductive layer 562*f* that forms an interconnection 558 is formed on the upper surface. Part of the conductive layer 562*f* is electrically connected to the connection pillar 562*fb*.

Figure 39A:
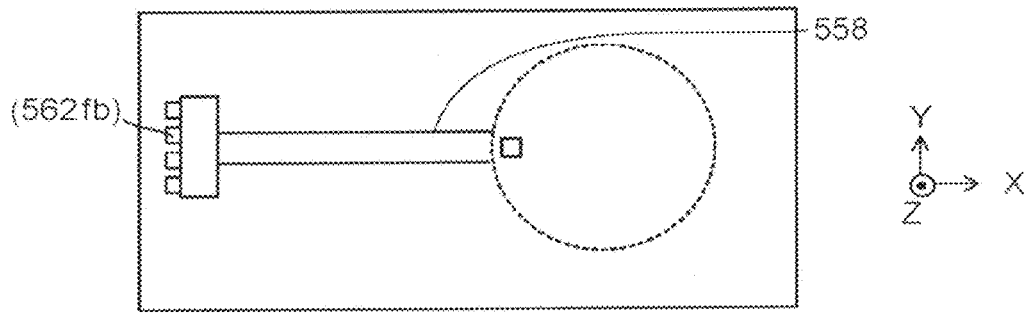
FIG. 39A and FIG. 39B are schematic views showing a method for manufacturing a pressure sensor according to the embodiment.
Figure 39B:
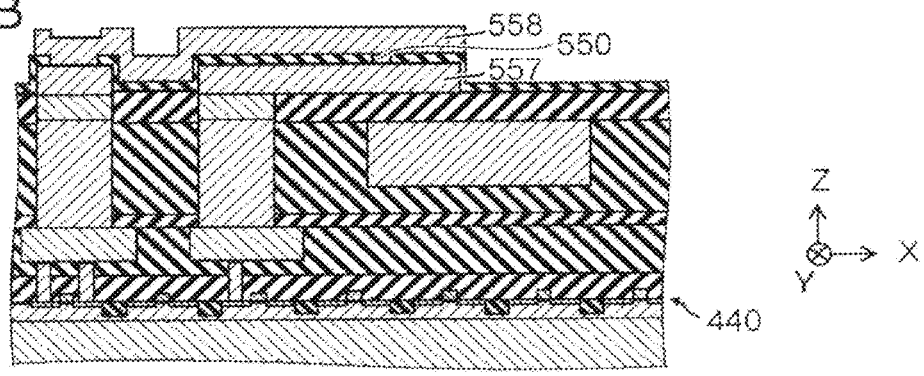

As shown in FIG. 39A and FIG. 39B, the conductive layer 562*f* is processed into a prescribed shape. Thereby, an interconnection 558 is formed. The interconnection 558 is electrically connected to the connection pillar 562*fb*.

Figure 40A:
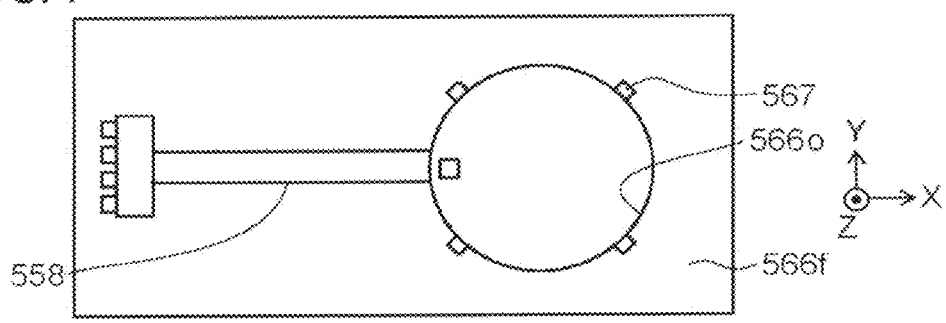
FIG. 40A and FIG. 40B are schematic views showing a method for manufacturing a pressure sensor according to the embodiment.
Figure 40B:
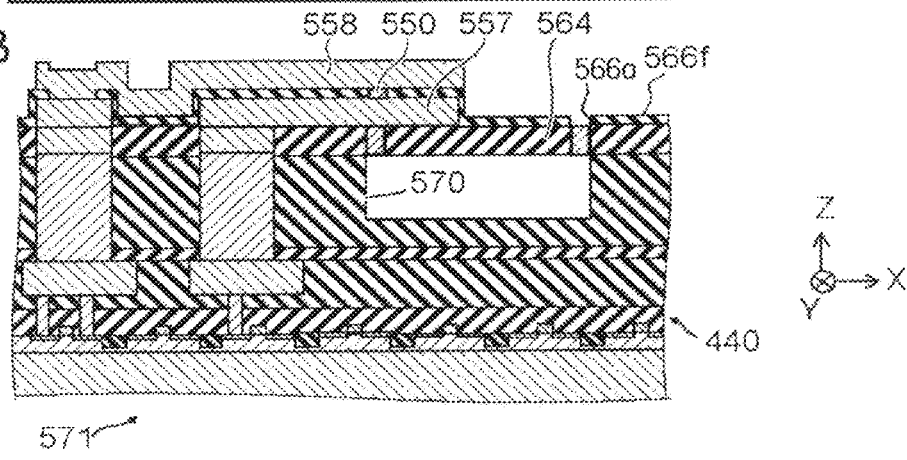

As shown in FIG. 40A and FIG. 40B, an opening 566*o* with a prescribed shape is formed in the insulating film 566*f*. The insulating film 561*bf* is processed via the opening 566*o*, and the sacrifice layer 514*l* is removed via the opening 566*o*. Thereby, a hollow portion 570 is formed. The removal of the sacrifice layer 514*l* can be performed using the wet etching method, for example.

When a fixing unit 567 is shaped like a ring, the space between the edge of the non-hollow portion above the hollow portion 570 and the film unit 564 is filled with an insulating film, for example.

Thus, a pressure sensor is formed.

Fourth Embodiment

The embodiment relates to a microphone using the pressure sensor according to the embodiments described above.

Figure 41:
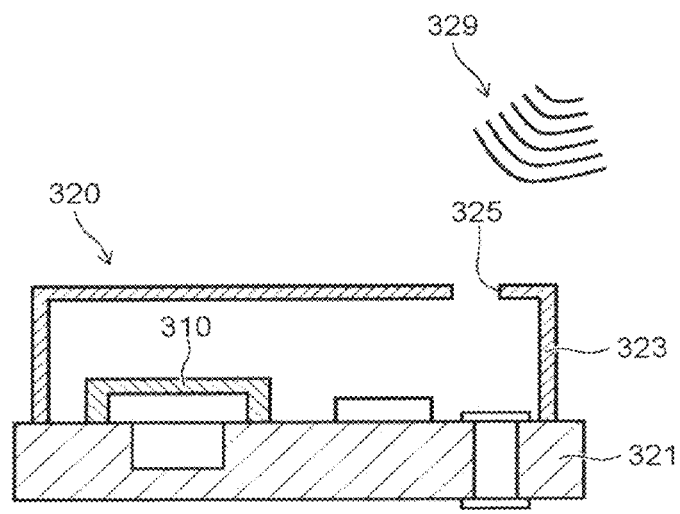
FIG. 41 is a schematic cross-sectional view showing a microphone according to a fourth embodiment.

FIG. 41 is a schematic cross-sectional view illustrating a microphone according to a fourth embodiment.

A microphone 320 according to the embodiment includes a printed circuit board 321, a cover 323, and a pressure sensor 310. The printed circuit board 321 includes a circuit of an amplifier etc., for example. An acoustic hole 325 is provided in the cover 323. Sound 329 passes through the acoustic hole 325 to enter the inside of the cover 323.

As the pressure sensor 310, any one of the pressure sensors described in regard to the embodiments and modifications thereof are used.

The microphone 320 reacts to sound pressure. By using a high-sensitivity pressure sensor 310, a high-sensitivity microphone 320 is obtained. The pressure sensor 310 is mounted on the printed circuit board 321, and an electric signal line is provided, for example. The cover 323 is provided on the printed circuit board 321 so as to cover the pressure sensor 310.

The embodiment can provide a high-sensitivity microphone.

Fifth Embodiment

The embodiment relates to a blood pressure sensor using the pressure sensor according to the embodiments described above.

Figures 42A, 42B:
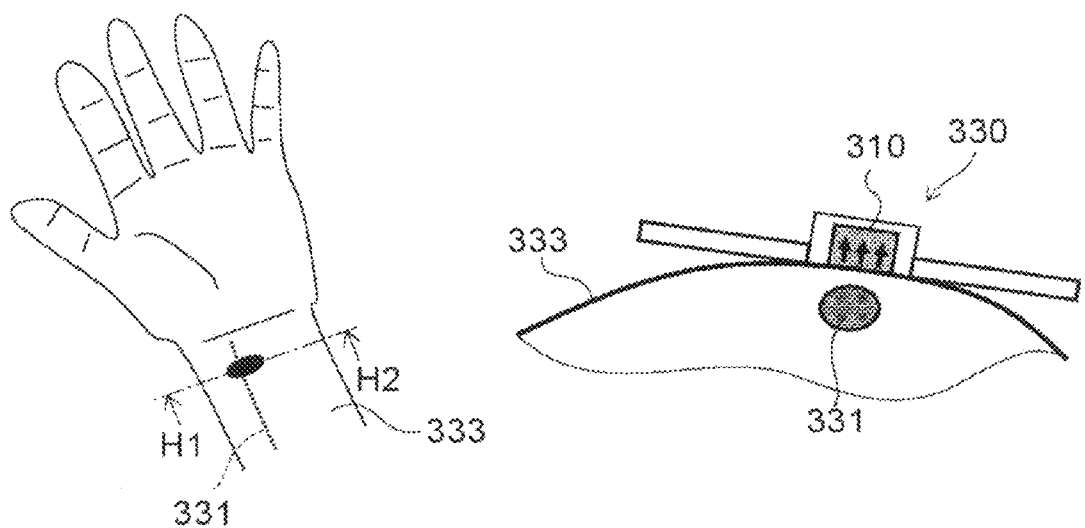
FIG. 42A and FIG. 42B are schematic views showing a blood pressure sensor according to a fifth embodiment.

FIG. 42A and FIG. 42B are schematic views illustrating a blood pressure sensor according to a fifth embodiment.

FIG. 42A is a schematic plan view illustrating the skin on an artery of a person. FIG. 42B is a cross-sectional view taken along line H1-H2 of FIG. 42A.

In the embodiment, the pressure sensor 310 is used as a blood pressure sensor 330. Any one of the pressure sensors described in regard to the embodiments and modifications thereof are used as the pressure sensor 310.

Thus, high-sensitivity pressure sensing can be made by a small-sized pressure sensor. By pressing the pressure sensor 310 against the skin 333 on an artery 331, the blood pressure sensor 330 can make blood pressure measurement continuously.

The embodiment can provide a high-sensitivity blood pressure sensor.

Sixth Embodiment

The embodiment relates to a touch panel using the pressure sensor of the embodiments described above.

Figure 43:
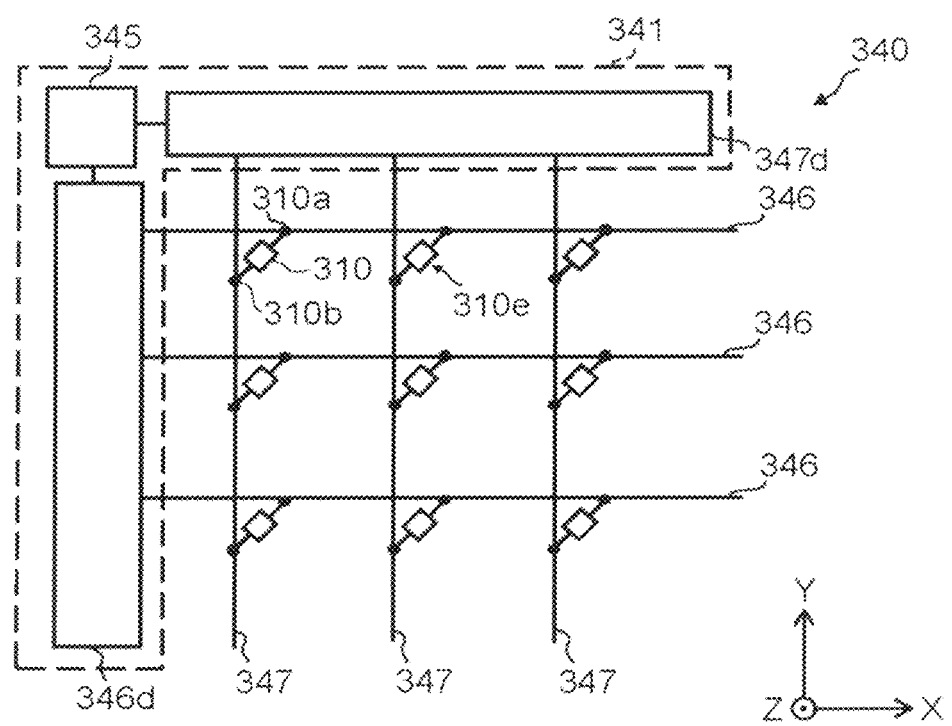
FIG. 43 is a schematic diagram showing a touch panel according to a sixth embodiment.

FIG. 43 is a schematic diagram illustrating a touch panel according to a sixth embodiment.

In the embodiment, the pressure sensor 310 is used as a touch panel 340. Any one of the pressure sensors described in regard to the embodiments and modifications thereof are used as the pressure sensor 310. In the touch panel 340, the pressure sensor 310 is mounted at least one of in a display and outside a display.

The touch panel 340 includes a plurality of first interconnections 346, a plurality of second interconnections 347, a plurality of pressure sensors 310, and a control unit 341, for example.

In this example, the plurality of first interconnections 346 are aligned along the Y-axis direction. Each of the plurality of first interconnections 346 extends along the X-axis direction. The plurality of second interconnections 347 are aligned along the X-axis direction. Each of the plurality of second interconnections 347 extends along the Y-axis direction.

Each of the plurality of pressure sensors 310 is provided in the intersection portion of each of the plurality of first interconnections 346 and each of the plurality of second interconnections 347. One pressure sensor 310 forms one sensing element 310e for detection. Here, the intersection portion includes the position where the first interconnection 346 and the second interconnection 347 cross each other and a region around this.

One end 310a of each of the plurality of pressure sensors 310 is connected to each of the plurality of first interconnections 346. The other end 310b of each of the plurality of pressure sensors 310 is connected to each of the plurality of second interconnections 347.

The control unit 341 is connected to the plurality of first interconnections 346 and the plurality of second interconnections 347.

The control unit 341 includes a circuit for the first interconnection 346d connected to the plurality of first interconnections 346, a circuit for the second interconnection 347d connected to the plurality of second interconnections 347, and a control circuit 345 connected to the circuit for the first interconnection 346d and the circuit for the second interconnection 347d, for example.

The pressure sensor 310 can make high-sensitivity pressure sensing with a small size. Thus, a high-definition touch panel can be provided.

The pressure sensor according to the embodiment can be used for various pressure sensor devices such as atmospheric pressure sensors and air pressure sensors for tires, as well as the uses mentioned above.

The embodiment can provide a strain sensing element, a pressure sensor, a microphone, a blood pressure sensor, and a touch panel of high sensitivity.

Hereinabove, embodiments of the invention are described with reference to specific examples. However, the invention is not limited to these specific examples. For example, one skilled in the art may appropriately select specific configurations of components of sensing elements, pressure sensors, microphones, blood pressure sensors, and touch panels such as film units, strain sensing elements, first magnetic layers, second magnetic layers, and intermediate layers from known art and similarly practice the invention. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all strain sensing elements, pressure sensors, microphones, blood pressure sensors, and touch panels practicable by an appropriate design modification by one skilled in the art based on the strain sensing elements, the pressure sensors, microphones, the blood pressure sensors, and the touch panels described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A strain sensing element provided on a film being deformable, the strain sensing element comprising:
    a non-magnetic layer;
    a first magnetic layer;
    a functional layer provided between the non-magnetic layer and the first magnetic layer, the functional layer contacting the non-magnetic layer, the functional layer including at least one selected from the group consisting of an oxide and a nitride;
    a second magnetic layer provided between the functional layer and the first magnetic layer, a magnetization of the second magnetic layer being variable in accordance with a deformation of the film; and
    a spacer layer provided between the first magnetic layer and the second magnetic layer,
    at least a part of the second magnetic layer being amorphous and including boron.

2. The element according to claim 1, wherein
    the oxide includes an oxide of at least one selected from the group consisting of magnesium, aluminum, silicon, titanium, vanadium, chromium, manganese, iron, cobalt, nickel, copper, zinc, zirconium, niobium, molybdenum, ruthenium, rhodium, palladium, silver, hafnium, tantalum, tungsten, tin, cadmium, and gallium, and
    the nitride includes a nitride of at least one selected from the group consisting of magnesium, aluminum, silicon, titanium, vanadium, chromium, manganese, iron, cobalt, nickel, copper, zinc, zirconium, niobium, molybdenum, ruthenium, rhodium, palladium, silver, hafnium, tantalum, tungsten, tin, cadmium, and gallium.

3. The element according to claim 1, wherein the functional layer includes an oxide of at least one selected from the group consisting of magnesium, titanium, vanadium, zinc, tin, cadmium, and gallium.

4. The element according to claim 1, wherein the functional layer includes magnesium oxide.

5. The element according to claim 1, wherein a thickness of the functional layer is not more than one nanometer.

6. The element according to claim 1, wherein a concentration of boron included in the functional layer is not less than 5 atomic percent and not more than 35 atomic percent.

7. The element according to claim 1, wherein
    the second magnetic layer includes a first portion and a second portion,
    the first portion is provided between the second portion and the spacer layer, and
    a concentration of boron in the first portion is lower than a concentration of boron in the second portion.

8. The element according to claim 1, wherein
the second magnetic layer includes a first portion and a second portion,
the first portion is provided between the second portion and the spacer layer, and
the first portion has crystallinity.

9. The element according to claim 1, wherein a magnetostriction constant of the second magnetic layer is not less than $1 \times 10^{-5}$.

10. The element according to claim 1, wherein a coercivity of the second magnetic layer is not more than 5 oersteds.

11. The element according to claim 1, wherein a sheet resistivity of the functional layer is lower than a sheet resistivity of the spacer layer.

12. A pressure sensor comprising:
a film being deformable; and
a strain sensing element provided on the film, the strain sensing element including:
  a non-magnetic layer;
  a first magnetic layer;
  a functional layer provided between the non-magnetic layer and the first magnetic layer, the functional layer contacting the non-magnetic layer, the functional layer including at least one selected from the group consisting of an oxide and a nitride;
  a second magnetic layer provided between the functional layer and the first magnetic layer, a magnetization of the second magnetic layer being variable in accordance with a deformation of the film; and
  a spacer layer provided between the first magnetic layer and the second magnetic layer,
  at least a part of the second magnetic layer being amorphous and including boron.

13. The sensor according to claim 12, wherein the strain sensing element is provided in a plurality.

14. The sensor according to claim 12, wherein at least two of the plurality of strain sensing elements are electrically connected in series.

15. The sensor according to claim 14, wherein a voltage of not less than 1 V and not more than 10 V is applied between terminals of the strain sensing elements electrically connected in series.

16. The sensor according to claim 14, wherein a number of strain sensing elements electrically connected in series is not less than 6 and not more than 200.

17. A strain sensing element provided on a film being deformable, the strain sensing element comprising:
a non-magnetic layer;
a first magnetic layer;
a functional layer provided between the non-magnetic layer and the first magnetic layer, the functional layer contacting the non-magnetic layer, the functional layer including at least one element selected from the group consisting of magnesium, silicon, and aluminum;
a second magnetic layer provided between the functional layer and the first magnetic layer, a magnetization of the second magnetic layer being variable in accordance with a deformation of the film; and
a spacer layer provided between the first magnetic layer and the second magnetic layer,
at least a part of the second magnetic layer being amorphous and including boron.

18. A microphone comprising:
a pressure sensor, the pressure sensor including:
a film being deformable; and
a strain sensing element provided on the film, the strain sensing element including:
  a non-magnetic layer;
  a first magnetic layer;
  a functional layer provided between the non-magnetic layer and the first magnetic layer, the functional layer contacting the non-magnetic layer, the functional layer including at least one selected from the group consisting of an oxide and a nitride;
  a second magnetic layer provided between the functional layer and the first magnetic layer, a magnetization of the second magnetic layer being variable in accordance with a deformation of the film; and
  a spacer layer provided between the first magnetic layer and the second magnetic layer,
at least a part of the second magnetic layer being amorphous and including boron.

19. A blood pressure sensor comprising:
a pressure sensor, the pressure sensor including:
a film being deformable; and
a strain sensing element provided on the film, the strain sensing element including:
  a non-magnetic layer;
  a first magnetic layer;
  a functional layer provided between the non-magnetic layer and the first magnetic layer, the functional layer contacting the non-magnetic layer, the functional layer including at least one selected from the group consisting of an oxide and a nitride;
  a second magnetic layer provided between the functional layer and the first magnetic layer, a magnetization of the second magnetic layer being variable in accordance with a deformation of the film; and
  a spacer layer provided between the first magnetic layer and the second magnetic layer,
  at least a part of the second magnetic layer being amorphous and including boron.

20. A touch panel comprising:
a pressure sensor, the pressure sensor including:
a film being deformable; and
a strain sensing element provided on the film, the strain sensing element including:
  a non-magnetic layer;
  a first magnetic layer;
  a functional layer provided between the non-magnetic layer and the first magnetic layer, the functional layer contacting the non-magnetic layer, the functional layer including at least one selected from the group consisting of an oxide and a nitride;
  a second magnetic layer provided between the functional layer and the first magnetic layer, a magnetization of the second magnetic layer being variable in accordance with a deformation of the film; and
  a spacer layer provided between the first magnetic layer and the second magnetic layer,
  at least a part of the second magnetic layer being amorphous and including boron.

* * * * *